United States Patent
Mohan et al.

(10) Patent No.: US 11,230,555 B2
(45) Date of Patent: Jan. 25, 2022

(54) BICYCLIC RORγ MODULATORS

(71) Applicant: Escalier Biosciences B.V., Encinitas, CA (US)

(72) Inventors: Raju Mohan, Encinitas, CA (US); John Nuss, Encinitas, CA (US); Jason Harris, Encinitas, CA (US); Shendong Yuan, Encinitas, CA (US)

(73) Assignee: ESCALIER BIOSCIENCES B.V., Encinitas, CA (US)

( * ) Notice: Subject to any disclaimer, the term of this patent is extended or adjusted under 35 U.S.C. 154(b) by 0 days.

(21) Appl. No.: 16/979,834

(22) PCT Filed: Mar. 11, 2019

(86) PCT No.: PCT/US2019/021668
§ 371 (c)(1),
(2) Date: Sep. 10, 2020

(87) PCT Pub. No.: WO2019/177996
PCT Pub. Date: Sep. 19, 2019

(65) Prior Publication Data
US 2021/0053987 A1    Feb. 25, 2021

Related U.S. Application Data

(60) Provisional application No. 62/641,951, filed on Mar. 12, 2018.

(51) Int. Cl.
| | | |
|---|---|---|
| *C07D 498/08* | (2006.01) | |
| *C07D 221/24* | (2006.01) | |
| *C07D 471/08* | (2006.01) | |
| *C07D 487/08* | (2006.01) | |
| *A61P 37/06* | (2006.01) | |

(52) U.S. Cl.
CPC ............ *C07D 498/08* (2013.01); *A61P 37/06* (2018.01); *C07D 221/24* (2013.01); *C07D 471/08* (2013.01); *C07D 487/08* (2013.01)

(58) Field of Classification Search
CPC .. C07D 498/08; C07D 221/24; C07D 471/08; C07D 487/08; A61P 37/06
See application file for complete search history.

(56) References Cited

U.S. PATENT DOCUMENTS

| | | |
|---|---|---|
| 6,432,957 B1 | 8/2002 | Kodoma et al. |
| 9,586,928 B2 | 3/2017 | Kamenecka et al. |
| 2010/0029621 A1 | 2/2010 | Cooke et al. |
| 2014/0031330 A1 | 1/2014 | Bodil et al. |
| 2014/0187554 A1 | 7/2014 | Kamenecka et al. |
| 2016/0120850 A1 | 5/2016 | Goldberg et al. |
| 2016/0122335 A1 | 5/2016 | Goldberg et al. |
| 2016/0122336 A1 | 5/2016 | Goldberg et al. |
| 2016/0318870 A1 | 11/2016 | Dhar et al. |
| 2017/0313691 A1 | 11/2017 | Goldberg et al. |
| 2019/0269674 A1 | 9/2019 | Mohan et al. |

FOREIGN PATENT DOCUMENTS

| | | |
|---|---|---|
| WO | WO-2004032933 A1 | 4/2004 |
| WO | WO-2011115892 A1 | 9/2011 |
| WO | WO-2012158784 A2 | 11/2012 |
| WO | WO-2016014910 A1 | 1/2016 |
| WO | WO-2017127442 A1 | 7/2017 |
| WO | WO-2017131156 A1 | 8/2017 |
| WO | WO-2018081558 A1 | 5/2018 |
| WO | WO-2019177996 A1 | 9/2019 |
| WO | WO-2019177997 A1 | 9/2019 |

OTHER PUBLICATIONS

Amselem et al.: In vitro tests to predict in vivo performance of liposomal dosage forms. Chem Phys Lipids 64: 219-237 (1993).
Burnham et al.: Polymers for delivering peptides and proteins. Am J Hosp Pharm 51: 210-218 (1994).
Co-pending U.S. Appl. No. 16/979,833, inventors Mohan; Raju et al., filed Sep. 10, 2020.
Co-pending U.S. Appl. No. 17/102,105, inventors Mohan; Raju et al., filed Nov. 23, 2020.
Davis et al.: Enzyme polyethylene glycol adducts: modified enzymes with unique properties. Enzyme Eng 4:169-173 (1978).
Hackam et al., Translation of research evidence from animals to humans. JAMA, 296(14):1731-1732, 2006.
International Application No. PCT/US2017/058755 International Preliminary Report on Patentability dated Apr. 30, 2019.
International Application No. PCT/US2017/058755 International Search Report and Written Opinion dated Feb. 23, 2018.
Jordan, V. C., "Tamoxifen: a most unlikely pioneering medicine" Nature Reviews: Drug Discovery, 2, 2003, 205.
PCT/US2019/021668 International Search Report and Written Opinion dated May 30, 2019.
PCT/US2019/021671 International Search Report and Written Opinion dated Jul. 10, 2019.
PubChem CID 3233343, https://pubchem.ncbi.nlm.nih.gov/compound/3233343 (2005).
Science IP Search Results (2016) 93 pages.
U.S. Appl. No. 16/344,919 Office Action dated May 1, 2020.
Vippagunta et al. Crystalline Solids. Advanced Drug Delivery Reviews 48:3-26 (2001).
Wu et al., Discovery and structural optimization of 4-(4-(benzyloxy)phenyl)-3,4-dihydropyrimidin-2(1H)-ones as RORc inverse agonists. Acta Pharmacologica Sinica. 37(11):1516-1524 (2016).
European Application No. 19768383 Search Report dated Oct. 13, 2021.

*Primary Examiner* — Rebecca L Anderson
(74) *Attorney, Agent, or Firm* — Wilson Sonsini Goodrich & Rosati

(57) ABSTRACT

Described herein are retinoic acid related-related orphan nuclear receptor (ROR) modulators and methods of utilizing ROR-gamma modulators in the treatment of diseases, disorders or conditions. Also described herein are pharmaceutical compositions containing such compounds.

19 Claims, No Drawings

BICYCLIC RORγ MODULATORS

CROSS-REFERENCE

This application is a U.S. National Phase of International Application No.: PCT/US2019/21668, filed Mar. 11, 2019, which claims benefit of U.S. Provisional Application No. 62/641,951, filed on Mar. 12, 2018, which are herein incorporated by reference in their entirety.

BACKGROUND OF THE INVENTION

The retinoic acid related orphan nuclear receptors (RORs) have three members: RORα, RORβ and RORγ. RORβ expression is mostly restricted to the brain and retina, while RORα and RORγ expressions are widespread. RORγ also has a shorter isoform, RORγt, which is mostly expressed in the immune system.

RORγt is essential for the development of secondary lymphoid tissues, in particular lymph nodes and Peyer's patches. Recent studies identified a critical role for RORγt in lineage specification of uncommitted CD4+ T helper cells into Th17 cells as well as the development of Tc17 (cytotoxic) T cells. Th17 response has been implicated in a myriad of autoimmune diseases such as psoriasis, inflammatory bowel disease, arthritis and multiple scoliosis. Inhibition of Th17 and Tc17 response has also been shown to a mechanism for cancer cells to evade anti-tumor immunity in several experimental tumor models. These findings implicate both RORγ agonists and inverse agonists as potential therapeutics for a variety of diseases.

SUMMARY OF THE INVENTION

In one aspect, provided herein are compounds having the Formula I, or a pharmaceutically acceptable salt, solvate, or stereoisomer thereof:

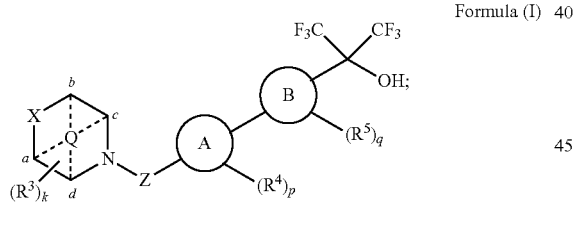

Formula (I)

wherein:

is phenyl, or a 5-membered or 6-membered heteroaryl ring;

is phenyl, or a 5-membered or 6-membered heteroaryl ring;
Q is $-(CH_2)_n-$, $-CH_2YCH_2-$, or $-(CH_2)_mY-$, wherein $-(CH_2)_n-$, $-CH_2YCH_2-$, or $-(CH_2)_mY-$ is attached to the ring carbon atoms at a and b, c and d, a and c, or b and d;

X is $-N(R^{3a})-$, $-C(R^{3b})(R^{3c})-$, or $-O-$;
Y is $-O-$, $-S-$, or $-N(R^{3d})-$;
Z is $-(C(R^1)(R^2))-$;
each $R^1$ and each $R^2$ are each independently hydrogen, halo, or $C_1$-$C_6$alkyl;
each $R^3$ is independently selected from halo and $C_1$-$C_6$alkyl;
$R^{3a}$ is hydrogen, $C_1$-$C_6$alkyl, $C_1$-$C_6$haloalkyl, $C_2$-$C_9$heteroaryl, ($C_2$-$C_9$heteroaryl)-$C_1$-$C_6$alkylene-, $-S(O)_2R^{10}$, $-C(O)R^{10}$, $-C(O)OR^{11}$, or $-C(O)N(R^{11})_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;
$R^{3b}$ is hydrogen, halo, $C_1$-$C_6$alkyl, $C_1$-$C_6$haloalkyl, $-N(R^{11})S(O)_2R^{10}$, $-S(O)_2R^{10}$, $-C(O)R^{10}$, $-C(O)OR^{11}$, or $-C(O)N(R^{11})_2$;
$R^{3c}$ is hydrogen, halo, $C_1$-$C_6$alkyl, or $C_1$-$C_6$haloalkyl;
$R^{3d}$ is selected from hydrogen, $C_1$-$C_6$alkyl, $C_1$-$C_6$haloalkyl, $-S(O)_2R^8$, $-C(O)R^8$, $-C(O)OR^9$, and $-C(O)N(R^9)_2$;
each $R^4$ and each $R^5$ are each independently selected from halo, cyano, $C_1$-$C_6$alkyl, $C_1$-$C_6$haloalkyl, $C_1$-$C_6$alkoxy, $-N(R^7)_2$, $-C(O)R^6$, $-C(O)OR^7$, $-C(O)N(R^7)_2$, $-N(R^7)C(O)R^6$, $-N(R^7)SO_2R^6$, $-SO_2R^6$, and $-SO_2N(R^7)_2$;
each $R^6$ is independently $C_1$-$C_6$alkyl or $C_1$-$C_6$haloalkyl;
each $R^7$ is independently hydrogen, $C_1$-$C_6$alkyl, or $C_1$-$C_6$haloalkyl;
$R^8$ is $C_1$-$C_6$alkyl or $C_1$-$C_6$haloalkyl;
each $R^9$ is independently hydrogen, $C_1$-$C_6$alkyl, or $C_1$-$C_6$haloalkyl;
$R^{10}$ is $C_1$-$C_6$alkyl, $C_1$-$C_6$haloalkyl, $C_1$-$C_6$alkyl-O-$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;
each $R^{11}$ is independently hydrogen, $C_1$-$C_6$alkyl, or $C_1$-$C_6$haloalkyl;
k is 0, 1, 2, 3, or 4;
m is 1 or 2;
n is 1, 2, 3, or 4;
p is 0, 1, 2, 3, or 4;
q is 0, 1, 2, 3, or 4; and
t is 0, 1, 2, or 3.

In some embodiments is a compound of Formula (I), or a pharmaceutically acceptable salt, solvate, or stereoisomer thereof, wherein

is phenyl or a 6-membered heteroaryl ring. In some embodiments is a compound of Formula (I), or a pharmaceutically acceptable salt, solvate, or stereoisomer thereof, wherein

is phenyl. In some embodiments is a compound of Formula (I), or a pharmaceutically acceptable salt, solvate, or stereoisomer thereof, wherein (B)

is 6-membered heteroaryl ring. In some embodiments is a compound of Formula (I), or a pharmaceutically acceptable salt, solvate, or stereoisomer thereof, wherein (B)

is pyridyl. In some embodiments is a compound of Formula (I), or a pharmaceutically acceptable salt, solvate, or stereoisomer thereof, wherein (A)

is phenyl or a 6-membered heteroaryl ring. In some embodiments is a compound of Formula (I), or a pharmaceutically acceptable salt, solvate, or stereoisomer thereof, wherein (A)

is phenyl. In some embodiments is a compound of Formula (I), or a pharmaceutically acceptable salt, solvate, or stereoisomer thereof, wherein (A)

is a 6-membered heteroaryl ring. In some embodiments is a compound of Formula (I), or a pharmaceutically acceptable salt, solvate, or stereoisomer thereof, wherein (A)

is pyridyl.

In some embodiments is a compound of Formula (I), or a pharmaceutically acceptable salt, solvate, or stereoisomer thereof, having the Formula (II):

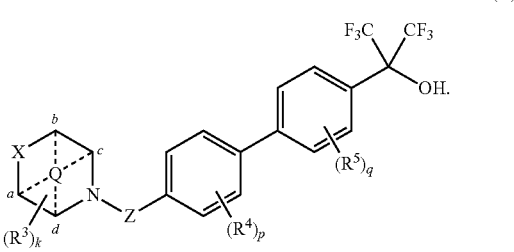

Formula (II)

In some embodiments is a compound of Formula (I) or (II), or a pharmaceutically acceptable salt, solvate, or stereoisomer thereof, wherein X is —N(R$^{3a}$)— or —C(R$^{3b}$)(R$^{3c}$)—.

In some embodiments is a compound of Formula (II), or a pharmaceutically acceptable salt, solvate, or stereoisomer thereof, having the Formula (IIa):

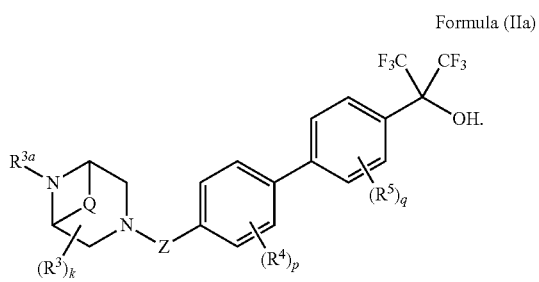

Formula (IIa)

In some embodiments is a compound of Formula (II), or a pharmaceutically acceptable salt, solvate, or stereoisomer thereof, having the Formula (IIb):

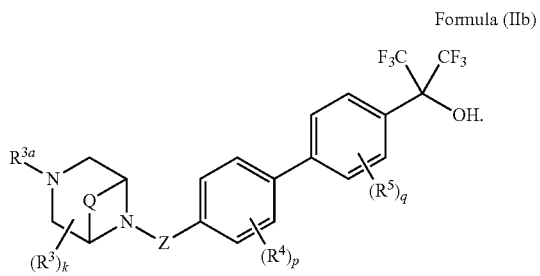

Formula (IIb)

In some embodiments is a compound of Formula (II), or a pharmaceutically acceptable salt, solvate, or stereoisomer thereof, having the Formula (IIc):

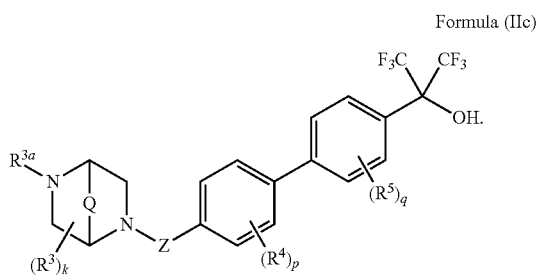

Formula (IIc)

In some embodiments is a compound of Formula (I), (Ia), (Ib), (II), (IIa), (IIb), (IIc), or a pharmaceutically acceptable salt, solvate, or stereoisomer thereof, wherein each $R^1$ and each $R^2$ are hydrogen. In some embodiments is a compound of Formula (I), (Ia), (Ib), (II), (IIa), (IIb), (IIc), or a pharmaceutically acceptable salt, solvate, or stereoisomer thereof, wherein t is 1, 2, or 3. In some embodiments is a compound of Formula (I), (Ia), (Ib), (II), (IIa), (IIb), (IIc), or a pharmaceutically acceptable salt, solvate, or stereoisomer thereof, wherein t is 1. In some embodiments is a compound of Formula (I), (Ia), (Ib), (II), (IIa), (IIb), (IIc), or a pharmaceutically acceptable salt, solvate, or stereoisomer thereof, wherein $R^{3a}$ is $C_1$-$C_6$alkyl, $C_2$-$C_9$heteroaryl, ($C_2$-$C_9$heteroaryl)-$C_1$-$C_6$alkylene-, —S(O)$_2$R$^{10}$, —C(O)R$^{10}$, —C(O)OR$^{11}$, or —C(O)—$C_1$-$C_6$alkylene-OR$^{11}$, wherein $C_2$-$C_9$heteroaryl and ($C_2$-$C_9$heteroaryl)-$C_1$-$C_6$alkylene- are optionally substituted with 1 or 2 groups each independently selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein $R^{3a}$ is $C_1$-$C_6$alkyl, ($C_2$-$C_9$heteroaryl)-$C_1$-$C_6$alkylene-, —S(O)$_2$R$^{10}$, or —C(O)R$^{10}$, wherein ($C_2$-$C_9$heteroaryl)-$C_1$-$C_6$alkylene- is optionally substituted with 1 or 2 groups each independently selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein $R^{3a}$ is ($C_2$-$C_9$heteroaryl)-$C_1$-$C_6$alkylene- or —S(O)$_2$R$^{10}$, wherein ($C_2$-$C_9$heteroaryl)-$C_1$-$C_6$alkylene- is optionally substituted with 1 or 2 groups each independently selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein $R^{3a}$ is —S(O)$_2$R$^{10}$. In some embodiments is a compound of Formula (I), (Ia), (Ib), (II), (IIa), (IIb), (IIc), or a pharmaceutically acceptable salt, solvate, or stereoisomer thereof, wherein $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, or (phenyl)-$C_1$-$C_6$alkylene-, wherein $C_3$-$C_8$cycloalkyl, $C_2$-$C_9$heterocyclyl, or (phenyl)-$C_1$-$C_6$alkylene- is optionally substituted with 1 or 2 groups selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein $R^{10}$ is $C_1$-$C_6$alkyl. In some embodiments is a compound of Formula (I), (Ia), (Ib), (II), (IIa), (Ib), (IIc), or a pharmaceutically acceptable salt, solvate, or stereoisomer thereof, wherein $R^{3a}$ is —S(O)$_2$CH$_3$. In some embodiments is a compound of Formula (I), (Ia), (Ib), (II), (IIa), (Ib), (IIc), or a pharmaceutically acceptable salt, solvate, or stereoisomer thereof, wherein $R^{3a}$ is ($C_2$-$C_9$heteroaryl)-$C_1$-$C_6$alkylene- optionally substituted with 1 or 2 groups each independently selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein $R^{3a}$ is ($C_2$-$C_9$heteroaryl)-CH$_2$— optionally substituted with 1 or 2 groups each independently selected from halo, $C_1$-$C_6$alkyl, $C_1$-$C_6$haloalkyl, and hydroxyl. In some embodiments is a compound of Formula (I), (Ia), (Ib), (II), (IIa), (IIb), (IIc), or a pharmaceutically acceptable salt, solvate, or stereoisomer thereof, wherein Q is —CH$_2$OCH$_2$— or —(CH$_2$)$_n$—. In some embodiments is a compound of Formula (I), (Ia), (Ib), (II), (IIa), (IIb), (IIc), or a pharmaceutically acceptable salt, solvate, or stereoisomer thereof, wherein Q is —(CH$_2$)$_n$—. In some embodiments is a compound of Formula (I), (Ia), (Ib), (II), (IIa), (IIb), (IIc), or a pharmaceutically acceptable salt, solvate, or stereoisomer thereof, wherein n is 2. In some embodiments is a compound of Formula (I), (Ia), (Ib), (II), (IIa), (IIb), (IIc), or a pharmaceutically acceptable salt, solvate, or stereoisomer thereof, wherein n is 1. In some embodiments is a compound of Formula (I), (Ia), (Ib), (II), (IIa), (IIb), (IIc), or a pharmaceutically acceptable salt, solvate, or stereoisomer thereof, wherein Q is —CH$_2$OCH$_2$—. In some embodiments is a compound of Formula (I), (Ia), (Ib), (II), (IIa), (IIb), (IIc), or a pharmaceutically acceptable salt, solvate, or stereoisomer thereof, wherein p is 0, 1, 2, or 3. In some embodiments is a compound of Formula (I), (Ia), (Ib), (II), (IIa), (IIb), (IIc), or a pharmaceutically acceptable salt, solvate, or stereoisomer thereof, wherein each $R^4$ is independently halo, $C_1$-$C_6$alkyl, or $C_1$-$C_6$haloalkyl. In some embodiments is a compound of Formula (I), (Ia), (Ib), (II), (IIa), (IIb), (IIc), or a pharmaceutically acceptable salt, solvate, or stereoisomer thereof, wherein p is 1. In some embodiments is a compound of Formula (I), (Ia), (Ib), (II), (IIa), (IIb), (IIc), or a pharmaceutically acceptable salt, solvate, or stereoisomer thereof, wherein p is 2. In some embodiments is a compound of Formula (I), (Ia), (Ib), (II), (IIa), (IIb), (IIc), or a pharmaceutically acceptable salt, solvate, or stereoisomer thereof, wherein p is 3. In some embodiments is a compound of Formula (I), (Ia), (Ib), (II), (IIa), (IIb), (IIc), or a pharmaceutically acceptable salt, solvate, or stereoisomer thereof, wherein p is 0. In some embodiments is a compound of Formula (I), (Ia), (Ib), (II), (IIa), (IIb), (IIc), or a pharmaceutically acceptable salt, solvate, or stereoisomer thereof, wherein q is 0, 1, or 2. In some embodiments is a compound of Formula (I), (Ia), (Ib), (II), (IIa), (IIb), (IIc), or a pharmaceutically acceptable salt, solvate, or stereoisomer thereof, wherein each $R^5$ is independently halo, $C_1$-$C_6$alkyl, or $C_1$-$C_6$haloalkyl. In some embodiments is a compound of Formula (I), (Ia), (Ib), (II), (IIa), (IIb), (IIc), or a pharmaceutically acceptable salt, solvate, or stereoisomer thereof, wherein q is 1. In some embodiments is a compound of Formula (I), (Ia), (Ib), (II), (IIa), (IIb), (IIc), or a pharmaceutically acceptable salt, solvate, or stereoisomer thereof, wherein q is 0. In some embodiments is a compound of Formula (I), (Ia), (Ib), (II), (IIa), (IIb), (IIc), or a pharmaceutically acceptable salt, solvate, or stereoisomer thereof, wherein k is 0.

In another aspect described herein is a pharmaceutical composition comprising a compound of Formula (I), (Ia), (Ib), (II), (IIa), (IIb), (IIc), or a pharmaceutically acceptable salt, solvate, or stereoisomer thereof, and a pharmaceutically acceptable carrier.

In another aspect described herein is a method of treating a disease, disorder, or condition in an individual comprising administering to the individual a therapeutically effective amount of a compound of Formula (I), (Ia), (Ib), (II), (IIa), (IIb), (IIc), or a pharmaceutically acceptable salt, solvate, or stereoisomer thereof, wherein the disease, disorder, or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4$^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

"Alkylene" and "alkylene chain" as used herein and unless otherwise indicated, refer to a straight or branched divalent hydrocarbon chain consisting solely of carbon and hydrogen, containing no unsaturation and having from one to eight or one to six carbon atoms, examples of which include methylene, ethylene, propylene, n-butylene and the like. The alkylene chain may be attached to the rest of the molecule through the replacement of any two hydrogen atoms within the chain.

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

"Alkenylene" or "alkenylene chain" as used herein and unless otherwise indicated, refers to a straight or branched chain unsaturated divalent group consisting solely of carbon and hydrogen atoms, having from two to eight carbon atoms, wherein the unsaturation is present only as double bonds and wherein the double bond can exist between any two carbon atoms in the chain, examples of which include ethenylene, prop-1-enylene, but-2-enylene and the like. The alkenylene chain may be attached to the rest of the molecule through the replacement of any two hydrogen atoms within the chain.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Alkynylene" or "alkynylene chain" as used herein and unless otherwise indicated, refers to a straight or branched chain unsaturated divalent group consisting solely of carbon and hydrogen atoms, having from two to eight carbon atoms, wherein the unsaturation is present only as triple bonds and wherein the triple bond can exist between any two carbon atoms in the chain, examples of which include ethynylene, prop-1-ynylene, but-2-ynylene, pent-1-ynylene, pent-3-ynylene and the like. The alkynylene chain may be attached to the rest of the molecule through the replacement of any two hydrogen atoms within the chain.

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

"Aralkyl" as used herein and unless otherwise indicated, refers to a monovalent alkyl group substituted with aryl. In certain embodiments, both alkyl and aryl may be optionally substituted with one or more substituents.

The term "aromatic" refers to a planar ring having a delocalized 7-electron system containing 4n+2π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl). "Aryl" as used herein and unless otherwise indicated, refers to a group of carbocylic ring system, including monocyclic, bicyclic, tricyclic, tetracyclic C$_6$-C$_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphthene, indene, and fluorene.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

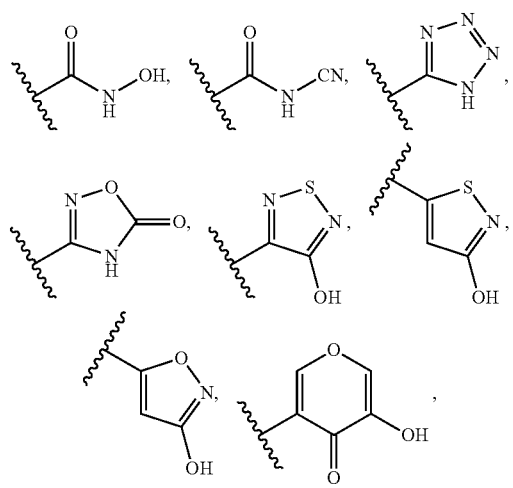

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). In some embodiments, cycloalkyl groups include groups having from 3 to 10 ring atoms. In some embodiments, cycloalkyl groups include groups having from 3 to 8 ring atoms. In some embodiments, cycloalkyl groups include groups having from 3 to 6 ring atoms.

"Cycloalkylalkyl" as used herein and unless otherwise indicated, refers to a monovalent alkyl group substituted with cycloalkyl. In certain embodiments, both alkyl and cycloalkyl may be optionally substituted with one or more substituents.

"Deuterium" as used herein and unless otherwise indicated, refers to the heavy isotope of hydrogen represented by the symbol D or $^2$H. As used herein, when a particular position in a compound is designated as having deuterium, it is understood that the compound is an isotopically enriched compound and the abundance of deuterium at that position in the compound is substantially greater than its natural abundance of 0.0156%.

"Deuterated" as applied to a chemical group and unless otherwise indicated, refers to a chemical group that is isotopically enriched with deuterium in an amount substantially greater than its natural abundance.

"Heteroaralkyl" as used herein and unless otherwise indicated, refers to a monovalent alkyl group substituted with heteroaryl. In certain embodiments, both alkyl and heteroaryl may be optionally substituted with one or more substituents.

"Heteroaryl" as used herein and unless otherwise indicated, refers to a 5- to 15-membered monocyclic aromatic ring or a multicyclic aromatic ring system wherein the ring or at least one ring of the multicyclic system contains one to five heteroatoms each independently selected from O, S, or N, with the remaining ring atoms being carbon atoms. Each ring of a heteroaryl group can contain up to two O atoms, up to two S atoms, and/or up to four N atoms, provided that the total number of heteroatoms in each ring is four or less and each ring contains at least one carbon atom. Examples of such heteroaryl groups include, but are not limited to, furanyl, pyrrolyl, thienyl, imidazolyl, pyrazolyl, oxazolyl, isoxazolyl, thiazolyl, isothiazolyl, triazolyl, oxadiazolyl, thiadiazolyl, tetrazolyl, pyrimidinyl, pyridinyl, pyridazinyl, pyrazinyl, benzimidazolyl, benzoisoxazolyl, benzopyranyl, benzothiadiazolyl, benzothiazolyl, pyridopyridyl, pyrrolopyridyl, quinolinyl, quinoxalinyl, quinazolinyl, naphthridinyl, 1,5-naphthyridinyl, 1,6-naphthyridinyl, thieno[3,2-b]pyridinyl, thieno[2,3-b]pyridinyl, 1H-pyrazolo[4,3-b]pyridinyl, 1H-pyrrolo[2,3-b]pyridinyl, 5H-pyrrolo[2,3-b]pyrazinyl, 1H-imidazo[4,5-b]pyrazinyl, 1H-pyrazolo[3,4-b]pyridinyl, thiadiazolopyrimidyl, and thienopyridyl.

"Heterocyclyl", as used herein and unless otherwise indicated, refers to a 3- to 15-membered monocyclic non-aromatic ring or a multicyclic ring system that contains at least one non-aromatic ring, wherein the ring or at least one ring contains one to five heteroatoms each independently selected from O, S, or N; and the remaining ring atoms being carbon atoms. In certain embodiments, the heterocyclyl is a monocyclic, bicyclic, tricyclic, or tetracyclic ring system, which may include a fused or bridged ring system, and in which the nitrogen or sulfur atoms may be optionally substituted with an oxo group or additionally with a second oxo group or an imino group, the nitrogen atoms may be optionally quaternized or substituted with, and some rings may be partially or fully saturated, or aromatic. In certain embodiments, the heterocyclyl is monocyclic, which may include a fused or bridged ring system, and in which the nitrogen or sulfur atoms may be optionally substituted with an oxo group or additionally with a second oxo group or an imino group, the nitrogen atoms may be optionally quaternized or substituted with, and some rings may be partially or fully saturated, or aromatic. The heterocyclyl may be attached to the main structure at any heteroatom or carbon atom which results in the creation of a stable compound. The heterocyclyl, when substituted, may be substituted at the carbon atom or the heteroatom.

Exemplary heterocylic radicals include, but are not limited to homopiperazinyl, morpholinyl, piperidinyl, piperazinyl, pyranyl, pyrrolidinyl, tetrahydrofuranyl, tetrahydropyranyl, ethylene oxide, oxetanyl, azetidinyl, quinuclidinyl, octahydroquinolizinyl, decahydroquinolizinyl, azabicyclo[3.2.1]octanyl, azabicyclo[2.2.2]octanyl, 6,7,8,9-tetrahydro-5H-pyrazino[2,3-b]indolyl.

"Heterocyclylalkyl" as used herein and unless otherwise indicated, refers to a monovalent alkyl group substituted with heterocyclyl. In certain embodiments, both alkyl and heterocyclyl may be optionally substituted with one or more substituents.

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

"Imino" as used herein and unless otherwise indicated, refers to the group =NH or =NR attached to a carbon or sulfur atom.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, alkenyl, cycloalkyl, aryl, heteroaryl (bonded through a ring carbon), and heterocyclyl.

The term "optionally substituted" or "substituted" means that the referenced group may be substituted with one or more additional group(s) individually and independently selected from alkyl, cycloalkyl, aryl, heteroaryl, heterocyclyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, and heterocyclyl. The protecting groups that may form the protective derivatives of the above substituents are found in sources such as Greene and Wuts, above.

"Oxo" as used herein refers to the group =O attached to a carbon or sulfur atom.

As used herein, the term "about" or "approximately" means within 20%, preferably within 10%, and more preferably within 5% of a given value or range.

The term a "therapeutically effective amount" as used herein refers to the amount of an RORγ modulator that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

RORγ Modulators

RORγ modulators contemplated for use in the compositions and methods described herein are compounds with RORγ modulator activities. The term "RORγ modulator" includes RORγ and/or RORγt agonists and inverse agonists.

In some embodiments, provided herein is a compound of Formula (I), or a pharmaceutically acceptable salt, solvate, or stereoisomer thereof:
wherein:

Formula (I)

(A)

is phenyl, or a 5-membered or 6-membered heteroaryl ring;

(B)

is phenyl, or a 5-membered or 6-membered heteroaryl ring;
Q is $-(CH_2)_n-$, $-CH_2YCH_2-$, or $-(CH_2)_mY-$, wherein $-(CH_2)_n-$, $-CH_2YCH_2-$, or $-(CH_2)_mY-$ is attached to the ring carbon atoms at a and b, c and d, a and c, or b and d;
X is $-N(R^{3a})-$, $-C(R^{3b})(R^{3c})-$, or $-O-$;
Y is $-O-$, $-S-$, or $-N(R^{3a})-$;
Z is $-(C(R^1)(R^2))_t-$;
each $R^1$ and each $R^2$ are each independently hydrogen, halo, or $C_1$-$C_6$alkyl;
each $R^3$ is independently selected from halo and $C_1$-$C_6$alkyl;
$R^{3a}$ is hydrogen, $C_1$-$C_6$alkyl, $C_1$-$C_6$haloalkyl, $C_2$-$C_9$heterocyclyl, $(C_2$-$C_9$heteroaryl$)$-$C_1$-$C_6$alkylene-, $-S(O)_2R^{10}$, $-C(O)R^{10}$, $-C(O)OR^{11}$, or $-C(O)N(R^{11})_2$, wherein $C_2$-$C_9$heteroaryl and $(C_2$-$C_9$heteroaryl$)$-$C_1$-$C_6$alkylene- are optionally substituted with 1 to 3 groups independently selected from halo, $C_1$-$C_6$alkyl, $C_1$-$C_6$haloalkyl, and hydroxyl;
$R^{3b}$ is hydrogen, halo, $C_1$-$C_6$alkyl, $C_1$-$C_6$haloalkyl, $-N(R^{11})S(O)_2R^{10}$, $-S(O)_2R^{10}$, $-C(O)R^{10}$, $-C(O)OR^{11}$, or $-C(O)N(R^{11})_2$;
$R^{3c}$ is hydrogen, halo, $C_1$-$C_6$alkyl, or $C_1$-$C_6$haloalkyl;
$R^{3d}$ is selected from hydrogen, $C_1$-$C_6$alkyl, $C_1$-$C_6$haloalkyl, $-S(O)_2R^8$, $-C(O)R^8$, $-C(O)OR^9$, and $-C(O)N(R^9)_2$;
each $R^4$ and each $R^5$ are each independently selected from halo, cyano, $C_1$-$C_6$alkyl, $C_1$-$C_6$haloalkyl, $C_1$-$C_6$alkoxy, $-N(R^7)_2$, $-C(O)R^6$, $-C(O)OR^7$, $-C(O)N(R^7)_2$, $-N(R^7)C(O)R^6$, $-N(R^7)SO_2R^6$, $-SO_2R^6$, and $-SO_2N(R^7)_2$;
each $R^6$ is independently $C_1$-$C_6$alkyl or $C_1$-$C_6$haloalkyl;
each $R^7$ is independently hydrogen, $C_1$-$C_6$alkyl, or $C_1$-$C_6$haloalkyl;
$R^8$ is $C_1$-$C_6$alkyl or $C_1$-$C_6$haloalkyl;
each $R^9$ is independently hydrogen, $C_1$-$C_6$alkyl, or $C_1$-$C_6$haloalkyl;
$R^{10}$ is $C_1$-$C_6$alkyl, $C_1$-$C_6$haloalkyl, $C_1$-$C_6$alkyl-O-$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or $(C_2$-$C_9$heteroaryl$)$-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or $(C_2$-$C_9$heteroaryl$)$-$C_1$-$C_6$alkylene- is optionally substituted with 1 to 3 groups selected from halo, $C_1$-$C_6$alkyl, $C_1$-$C_6$haloalkyl, and hydroxyl; each $R^{11}$ is independently hydrogen, $C_1$-$C_6$alkyl, or $C_1$-$C_6$haloalkyl;
k is 0, 1, 2, 3, or 4;
m is 1 or 2;
n is 1, 2, 3, or 4;
p is 0, 1, 2, 3, or 4;
q is 0, 1, 2, 3, or 4; and
t is 0, 1, 2, or 3.

In some embodiments is a compound of Formula (I), or a pharmaceutically acceptable salt, solvate, or stereoisomer thereof, wherein (A) and (B)

and are each independently phenyl or a 6-membered heteroaryl. In some embodiments is a compound of Formula (I), or a pharmaceutically acceptable salt, solvate, or stereoisomer thereof, wherein (A) and (B)

are each independently phenyl or a 5-membered heteroaryl. In some embodiments is a compound of Formula (I), or a pharmaceutically acceptable salt, solvate, or stereoisomer thereof, wherein (A) and (B)

are each independently selected from phenyl, pyridine, pyrimidine, pyrazine, pyridazine, pyrrole, imidazole, pyrazole, thiazole, isothiazole, oxazole, isoxazole, thiadiazole, triazole, oxadiazole, thiophene and furan. In some embodiments is a compound of Formula (I), or a pharmaceutically acceptable salt, solvate, or stereoisomer thereof, wherein (A) and (B)

are each independently selected from phenyl, pyridine, pyrimidine, pyrazine and pyridazine. In some embodiments is a compound of Formula (I), or a pharmaceutically acceptable salt, solvate, or stereoisomer thereof, wherein (A) and (B)

are both pyridine. In some embodiments is a compound of Formula (I), or a pharmaceutically acceptable salt solvate or stereoisomer thereof, wherein (A)

is selected from phenyl, pyridine, pyrimidine, pyrazine, and pyridazine and (B)

is phenyl or pyridine. In some embodiments is a compound of Formula (I), or a pharmaceutically acceptable salt, solvate, or stereoisomer thereof, wherein (A)

is selected from phenyl, pyridine, pyrimidine, pyrazine, and pyridazine and (B)

is phenyl. In some embodiments is a compound of Formula (I), or a pharmaceutically acceptable salt, solvate, or stereoisomer thereof, wherein (A)

is phenyl or pyridine and (B)

is phenyl. In some embodiments is a compound of Formula (I), or a pharmaceutically acceptable salt, solvate, or stereoisomer thereof, wherein (A) and (B)

are both phenyl. In some embodiments is a compound of Formula (I), or a pharmaceutically acceptable salt, solvate, or stereoisomer thereof, wherein (A)

is pyridine and (B)

is phenyl. In some embodiments is a compound of Formula (I), or a pharmaceutically acceptable salt, solvate, or stereoisomer thereof, wherein (A)

is phenyl and (B)

is pyridine.

In some embodiments, provided herein is a compound of Formula (I), or a pharmaceutically acceptable salt, solvate, or stereoisomer thereof, wherein each $R^1$ and each $R^2$ are each independently hydrogen or $C_1$-$C_6$alkyl. In some embodiments, provided herein is a compound of Formula (I), or a pharmaceutically acceptable salt, solvate, or stereoisomer thereof, wherein each $R^1$ and each $R^2$ are hydrogen. In some embodiments, provided herein is a compound of Formula (I), or a pharmaceutically acceptable salt, solvate, or stereoisomer thereof, wherein each $R^1$ and each $R^2$ are each independently $C_1$-$C_6$alkyl. In some embodiments, provided herein is a compound of Formula (I), or a pharmaceutically acceptable salt, solvate, or stereoisomer thereof, wherein each $R^1$ and each $R^2$ are —$CH_3$. In some embodiments, provided herein is a compound of Formula (I), or a pharmaceutically acceptable salt, solvate, or stereoisomer thereof, wherein each $R^1$ and each $R^2$ are each independently halo.

In some embodiments, provided herein is a compound of Formula (I), or a pharmaceutically acceptable salt, solvate, or stereoisomer thereof, wherein t is 0. In some embodiments, provided herein is a compound of Formula (I), or a pharmaceutically acceptable salt, solvate, or stereoisomer thereof, wherein t is 1. In some embodiments, provided herein is a compound of Formula (I), or a pharmaceutically acceptable salt, solvate, or stereoisomer thereof, wherein t is 2. In some embodiments, provided herein is a compound of Formula (I), or a pharmaceutically acceptable salt, solvate, or stereoisomer thereof, wherein t is 3.

In some embodiments, provided herein is a compound of Formula (I), or a pharmaceutically acceptable salt, solvate, or stereoisomer thereof, wherein Z is —$CH_2$—. In some embodiments, provided herein is a compound of Formula (I), or a pharmaceutically acceptable salt, solvate, or stereoisomer thereof, wherein Z is —$CH_2CH_2$—. In some embodiments, provided herein is a compound of Formula (I), or a pharmaceutically acceptable salt, solvate, or stereoisomer thereof, wherein Z is —$CH_2CH_2CH_2$—.

In some embodiments is a compound of Formula (I), or a pharmaceutically acceptable salt, solvate, or stereoisomer thereof, wherein Q is —$(CH_2)_n$—. In some embodiments is a compound of Formula (I), or a pharmaceutically acceptable salt, solvate, or stereoisomer thereof, wherein Q is —$CH_2$—. In some embodiments is a compound of Formula (I), or a pharmaceutically acceptable salt, solvate, or stereoisomer thereof, wherein Q is —CH$_2$CH$_2$—. In some embodiments is a compound of Formula (I), or a pharmaceutically acceptable salt, solvate, or stereoisomer thereof, wherein Q is —CH$_2$CH$_2$CH$_2$—. In some embodiments is a compound of Formula (I), or a pharmaceutically acceptable salt, solvate, or stereoisomer thereof, wherein Q is —CH$_2$CH$_2$CH$_2$CH$_2$—. In some embodiments is a compound of Formula (I), or a pharmaceutically acceptable salt, solvate, or stereoisomer thereof, wherein Q is —CH$_2$YCH$_2$—. In some embodiments is a compound of Formula (I), or a pharmaceutically acceptable salt, solvate, or stereoisomer thereof, wherein Q is —CH$_2$OCH$_2$—. In some embodiments is a compound of Formula (I), or a pharmaceutically acceptable salt, solvate, or stereoisomer thereof, wherein Q is —CH$_2$N(R$^{3d}$)CH$_2$—. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, —C(O)R$^8$, —C(O)OR$^9$, and —C(O)N(R$^9$)$_2$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, and —C(O)R$^8$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is hydrogen. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is C$_1$-C$_6$alkyl. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is —CH$_3$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is —S(O)$_2$R$^8$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is —S(O)$_2$CH$_3$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is —C(O)R$^8$. In some embodiments is a compound of Formula (I), or a pharmaceutically acceptable salt, solvate, or stereoisomer thereof, wherein Q is —CH$_2$N(R$^{3d}$)CH$_2$— and R$^{3d}$ is —C(O)CH$_3$. In some embodiments is a compound of Formula (I), or a pharmaceutically acceptable salt, solvate, or stereoisomer thereof, wherein Q is —CH$_2$SCH$_2$—. In some embodiments is a compound of Formula (I), or a pharmaceutically acceptable salt, solvate, or stereoisomer thereof, wherein Q is —(CH$_2$)$_m$Y—. In some embodiments is a compound of Formula (I), or a pharmaceutically acceptable salt, solvate, or stereoisomer thereof, wherein Q is —(CH$_2$)$_m$Y— and Y is —O—. In some embodiments is a compound of Formula (I), or a pharmaceutically acceptable salt, solvate, or stereoisomer thereof, wherein Q is —CH$_2$O—. In some embodiments is a compound of Formula (I), or a pharmaceutically acceptable salt, solvate, or stereoisomer thereof, wherein Q is —CH$_2$CH$_2$O—. In some embodiments is a compound of Formula (I), or a pharmaceutically acceptable salt, solvate, or stereoisomer thereof, wherein Q is —CH$_2$CH$_2$CH$_2$—. In some embodiments is a compound of Formula (I), or a pharmaceutically acceptable salt, solvate, or stereoisomer thereof, wherein Q is —(CH$_2$)$_m$Y— and Y is —N(R$^{3d}$). In some embodiments is a compound of Formula (I), or a pharmaceutically acceptable salt, solvate, or stereoisomer thereof, wherein Q is —(CH$_2$)$_m$Y—, Y is —N(R$^{3d}$)—, and R$^{3d}$ is hydrogen. In some embodiments is a compound of Formula (I), or a pharmaceutically acceptable salt, solvate, or stereoisomer thereof, wherein Q is —(CH$_2$)$_m$Y—, Y is —N(R$^{3d}$)—, and R$^{3d}$ is C$_1$-C$_6$alkyl. In some embodiments is a compound of Formula (I), or a pharmaceutically acceptable salt, solvate, or stereoisomer thereof, wherein Q is —(CH$_2$)$_m$Y— and Y is —S—.

In some embodiments is a compound of Formula (I), or a pharmaceutically acceptable salt, solvate, or stereoisomer thereof, wherein Q is attached to the ring carbon atoms at a and b. In some embodiments is a compound of Formula (I), or a pharmaceutically acceptable salt, solvate, or stereoisomer thereof, wherein Q is attached to the ring carbon atoms at c and d. In some embodiments is a compound of Formula (I), or a pharmaceutically acceptable salt, solvate, or stereoisomer thereof, wherein Q is attached to the ring carbon atoms at a and c. In some embodiments is a compound of Formula (I), or a pharmaceutically acceptable salt, solvate, or stereoisomer thereof, wherein Q is attached to the ring carbon atoms at b and d.

In some embodiments is a compound of Formula (I), or a pharmaceutically acceptable salt, solvate, or stereoisomer thereof, wherein X is —N(R$^{3a}$)—. In some embodiments is a compound of Formula (I), or a pharmaceutically acceptable salt, solvate, or stereoisomer thereof, wherein X is —N(R$^{3a}$)— and R$^{3a}$ is C$_1$-C$_6$alkyl, C$_2$-C$_9$heteroaryl, (C$_2$-C$_9$heteroaryl)-C$_1$-C$_6$alkylene-, —S(O)$_2$R$^{10}$, —C(O)R$^{10}$, or —C(O)OR$^{11}$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl.

In some embodiments is a compound of Formula (I), or a pharmaceutically acceptable salt, solvate, or stereoisomer thereof, wherein X is —N(R$^{3a}$)— and R$^{3a}$ is C$_1$-C$_6$alkyl.

In some embodiments is a compound of Formula (I), or a pharmaceutically acceptable salt, solvate, or stereoisomer thereof, wherein X is —N(R$^{3a}$)— and R$^{3a}$ is C$_2$-C$_9$heteroaryl optionally substituted with 1 to 2 groups each independently selected from halo, C$_1$-C$_6$alkyl, C$_1$-C$_6$haloalkyl, and hydroxyl.

In some embodiments is a compound of Formula (I), or a pharmaceutically acceptable salt, solvate, or stereoisomer thereof, wherein X is —N(R$^{3a}$)— and R$^{3a}$ is (C$_2$-C$_9$heteroaryl)-C$_1$-C$_6$alkylene-optionally substituted with 1 to 2 groups each independently selected from halo, C$_1$-C$_6$alkyl, C$_1$-C$_6$haloalkyl, and hydroxyl. In some embodiments is a compound of Formula (I), or a pharmaceutically acceptable salt, solvate, or stereoisomer thereof, wherein X is —N(R$^{3a}$)— and R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl. In some embodiments is a compound of Formula (I), or a pharmaceutically acceptable salt, solvate, or stereoisomer thereof, wherein X is —N(R$^{3a}$)— and R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl. In some embodiments is a compound of Formula (I), or a pharmaceutically acceptable salt, solvate, or stereoisomer thereof, wherein X is —N(R$^{3a}$)— and R$^{3a}$ is (C$_2$-C$_9$heteroaryl)-CH$_2$— substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl.

In some embodiments is a compound of Formula (I), or a pharmaceutically acceptable salt, solvate, or stereoisomer thereof, wherein X is —N(R$^{3a}$)— and R$^{3a}$ is —S(O)$_2$R$^{10}$. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is $C_1$-$C_6$alkyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is —CH$_3$. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is —CH$_2$CH$_3$. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is —CH$_2$CH$_2$CH$_3$. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is $C_1$-$C_6$haloalkyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is —CF$_3$. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is $C_3$-$C_8$cycloalkyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is $C_6$-$C_{10}$aryl optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is phenyl optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is ($C_6$-$C_{10}$aryl)-$C_1$-$C_6$alkylene- optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —S(O)$_2R^{10}$, and $R^{10}$ is (phenyl)-CH$_2$— optionally substituted with 1 or 2 groups selected from halo, $C_1$-$C_6$alkyl, $C_1$-$C_6$haloalkyl, and hydroxyl.

In some embodiments is a compound of Formula (I), or a pharmaceutically acceptable salt, solvate, or stereoisomer thereof, wherein X is —N($R^{3a}$)— and $R^{3a}$ is —C(O)$R^{10}$. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_1$-$C_6$alkyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is —CH$_3$. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is —CH$_2$CH$_3$. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is —CH$_2$CH$_2$CH$_3$. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_1$-$C_6$alkyl-O—$C_1$-$C_6$alkyl-. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_3$-$C_8$cycloalkyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_2$-$C_9$heterocyclyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_2$-$C_9$heterocyclyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is $C_6$-$C_{10}$aryl optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is phenyl optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is ($C_6$-$C_{10}$aryl)-$C_1$-$C_6$alkylene- optionally substituted with 1 or 2 groups selected from halo, $C_1$-$C_6$alkyl, $C_1$-$C_6$haloalkyl, and hydroxyl. In some embodiments is a compound of Formula (I), or a pharmaceutically acceptable salt, solvate, or stereoisomer thereof, wherein X is —N($R^{3a}$)—, $R^{3a}$ is —C(O)$R^{10}$, and $R^{10}$ is (phenyl)-CH$_2$— optionally substituted with 1 or 2 groups selected from halo, $C_1$-$C_6$alkyl, $C_1$-$C_6$haloalkyl, and hydroxyl.

In some embodiments is a compound of Formula (I), or a pharmaceutically acceptable salt, solvate, or stereoisomer thereof, wherein X is —N($R^{3a}$)— and $R^{3a}$ is —C(O)O$R^{11}$. In some embodiments is a compound of Formula (I), or a pharmaceutically acceptable salt, solvate, or stereoisomer thereof, wherein X is —N($R^{3a}$)—, $R^{3a}$ is —C(O)O$R^{11}$, and $R^{11}$ is $C_1$-$C_6$alkyl. In some embodiments is a compound of Formula (I), or a pharmaceutically acceptable salt, solvate, or stereoisomer thereof, wherein X is —N($R^{3a}$)—, $R^{3a}$ is —C(O)O$R^{11}$, and $R^{11}$ is —CH$_3$. In some embodiments is a compound of Formula (I), or a pharmaceutically acceptable salt, solvate, or stereoisomer thereof, wherein X is —N($R^{3a}$)—, $R^{3a}$ is —C(O)O$R^{11}$, and $R^{11}$ is —CH$_2$CH$_3$. In some embodiments is a compound of Formula (I), or a pharmaceutically acceptable salt, solvate, or stereoisomer thereof, wherein X is —N($R^{3a}$)—, $R^{3a}$ is —C(O)O$R^{11}$, and $R^{11}$ is —CH$_2$CH$_2$CH$_3$.

In some embodiments is a compound of Formula (I), or a pharmaceutically acceptable salt, solvate, or stereoisomer thereof, wherein X is —C($R^{3b}$)($R^{3b}$)—. In some embodiments is a compound of Formula (I), or a pharmaceutically acceptable salt, solvate, or stereoisomer thereof, wherein X is —C($R^{3b}$)(H)—. In some embodiments is a compound of Formula (I), or a pharmaceutically acceptable salt, solvate, or stereoisomer thereof, wherein X is —C($R^{3b}$)(H)— and $R^{3b}$ is $C_1$-$C_6$alkyl, $C_1$-$C_6$haloalkyl, —N($R^{11}$)S(O)$_2$$R^{10}$, —S(O)$_2$$R^{10}$, —C(O)$R^{10}$, —C(O)O$R^{11}$, or —C(O)N($R^{11}$)$_2$. In some embodiments is a compound of Formula (I), or a pharmaceutically acceptable salt, solvate, or stereoisomer thereof, wherein X is —C($R^{3b}$)(H)— and $R^{3b}$ is —N($R^{11}$)S(O)$_2$$R^{10}$, —S(O)$_2$$R^{10}$, —C(O)$R^{10}$, —C(O)O$R^{11}$, or —C(O)N($R^{11}$)$_2$. In some embodiments is a compound of Formula (I), or a pharmaceutically acceptable salt, solvate, or stereoisomer thereof, wherein X is —C($R^3$)(H)— and $R^{3b}$ is —N($R^{11}$)S(O)$_2$$R^{10}$. In some embodiments is a compound of Formula (I), or a pharmaceutically acceptable salt, solvate, or stereoisomer thereof, wherein X is —C($R^3$)(H)— and $R^{3b}$ is —NHS(O)$_2$$R^{10}$. In some embodiments is a compound of Formula (I), or a pharmaceutically acceptable salt, solvate, or stereoisomer thereof, wherein X is —C($R^{3b}$)(H)— and $R^{3b}$ is —N(H)S(O)$_2$CH$_3$.

In some embodiments is a compound of Formula (I), or a pharmaceutically acceptable salt, solvate, or stereoisomer thereof, wherein X is —O—.

In some embodiments is a compound of Formula (I), or a pharmaceutically acceptable salt, solvate, or stereoisomer thereof, wherein p is 0, 1, 2, or 3. In some embodiments is a compound of Formula (I), or a pharmaceutically acceptable salt, solvate, or stereoisomer thereof, wherein p is 0. In some embodiments is a compound of Formula (I), or a pharmaceutically acceptable salt, solvate, or stereoisomer thereof, wherein p is 1. In some embodiments is a compound of Formula (I), or a pharmaceutically acceptable salt, solvate, or stereoisomer thereof, wherein p is 2. In some embodiments is a compound of Formula (I), or a pharmaceutically acceptable salt, solvate, or stereoisomer thereof, wherein p is 3. In some embodiments is a compound of Formula (I), or a pharmaceutically acceptable salt, solvate, or stereoisomer thereof, wherein p is 1, 2, or 3. In some embodiments is a compound of Formula (I), or a pharmaceutically acceptable salt, solvate, or stereoisomer thereof, wherein p is 1, 2, or 3 and each $R^4$ is independently halo, cyano, $C_1$-$C_6$alkyl, $C_1$-$C_6$haloalkyl, —C(O)$R^6$, —C(O)O$R^7$, or —C(O)N($R^7$)$_2$. In some embodiments is a compound of Formula (I), or a pharmaceutically acceptable salt, solvate, or stereoisomer thereof, wherein p is 1, 2, or 3 and each $R^4$ is independently halo, $C_1$-$C_6$alkyl, or $C_1$-$C_6$haloalkyl. In some embodiments is a compound of Formula (I), or a pharmaceutically acceptable salt, solvate, or stereoisomer thereof, wherein p is 1 and $R^4$ is halo, $C_1$-$C_6$alkyl, or $C_1$-$C_6$haloalkyl. In some embodiments is a compound of Formula (I), or a pharmaceutically acceptable salt, solvate, or stereoisomer thereof, wherein p is 2 and each $R^4$ is independently halo, $C_1$-$C_6$alkyl, or $C_1$-$C_6$haloalkyl. In some embodiments is a compound of Formula (I), or a pharmaceutically acceptable salt, solvate, or stereoisomer thereof, wherein p is 3 and each $R^4$ is independently halo, $C_1$-$C_6$alkyl, or $C_1$-$C_6$haloalkyl.

In some embodiments is a compound of Formula (I), or a pharmaceutically acceptable salt, solvate, or stereoisomer thereof, wherein q is 0, 1, 2, or 3. In some embodiments is a compound of Formula (I), or a pharmaceutically acceptable salt, solvate, or stereoisomer thereof, wherein q is 0. In some embodiments is a compound of Formula (I), or a pharmaceutically acceptable salt, solvate, or stereoisomer thereof, wherein q is 1. In some embodiments is a compound of Formula (I), or a pharmaceutically acceptable salt, solvate, or stereoisomer thereof, wherein q is 2. In some embodiments is a compound of Formula (I), or a pharmaceutically acceptable salt, solvate, or stereoisomer thereof, wherein q is 3. In some embodiments is a compound of Formula (I), or a pharmaceutically acceptable salt, solvate, or stereoisomer thereof, wherein q is 1, 2, or 3. In some embodiments is a compound of Formula (I), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, —C(O)$R^6$, —C(O)O$R^7$, or —C(O)N($R^7$)$_2$. In some embodiments is a compound of Formula (I), or a pharmaceutically acceptable salt, solvate, or stereoisomer thereof, wherein q is 1, 2, or 3 and each $R^5$ is independently halo, $C_1$-$C_6$alkyl, or $C_1$-$C_6$haloalkyl. In some embodiments is a compound of Formula (I), or a pharmaceutically acceptable salt, solvate, or stereoisomer thereof, wherein q is 1 and $R^5$ is halo, $C_1$-$C_6$alkyl, or $C_1$-$C_6$haloalkyl. In some embodiments is a compound of Formula (I), or a pharmaceutically acceptable salt, solvate, or stereoisomer thereof, wherein q is 2 and each $R^5$ is independently halo, $C_1$-$C_6$alkyl, or $C_1$-$C_6$haloalkyl. In some embodiments is a compound of Formula (I), or a pharmaceutically acceptable salt, solvate, or stereoisomer thereof, wherein q is 3 and each $R^5$ is independently halo, $C_1$-$C_6$alkyl, or $C_1$-$C_6$haloalkyl.

In some embodiments is a compound of Formula (I), or a pharmaceutically acceptable salt, solvate, or stereoisomer thereof, wherein k is 0, 1, 2, 3, or 4. In some embodiments is a compound of Formula (I), or a pharmaceutically acceptable salt, solvate, or stereoisomer thereof, wherein k is 0, 1, 2, or 3. In some embodiments is a compound of Formula (I), or a pharmaceutically acceptable salt, solvate, or stereoisomer thereof, wherein k is 0, 1, or 2. In some embodiments is a compound of Formula (I), or a pharmaceutically acceptable salt, solvate, or stereoisomer thereof, wherein k is 0 or 1. In some embodiments is a compound of Formula (I), or a pharmaceutically acceptable salt, solvate, or stereoisomer thereof, wherein k is 0. In some embodiments is a compound of Formula (I), or a pharmaceutically acceptable salt, solvate, or stereoisomer thereof, wherein k is 1. In some embodiments is a compound of Formula (I), or a pharmaceutically acceptable salt, solvate, or stereoisomer thereof, wherein k is 1 and $R^3$ is halo. In some embodiments is a compound of Formula (I), or a pharmaceutically acceptable salt, solvate, or stereoisomer thereof, wherein k is 1 and $R^3$ is $C_1$-$C_6$alkyl. In some embodiments is a compound of Formula (I), or a pharmaceutically acceptable salt, solvate, or stereoisomer thereof, wherein k is 1 and $R^3$ is —CH$_3$. In some embodiments is a compound of Formula (I), or a pharmaceutically acceptable salt, solvate, or stereoisomer thereof, wherein k is 2. In some embodiments is a compound of Formula (I), or a pharmaceutically acceptable salt, solvate, or stereoisomer thereof, wherein k is 2 and each $R^3$ is $C_1$-$C_6$alkyl. In some embodiments is a compound of Formula (I), or a pharmaceutically acceptable salt, solvate, or stereoisomer thereof, wherein k is 2 and each $R^3$ is —CH$_3$.

In some embodiments, provided herein is a compound of Formula (II), or a pharmaceutically acceptable salt, solvate, or stereoisomer thereof:

Formula (II)

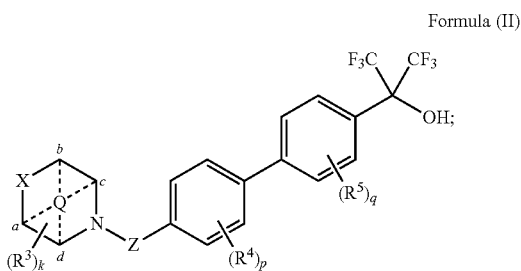

wherein:
Q is —(CH$_2$)$_n$—, —CH$_2$YCH$_2$—, or —(CH$_2$)$_m$Y—, wherein —(CH$_2$)$_n$—, —CH$_2$YCH$_2$—, or —(CH$_2$)$_m$Y— is attached to the ring carbon atoms at a and b, c and d, a and c, or b and d;
X is —N(R$^{3a}$)—, —C(R$^{3b}$)(R$^{3c}$)—, or —O—;
Y is —O—, —S—, or —N(R$^{3d}$)—;
Z is —(C(R$^1$)(R$^2$))$_t$—;
each R$^1$ and each R$^2$ are each independently hydrogen, halo, or C$_1$-C$_6$alkyl;
each R$^3$ is independently selected from halo and C$_1$-C$_6$alkyl;
R$^{3a}$ is hydrogen, C$_1$-C$_6$alkyl, C$_1$-C$_6$haloalkyl, C$_2$-C$_9$heteroaryl, (C$_2$-C$_9$heteroaryl)-C$_1$-C$_6$alkylene-, —S(O)$_2$R$^{10}$, —C(O)R$^{10}$, —C(O)OR$^{11}$, or —C(O)N(R$^{11}$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl;
R$^{3b}$ is hydrogen, halo, C$_1$-C$_6$alkyl, C$_1$-C$_6$haloalkyl, —N(R$^{11}$)S(O)$_2$R$^{10}$, —S(O)$_2$R$^{10}$, —C(O)R$^{10}$, —C(O)OR$^{11}$, or —C(O)N(R$^{11}$)$_2$;
R$^{3c}$ is hydrogen, halo, C$_1$-C$_6$alkyl, or C$_1$-C$_6$haloalkyl;
R$^{3d}$ is selected from hydrogen, C$_1$-C$_6$alkyl, C$_1$-C$_6$haloalkyl, —S(O)$_2$R$^8$, —C(O)R$^8$, —C(O)OR$^9$, and —C(O)N(R$^9$)$_2$;
each R$^4$ and each R$^5$ are each independently selected from halo, cyano, C$_1$-C$_6$alkyl, C$_1$-C$_6$haloalkyl, C$_1$-C$_6$alkoxy, —N(R$^7$)$_2$, —C(O)R$^6$, —C(O)OR$^7$, —C(O)N(R$^7$)$_2$, —N(R$^7$)C(O)R$^6$, —N(R$^7$)SO$_2$R$^6$, —SO$_2$R$^6$, and —SO$_2$N(R$^7$)$_2$;
each R$^6$ is independently C$_1$-C$_6$alkyl or C$_1$-C$_6$haloalkyl;
each R$^7$ is independently hydrogen, C$_1$-C$_6$alkyl, or C$_1$-C$_6$haloalkyl;
R$^8$ is C$_1$-C$_6$alkyl or C$_1$-C$_6$haloalkyl;
each R$^9$ is independently hydrogen, C$_1$-C$_6$alkyl, or C$_1$-C$_6$haloalkyl;
R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 to 3 groups selected from halo, C$_1$-C$_6$alkyl, C$_1$-C$_6$haloalkyl, and hydroxyl;
each R$^{11}$ is independently hydrogen, C$_1$-C$_6$alkyl, or C$_1$-C$_6$haloalkyl;
k is 0, 1, 2, 3, or 4;
m is 1 or 2;
n is 1, 2, 3, or 4;
p is 0, 1, 2, 3, or 4;
q is 0, 1, 2, 3, or 4; and
t is 0, 1, 2, or 3.

In some embodiments, provided herein is a compound of Formula (II), or a pharmaceutically acceptable salt, solvate, or stereoisomer thereof, wherein each R$^1$ and each R$^2$ are each independently hydrogen or C$_1$-C$_6$alkyl. In some embodiments, provided herein is a compound of Formula (II), or a pharmaceutically acceptable salt, solvate, or stereoisomer thereof, wherein each R$^1$ and each R$^2$ are hydrogen. In some embodiments, provided herein is a compound of Formula (II), or a pharmaceutically acceptable salt, solvate, or stereoisomer thereof, wherein each R$^1$ and each R$^2$ are each independently C$_1$-C$_6$alkyl. In some embodiments, provided herein is a compound of Formula (II), or a pharmaceutically acceptable salt, solvate, or stereoisomer thereof, wherein each R$^1$ and each R$^2$ are —CH$_3$. In some embodiments, provided herein is a compound of Formula (II), or a pharmaceutically acceptable salt, solvate, or stereoisomer thereof, wherein each R$^1$ and each R$^2$ are each independently halo.

In some embodiments, provided herein is a compound of Formula (II), or a pharmaceutically acceptable salt, solvate, or stereoisomer thereof, wherein t is 0. In some embodiments, provided herein is a compound of Formula (II), or a pharmaceutically acceptable salt, solvate, or stereoisomer thereof, wherein t is 1. In some embodiments, provided herein is a compound of Formula (II), or a pharmaceutically acceptable salt, solvate, or stereoisomer thereof, wherein t is 2. In some embodiments, provided herein is a compound of Formula (II), or a pharmaceutically acceptable salt, solvate, or stereoisomer thereof, wherein t is 3.

In some embodiments, provided herein is a compound of Formula (II), or a pharmaceutically acceptable salt, solvate, or stereoisomer thereof, wherein Z is —CH$_2$—. In some embodiments, provided herein is a compound of Formula (II), or a pharmaceutically acceptable salt, solvate, or stereoisomer thereof, wherein Z is —CH$_2$CH$_2$—. In some embodiments, provided herein is a compound of Formula (II), or a pharmaceutically acceptable salt, solvate, or stereoisomer thereof, wherein Z is —CH$_2$CH$_2$CH$_2$—.

In some embodiments is a compound of Formula (II), or a pharmaceutically acceptable salt, solvate, or stereoisomer thereof, wherein Q is —(CH$_2$)$_n$—. In some embodiments is a compound of Formula (II), or a pharmaceutically acceptable salt, solvate, or stereoisomer thereof, wherein Q is —CH$_2$—. In some embodiments is a compound of Formula (II), or a pharmaceutically acceptable salt, solvate, or stereoisomer thereof, wherein Q is —CH$_2$CH$_2$—. In some embodiments is a compound of Formula (II), or a pharmaceutically acceptable salt, solvate, or stereoisomer thereof, wherein Q is —CH$_2$CH$_2$CH$_2$—. In some embodiments is a compound of Formula (II), or a pharmaceutically acceptable salt, solvate, or stereoisomer thereof, wherein Q is —CH$_2$CH$_2$CH$_2$CH$_2$—. In some embodiments is a compound of Formula (II), or a pharmaceutically acceptable salt, solvate, or stereoisomer thereof, wherein Q is —CH$_2$YCH$_2$—. In some embodiments is a compound of Formula (II), or a pharmaceutically acceptable salt, solvate, or stereoisomer thereof, wherein Q is —CH$_2$OCH$_2$—. In some embodiments is a compound of Formula (II), or a pharmaceutically acceptable salt, solvate, or stereoisomer thereof, wherein Q is —CH$_2$N(R$^{3d}$)CH$_2$—. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, —C(O)R$^8$, —C(O)OR$^9$, and —C(O)N(R$^9$)$_2$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, and —C(O)R$^8$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is hydrogen. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is C$_1$-C$_6$alkyl. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is —CH$_3$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is —S(O)$_2$R$^8$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is —S(O)$_2$CH$_3$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is —C(O)R$^8$. In some embodiments is a compound of Formula (II), or a pharmaceutically acceptable salt, solvate, or stereoisomer thereof, wherein Q is —CH$_2$N(R$^{3d}$)CH$_2$— and R$^{3d}$ is —C(O)CH$_3$. In some embodiments is a compound of Formula (II), or a pharmaceutically acceptable salt, solvate, or stereoisomer thereof, wherein Q is —CH$_2$SCH$_2$—. In some embodiments is a compound of Formula (II), or a pharmaceutically acceptable salt, solvate, or stereoisomer thereof, wherein Q is —(CH$_2$)$_m$Y—. In some embodiments is a compound of Formula (II), or a pharmaceutically acceptable salt, solvate, or stereoisomer thereof, wherein Q is —(CH$_2$)$_m$Y— and Y is —O—. In some embodiments is a compound of Formula (II), or a pharmaceutically acceptable salt, solvate, or stereoisomer thereof, wherein Q is —CH$_2$O—. In some embodiments is a compound of Formula (II), or a pharmaceutically acceptable salt, solvate, or stereoisomer thereof, wherein Q is —CH$_2$CH$_2$O—. In some embodiments is a compound of Formula (II), or a pharmaceutically acceptable salt, solvate, or stereoisomer thereof, wherein Q is —CH$_2$CH$_2$CH$_2$—. In some embodiments is a compound of Formula (II), or a pharmaceutically acceptable salt, solvate, or stereoisomer thereof, wherein Q is —(CH$_2$)$_m$Y— and Y is —N(R$^{3d}$)—. In some embodiments is a compound of Formula (II), or a pharmaceutically acceptable salt, solvate, or stereoisomer thereof, wherein Q is —(CH$_2$)$_m$Y—, Y is —N(R$^{3d}$)—, and R$^{3d}$ is hydrogen. In some embodiments is a compound of Formula (II), or a pharmaceutically acceptable salt, solvate, or stereoisomer thereof, wherein Q is —(CH$_2$)$_m$Y—, Y is —N(R$^{3d}$)—, and R$^{3d}$ is C$_1$-C$_6$alkyl. In some embodiments is a compound of Formula (II), or a pharmaceutically acceptable salt, solvate, or stereoisomer thereof, wherein Q is —(CH$_2$)$_m$Y— and Y is —S—.

In some embodiments is a compound of Formula (II), or a pharmaceutically acceptable salt, solvate, or stereoisomer thereof, wherein Q is attached to the ring carbon atoms at a and b. In some embodiments is a compound of Formula (II), or a pharmaceutically acceptable salt, solvate, or stereoisomer thereof, wherein Q is attached to the ring carbon atoms at c and d. In some embodiments is a compound of Formula (II), or a pharmaceutically acceptable salt, solvate, or stereoisomer thereof, wherein Q is attached to the ring carbon atoms at a and c. In some embodiments is a compound of Formula (II), or a pharmaceutically acceptable salt, solvate, or stereoisomer thereof, wherein Q is attached to the ring carbon atoms at b and d.

In some embodiments is a compound of Formula (II), or a pharmaceutically acceptable salt, solvate, or stereoisomer thereof, wherein X is —N(R$^{3a}$)—. In some embodiments is a compound of Formula (II), or a pharmaceutically acceptable salt, solvate, or stereoisomer thereof, wherein X is —N(R$^{3a}$)— and R$^{3a}$ is C$_1$-C$_6$alkyl, C$_2$-C$_9$heteroaryl, (C$_2$-C$_9$heteroaryl)-C$_1$-C$_6$alkylene-, —S(O)$_2$R$^{10}$, —C(O)R$^{10}$, or —C(O)OR$^{11}$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl.

In some embodiments is a compound of Formula (II), or a pharmaceutically acceptable salt, solvate, or stereoisomer thereof, wherein X is —N(R$^{3a}$)— and R$^{3a}$ is C$_1$-C$_6$alkyl.

In some embodiments is a compound of Formula (II), or a pharmaceutically acceptable salt, solvate, or stereoisomer thereof, wherein X is —N(R$^{3a}$)— and R$^{3a}$ is C$_2$-C$_9$heteroaryl optionally substituted with 1 to 2 groups each independently selected from halo, C$_1$-C$_6$alkyl, C$_1$-C$_6$haloalkyl, and hydroxyl.

In some embodiments is a compound of Formula (II), or a pharmaceutically acceptable salt, solvate, or stereoisomer thereof, wherein X is —N(R$^{3a}$)— and R$^{3a}$ is (C$_2$-C$_9$heteroaryl)-C$_1$-C$_6$alkylene-optionally substituted with 1 to 2 groups each independently selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)— and R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)— and R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl. In some embodiments is a compound of Formula (II), or a pharmaceutically acceptable salt, solvate, or stereoisomer thereof, wherein X is —N(R$^{3a}$)— and R$^{3a}$ is (C$_2$-C$_9$heteroaryl)-CH$_2$— substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl.

In some embodiments is a compound of Formula (II), or a pharmaceutically acceptable salt, solvate, or stereoisomer thereof, wherein X is —N(R$^{3a}$)— and R$^{3a}$ is —S(O)$_2$R$^{10}$. In some embodiments is a compound of Formula (II), or a pharmaceutically acceptable salt, solvate, or stereoisomer thereof, wherein X is —N(R$^{3a}$), R$^{3a}$ is —S(O)$_2$R$^{10}$, and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is C$_1$-C$_6$alkyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is —CH$_3$. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is —CH$_2$CH$_3$. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is —CH$_2$CH$_2$CH$_3$. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is C$_1$-C$_6$haloalkyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is —CF$_3$. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is C$_3$-C$_8$cycloalkyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —S(O)$_2$R$^{10}$, and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (II), or a pharmaceutically acceptable salt, solvate, or stereoisomer thereof, wherein X is —N(R$^{3a}$)— and R$^{3a}$ is —C(O)R$^{10}$. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_1$-C$_6$alkyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is —CH$_3$. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is —CH$_2$CH$_3$. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is —CH$_2$CH$_2$CH$_3$. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_1$-C$_6$alkyl-O—C$_1$-C$_6$alkyl-. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_3$-C$_8$cycloalkyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_2$-C$_9$heterocyclyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_2$-C$_9$heterocyclyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (II), or a pharmaceutically acceptable salt, solvate, or stereoisomer thereof, wherein X is —N(R$^{3a}$)—, R$^{3a}$ is —C(O)R$^{10}$, and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (II), or a pharmaceutically acceptable salt, solvate, or stereoisomer thereof, wherein X is —N(R$^{3a}$)— and R$^{3a}$ is —C(O)OR$^{11}$. In some embodiments is a compound of Formula (II), or a pharmaceutically acceptable salt, solvate, or stereoisomer thereof, wherein X is —N(R$^{3a}$)—, R$^{3a}$ is —C(O)OR$^{11}$, and R$^{11}$ is C$_1$-C$_6$alkyl. In some embodiments is a compound of Formula (II), or a pharmaceutically acceptable salt, solvate, or stereoisomer thereof, wherein X is —N(R$^{3a}$)—, R$^{3a}$ is —C(O)OR$^{11}$, and R$^{11}$ is —CH$_3$. In some embodiments is a compound of Formula (II), or a pharmaceutically acceptable salt, solvate, or stereoisomer thereof, wherein X is —N(R$^{3a}$)—, R$^{3a}$ is —C(O)OR$^{11}$, and R$^{11}$ is —CH$_2$CH$_3$. In some embodiments is a compound of Formula (II), or a pharmaceutically acceptable salt, solvate, or stereoisomer thereof, wherein X is —N(R$^{3a}$)—, R$^{3a}$ is —C(O)OR$^{11}$, and R$^{11}$ is —CH$_2$CH$_2$CH$_3$.

In some embodiments is a compound of Formula (II), or a pharmaceutically acceptable salt, solvate, or stereoisomer thereof, wherein X is —C(R$^{3b}$)(R$^{3b}$)—. In some embodiments is a compound of Formula (II), or a pharmaceutically acceptable salt, solvate, or stereoisomer thereof, wherein X is —C(R$^{3b}$)(H)—. In some embodiments is a compound of Formula (II), or a pharmaceutically acceptable salt, solvate, or stereoisomer thereof, wherein X is —C(R$^{3b}$)(H)— and R$^{3b}$ is C$_1$-C$_6$alkyl, C$_1$-C$_6$haloalkyl, —N(R$^{11}$)S(O)$_2$R$^{10}$, —S(O)$_2$R$^{10}$, —C(O)R$^{10}$, —C(O)OR$^{11}$, or —C(O)N(R$^{11}$)$_2$. In some embodiments is a compound of Formula (II), or a pharmaceutically acceptable salt, solvate, or stereoisomer thereof, wherein X is —C(R$^{3b}$)(H)— and R$^{3b}$ is —N(R$^{11}$)S(O)$_2$R$^{10}$, —S(O)$_2$R$^{10}$, —C(O)R$^{10}$, —C(O)OR$^{11}$, or —C(O)N(R$^{11}$)$_2$. In some embodiments is a compound of Formula (II), or a pharmaceutically acceptable salt, solvate, or stereoisomer thereof, wherein X is —C(R$^3$)(H)— and R$^{3b}$ is —N(R$^{11}$)S(O)$_2$R$^{10}$. In some embodiments is a compound of Formula (II), or a pharmaceutically acceptable salt, solvate, or stereoisomer thereof, wherein X is —C(R³)(H)— and R$^{3b}$ is —NHS(O)$_2$R$^{10}$. In some embodiments is a compound of Formula (II), or a pharmaceutically acceptable salt, solvate, or stereoisomer thereof, wherein X is —C(R$^{3b}$)(H)— and R$^{3b}$ is —N(H)S(O)$_2$CH$_3$.

In some embodiments is a compound of Formula (II), or a pharmaceutically acceptable salt, solvate, or stereoisomer thereof, wherein X is —O—.

In some embodiments is a compound of Formula (II), or a pharmaceutically acceptable salt, solvate, or stereoisomer thereof, wherein p is 0, 1, 2, or 3. In some embodiments is a compound of Formula (II), or a pharmaceutically acceptable salt, solvate, or stereoisomer thereof, wherein p is 0. In some embodiments is a compound of Formula (II), or a pharmaceutically acceptable salt, solvate, or stereoisomer thereof, wherein p is 1. In some embodiments is a compound of Formula (II), or a pharmaceutically acceptable salt, solvate, or stereoisomer thereof, wherein p is 2. In some embodiments is a compound of Formula (II), or a pharmaceutically acceptable salt, solvate, or stereoisomer thereof, wherein p is 3. In some embodiments is a compound of Formula (II), or a pharmaceutically acceptable salt, solvate, or stereoisomer thereof, wherein p is 1, 2, or 3. In some embodiments is a compound of Formula (II), or a pharmaceutically acceptable salt, solvate, or stereoisomer thereof, wherein p is 1, 2, or 3 and each R$^4$ is independently halo, cyano, C$_1$-C$_6$alkyl, C$_1$-C$_6$haloalkyl, —C(O)R$^6$, —C(O)OR$^7$, or —C(O)N(R$^7$)$_2$. In some embodiments is a compound of Formula (II), or a pharmaceutically acceptable salt, solvate, or stereoisomer thereof, wherein p is 1, 2, or 3 and each R$^4$ is independently halo, C$_1$-C$_6$alkyl, or C$_1$-C$_6$haloalkyl. In some embodiments is a compound of Formula (II), or a pharmaceutically acceptable salt, solvate, or stereoisomer thereof, wherein p is 1 and R$^4$ is halo, C$_1$-C$_6$alkyl, or C$_1$-C$_6$haloalkyl. In some embodiments is a compound of Formula (II), or a pharmaceutically acceptable salt, solvate, or stereoisomer thereof, wherein p is 2 and each R$^4$ is independently halo, C$_1$-C$_6$alkyl, or C$_1$-C$_6$haloalkyl. In some embodiments is a compound of Formula (II), or a pharmaceutically acceptable salt, solvate, or stereoisomer thereof, wherein p is 3 and each R$^4$ is independently halo, C$_1$-C$_6$alkyl, or C$_1$-C$_6$haloalkyl.

In some embodiments is a compound of Formula (II), or a pharmaceutically acceptable salt, solvate, or stereoisomer thereof, wherein q is 0, 1, 2, or 3. In some embodiments is a compound of Formula (II), or a pharmaceutically acceptable salt, solvate, or stereoisomer thereof, wherein q is 0. In some embodiments is a compound of Formula (II), or a pharmaceutically acceptable salt, solvate, or stereoisomer thereof, wherein q is 1. In some embodiments is a compound of Formula (II), or a pharmaceutically acceptable salt, solvate, or stereoisomer thereof, wherein q is 2. In some embodiments is a compound of Formula (II), or a pharmaceutically acceptable salt, solvate, or stereoisomer thereof, wherein q is 3. In some embodiments is a compound of Formula (II), or a pharmaceutically acceptable salt, solvate, or stereoisomer thereof, wherein q is 1, 2, or 3. In some embodiments is a compound of Formula (II), or a pharmaceutically acceptable salt, solvate, or stereoisomer thereof, wherein q is 1, 2, or 3 and each R$^5$ is independently halo, cyano, C$_1$-C$_6$alkyl, C$_1$-C$_6$haloalkyl, —C(O)R$^6$, —C(O)OR$^7$, or —C(O)N(R$^7$)$_2$. In some embodiments is a compound of Formula (II), or a pharmaceutically acceptable salt, solvate, or stereoisomer thereof, wherein q is 1, 2, or 3 and each R$^5$ is independently halo, C$_1$-C$_6$alkyl, or C$_1$-C$_6$haloalkyl. In some embodiments is a compound of Formula (II), or a pharmaceutically acceptable salt, solvate, or stereoisomer thereof, wherein q is 1 and R$^5$ is halo, C$_1$-C$_6$alkyl, or C$_1$-C$_6$haloalkyl. In some embodiments is a compound of Formula (II), or a pharmaceutically acceptable salt, solvate, or stereoisomer thereof, wherein q is 2 and each R$^5$ is independently halo, C$_1$-C$_6$alkyl, or C$_1$-C$_6$haloalkyl. In some embodiments is a compound of Formula (II), or a pharmaceutically acceptable salt, solvate, or stereoisomer thereof, wherein q is 3 and each R$^5$ is independently halo, C$_1$-C$_6$alkyl, or C$_1$-C$_6$haloalkyl.

In some embodiments is a compound of Formula (II), or a pharmaceutically acceptable salt, solvate, or stereoisomer thereof, wherein k is 0, 1, 2, 3, or 4. In some embodiments is a compound of Formula (II), or a pharmaceutically acceptable salt, solvate, or stereoisomer thereof, wherein k is 0, 1, 2, or 3. In some embodiments is a compound of Formula (II), or a pharmaceutically acceptable salt, solvate, or stereoisomer thereof, wherein k is 0, 1, or 2. In some embodiments is a compound of Formula (II), or a pharmaceutically acceptable salt, solvate, or stereoisomer thereof, wherein k is 0 or 1. In some embodiments is a compound of Formula (II), or a pharmaceutically acceptable salt, solvate, or stereoisomer thereof, wherein k is 0. In some embodiments is a compound of Formula (II), or a pharmaceutically acceptable salt, solvate, or stereoisomer thereof, wherein k is 1. In some embodiments is a compound of Formula (II), or a pharmaceutically acceptable salt, solvate, or stereoisomer thereof, wherein k is 1 and R$^3$ is halo. In some embodiments is a compound of Formula (II), or a pharmaceutically acceptable salt, solvate, or stereoisomer thereof, wherein k is 1 and R$^3$ is C$_1$-C$_6$alkyl. In some embodiments is a compound of Formula (II), or a pharmaceutically acceptable salt, solvate, or stereoisomer thereof, wherein k is 1 and R$^3$ is —CH$_3$. In some embodiments is a compound of Formula (II), or a pharmaceutically acceptable salt, solvate, or stereoisomer thereof, wherein k is 2. In some embodiments is a compound of Formula (II), or a pharmaceutically acceptable salt, solvate, or stereoisomer thereof, wherein k is 2 and each R$^3$ is C$_1$-C$_6$alkyl. In some embodiments is a compound of Formula (II), or a pharmaceutically acceptable salt, solvate, or stereoisomer thereof, wherein k is 2 and each R$^3$ is —CH$_3$.

In some embodiments, provided herein is a compound of Formula (IIa), or a pharmaceutically acceptable salt, solvate, or stereoisomer thereof:

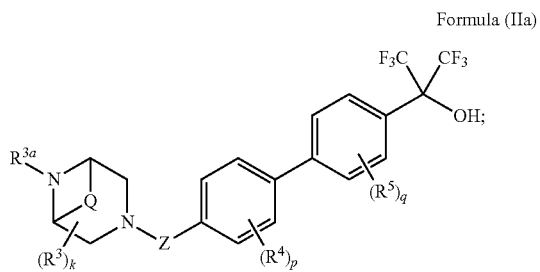

Formula (IIa)

wherein:
Q is —(CH$_2$)$_n$—, —CH$_2$YCH$_2$—, or —(CH$_2$)$_m$Y—;
Y is —O—, —S—, or —N(R$^{3d}$)—;
Z is —(C(R$^1$)(R$^2$))$_t$—;
each R$^1$ and each R$^2$ are each independently hydrogen, halo, or C$_1$-C$_6$alkyl;
each R$^3$ is independently selected from halo and C$_1$-C$_6$alkyl;

$R^{3a}$ is hydrogen, $C_1$-$C_6$alkyl, $C_1$-$C_6$haloalkyl, $C_2$-$C_9$heteroaryl, ($C_2$-$C_9$heteroaryl)-$C_1$-$C_6$alkylene-, —S(O)$_2$R$^{10}$, —C(O)R$^{10}$, —C(O)OR$^{11}$, or —C(O)N(R$^{11}$)$_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;

$R^{3d}$ is selected from hydrogen, $C_1$-$C_6$alkyl, $C_1$-$C_6$haloalkyl, —S(O)$_2$R$^8$, —C(O)R$^8$, —C(O)OR$^9$, and —C(O)N(R$^9$)$_2$;

each $R^4$ and each $R^5$ are each independently selected from halo, cyano, $C_1$-$C_6$alkyl, $C_1$-$C_6$haloalkyl, $C_1$-$C_6$alkoxy, —N(R$^7$)$_2$, —C(O)R$^6$, —C(O)OR$^7$, —C(O)N(R$^7$)$_2$, —N(R$^7$)C(O)R$^6$, —N(R$^7$)SO$_2$R$^6$, —SO$_2$R$^6$, and —SO$_2$N(R$^7$)$_2$;

each $R^6$ is independently $C_1$-$C_6$alkyl or $C_1$-$C_6$haloalkyl;

each $R^7$ is independently hydrogen, $C_1$-$C_6$alkyl, or $C_1$-$C_6$haloalkyl;

$R^8$ is $C_1$-$C_6$alkyl or $C_1$-$C_6$haloalkyl;

each $R^9$ is independently hydrogen, $C_1$-$C_6$alkyl, or $C_1$-$C_6$haloalkyl;

$R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl; each $R^{11}$ is independently hydrogen, $C_1$-$C_6$alkyl, or $C_1$-$C_6$haloalkyl;

k is 0, 1, 2, 3, or 4;

m is 1 or 2;

n is 1, 2, 3, or 4;

p is 0, 1, 2, 3, or 4;

q is 0, 1, 2, 3, or 4; and t is 0, 1, 2, or 3.

In some embodiments, provided herein is a compound of Formula (IIa), or a pharmaceutically acceptable salt, solvate, or stereoisomer thereof, wherein each $R^1$ and each $R^2$ are each independently hydrogen or $C_1$-$C_6$alkyl. In some embodiments, provided herein is a compound of Formula (IIa), or a pharmaceutically acceptable salt, solvate, or stereoisomer thereof, wherein each $R^1$ and each $R^2$ are hydrogen. In some embodiments, provided herein is a compound of Formula (IIa), or a pharmaceutically acceptable salt, solvate, or stereoisomer thereof, wherein each $R^1$ and each $R^2$ are each independently $C_1$-$C_6$alkyl. In some embodiments, provided herein is a compound of Formula (IIa), or a pharmaceutically acceptable salt, solvate, or stereoisomer thereof, wherein each $R^1$ and each $R^2$ are —CH$_3$. In some embodiments, provided herein is a compound of Formula (IIa), or a pharmaceutically acceptable salt, solvate, or stereoisomer thereof, wherein each $R^1$ and each $R^2$ are each independently halo.

In some embodiments, provided herein is a compound of Formula (IIa), or a pharmaceutically acceptable salt, solvate, or stereoisomer thereof, wherein t is 0. In some embodiments, provided herein is a compound of Formula (IIa), or a pharmaceutically acceptable salt, solvate, or stereoisomer thereof, wherein t is 1. In some embodiments, provided herein is a compound of Formula (IIa), or a pharmaceutically acceptable salt, solvate, or stereoisomer thereof, wherein t is 2. In some embodiments, provided herein is a compound of Formula (IIa), or a pharmaceutically acceptable salt, solvate, or stereoisomer thereof, wherein t is 3.

In some embodiments, provided herein is a compound of Formula (IIa), or a pharmaceutically acceptable salt, solvate, or stereoisomer thereof, wherein Z is —CH$_2$—. In some embodiments, provided herein is a compound of Formula (IIa), or a pharmaceutically acceptable salt, solvate, or stereoisomer thereof, wherein Z is —CH$_2$CH$_2$—. In some embodiments, provided herein is a compound of Formula (IIa), or a pharmaceutically acceptable salt, solvate, or stereoisomer thereof, wherein Z is —CH$_2$CH$_2$CH$_2$—.

In some embodiments is a compound of Formula (IIa), or a pharmaceutically acceptable salt, solvate, or stereoisomer thereof, wherein Q is —(CH$_2$)$_n$—. In some embodiments is a compound of Formula (IIa), or a pharmaceutically acceptable salt, solvate, or stereoisomer thereof, wherein Q is —CH$_2$—. In some embodiments is a compound of Formula (IIa), or a pharmaceutically acceptable salt, solvate, or stereoisomer thereof, wherein Q is —CH$_2$CH$_2$—. In some embodiments is a compound of Formula (IIa), or a pharmaceutically acceptable salt, solvate, or stereoisomer thereof, wherein Q is —CH$_2$CH$_2$CH$_2$—. In some embodiments is a compound of Formula (IIa), or a pharmaceutically acceptable salt, solvate, or stereoisomer thereof, wherein Q is —CH$_2$CH$_2$CH$_2$CH$_2$—.

In some embodiments is a compound of Formula (IIa), or a pharmaceutically acceptable salt, solvate, or stereoisomer thereof, wherein Q is —CH$_2$YCH$_2$—. In some embodiments is a compound of Formula (IIa), or a pharmaceutically acceptable salt, solvate, or stereoisomer thereof, wherein Q is —CH$_2$OCH$_2$—. In some embodiments is a compound of Formula (IIa), or a pharmaceutically acceptable salt, solvate, or stereoisomer thereof, wherein Q is —CH$_2$N(R$^{3d}$)CH$_2$—. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is selected from hydrogen, $C_1$-$C_6$alkyl, —S(O)$_2$R$^8$, —C(O)R$^8$, —C(O)OR$^9$, and —C(O)N(R$^9$)$_2$. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is selected from hydrogen, $C_1$-$C_6$alkyl, —S(O)$_2$R$^8$, and —C(O)R$^8$. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is hydrogen. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is $C_1$-$C_6$alkyl. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is —CH$_3$. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is —S(O)$_2$R$^8$. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is —S(O)$_2$CH$_3$. In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is —C(O)R$^8$.

In some embodiments is a compound of Formula (IIa), or a pharmaceutically acceptable salt, solvate, or stereoisomer thereof, wherein Q is —CH$_2$N(R$^{3d}$)CH$_2$— and $R^{3d}$ is —C(O)CH$_3$. In some embodiments is a compound of Formula (IIa), or a pharmaceutically acceptable salt, solvate, or stereoisomer thereof, wherein Q is —CH$_2$SCH$_2$—. In some embodiments is a compound of Formula (IIa), or a pharmaceutically acceptable salt, solvate, or stereoisomer thereof, wherein Q is —(CH$_2$)$_m$Y—. In some embodiments is a compound of Formula (IIa), or a pharmaceutically acceptable salt, solvate, or stereoisomer thereof, wherein Q is —(CH$_2$)$_m$Y— and Y is —O—. In some embodiments is a compound of Formula (IIa), or a pharmaceutically acceptable salt, solvate, or stereoisomer thereof, wherein Q is —CH$_2$O—. In some embodiments is a compound of Formula (IIa), or a pharmaceutically acceptable salt, solvate, or stereoisomer thereof, wherein Q is —CH$_2$CH$_2$O—. In some embodiments is a compound of Formula (IIa), or a pharmaceutically acceptable salt, solvate, or stereoisomer thereof, wherein Q is —CH$_2$CH$_2$CH$_2$O—. In some embodiments is a compound of Formula (IIa), or a pharmaceutically acceptable salt, solvate, or stereoisomer thereof, wherein Q is —(CH$_2$)$_m$Y— and Y is —N(R$^{3d}$)—. In some embodiments is a compound of Formula (IIa), or a pharmaceutically acceptable salt, solvate, or stereoisomer thereof, wherein Q is —(CH$_2$)$_m$Y—, Y is —N(R$^{3d}$)—, and R$^{3d}$ is hydrogen. In some embodiments is a compound of Formula (IIa), or a pharmaceutically acceptable salt, solvate, or stereoisomer thereof, wherein Q is —(CH$_2$)$_m$Y—, Y is —N(R$^{3d}$)—, and R$^{3d}$ is C$_1$-C$_6$alkyl. In some embodiments is a compound of Formula (IIa), or a pharmaceutically acceptable salt, solvate, or stereoisomer thereof, wherein Q is —(CH$_2$)$_m$Y— and Y is —S—.

In some embodiments is a compound of Formula (IIa), or a pharmaceutically acceptable salt, solvate, or stereoisomer thereof, wherein R$^{3a}$ is C$_1$-C$_6$alkyl, C$_2$-C$_9$heteroaryl, (C$_2$-C$_9$heteroaryl)-C$_1$-C$_6$alkylene-, —S(O)$_2$R$^{10}$, —C(O)R$^{10}$, or —C(O)OR$^{11}$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl.

In some embodiments is a compound of Formula (IIa), or a pharmaceutically acceptable salt, solvate, or stereoisomer thereof, wherein R$^{3a}$ is C$_1$-C$_6$alkyl.

In some embodiments is a compound of Formula (IIa), or a pharmaceutically acceptable salt, solvate, or stereoisomer thereof, wherein R$^{3a}$ is C$_2$-C$_9$heteroaryl optionally substituted with 1 to 2 groups each independently selected from halo, C$_1$-C$_6$alkyl, C$_1$-C$_6$haloalkyl, and hydroxyl.

In some embodiments is a compound of Formula (IIa), or a pharmaceutically acceptable salt, solvate, or stereoisomer thereof, wherein R$^{3a}$ is (C$_2$-C$_9$heteroaryl)-C$_1$-C$_6$alkylene- optionally substituted with 1 to 2 groups each independently selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl. In some embodiments is a compound of Formula (IIa), or a pharmaceutically acceptable salt, solvate, or stereoisomer thereof, wherein R$^{3a}$ is (C$_2$-C$_9$heteroaryl)-CH$_2$— substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl.

In some embodiments is a compound of Formula (IIa), or a pharmaceutically acceptable salt, solvate, or stereoisomer thereof, wherein R$^{3a}$ is —S(O)$_2$R$^{10}$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$alkyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_2$CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CH$_2$CH$_2$CH$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_1$-C$_6$haloalkyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is —CF$_3$. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_3$-C$_8$cycloalkyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —S(O)$_2$R$^{10}$ and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (IIa), or a pharmaceutically acceptable salt, solvate, or stereoisomer thereof, wherein R$^{3a}$ is —C(O)R$^{10}$. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_1$-C$_6$alkyl. In some embodiments is a compound of Formula (IIa), or a pharmaceutically acceptable salt, solvate, or stereoisomer thereof, wherein R$^{3a}$ is —C(O)R$^{10}$ and R$^{10}$ is —CH$_3$. In some embodiments is a compound of Formula (IIa), or a pharmaceutically acceptable salt, solvate, or stereoisomer thereof, wherein R$^{3a}$ is —C(O)R$^{10}$ and R$^{10}$ is —CH$_2$CH$_3$. In some embodiments is a compound of Formula (IIa), or a pharmaceutically acceptable salt, solvate, or stereoisomer thereof, wherein R$^{3a}$ is —C(O)R$^{10}$ and R$^{10}$ is —CH$_2$CH$_2$CH$_3$. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_1$-C$_6$alkyl-O—C$_1$-C$_6$alkyl-. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_3$-C$_8$cycloalkyl. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_2$-C$_9$heterocyclyl. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_2$-C$_9$heterocyclyl. In some embodiments is a compound of Formula (IIa), or a pharmaceutically acceptable salt, solvate, or stereoisomer thereof, wherein R$^{3a}$ is —C(O)R$^{10}$ and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —C(O)R$^{10}$ and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —C(O)R$^{10}$ and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (IIa), or a pharmaceutically acceptable salt, solvate, or stereoisomer thereof, wherein R$^{3a}$ is —C(O)R$^{10}$ and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (IIa), or a pharmaceutically acceptable salt, solvate, or stereoisomer thereof, wherein R$^{3a}$ is —C(O)OR$^{11}$. In some embodiments is a compound of Formula (IIa), or a pharmaceutically acceptable salt, solvate, or stereoisomer thereof, wherein R$^{3a}$ is —C(O)OR$^{11}$ and R$^{11}$ is C$_1$-C$_6$alkyl. In some embodiments is a compound of Formula (IIa), or a pharmaceutically acceptable salt, solvate, or stereoisomer thereof, wherein R$^{3a}$ is —C(O)OR$^{11}$ and R$^{11}$ is —CH$_3$. In some embodiments is a compound of Formula (IIa), or a pharmaceutically acceptable salt, solvate, or stereoisomer thereof, wherein R$^{3a}$ is —C(O)OR$^{11}$ and R$^{11}$ is —CH$_2$CH$_3$. In some embodiments is a compound of Formula (IIa), or a pharmaceutically acceptable salt, solvate, or stereoisomer thereof, wherein R$^{3a}$ is —C(O)OR$^{11}$ and R$^{11}$ is —CH$_2$CH$_2$CH$_3$.

In some embodiments is a compound of Formula (IIa), or a pharmaceutically acceptable salt, solvate, or stereoisomer thereof, wherein p is 0, 1, 2, or 3. In some embodiments is a compound of Formula (IIa), or a pharmaceutically acceptable salt, solvate, or stereoisomer thereof, wherein p is 0. In some embodiments is a compound of Formula (IIa), or a pharmaceutically acceptable salt, solvate, or stereoisomer thereof, wherein p is 1. In some embodiments is a compound of Formula (IIa), or a pharmaceutically acceptable salt, solvate, or stereoisomer thereof, wherein p is 2. In some embodiments is a compound of Formula (IIa), or a pharmaceutically acceptable salt, solvate, or stereoisomer thereof, wherein p is 3. In some embodiments is a compound of Formula (IIa), or a pharmaceutically acceptable salt, solvate, or stereoisomer thereof, wherein p is 1, 2, or 3. In some embodiments is a compound of Formula (IIa), or a pharmaceutically acceptable salt, solvate, or stereoisomer thereof, wherein p is 1, 2, or 3 and each R$^4$ is independently halo, cyano, C$_1$-C$_6$alkyl, C$_1$-C$_6$haloalkyl, —C(O)R$^6$, —C(O)R$^7$, or —C(O)N(R$^7$)$_2$. In some embodiments is a compound of Formula (IIa), or a pharmaceutically acceptable salt, solvate, or stereoisomer thereof, wherein p is 1, 2, or 3 and each R$^4$ is independently halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein p is 1 and R$^4$ is halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein p is 2 and each R$^4$ is independently halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein p is 3 and each R$^4$ is independently halo, C$_1$-C$_6$alkyl, or C$_1$-C$_6$haloalkyl.

In some embodiments is a compound of Formula (Ia), or a pharmaceutically acceptable salt, solvate, or stereoisomer thereof, wherein q is 0, 1, 2, or 3. In some embodiments is a compound of Formula (IIa), or a pharmaceutically acceptable salt, solvate, or stereoisomer thereof, wherein q is 0. In some embodiments is a compound of Formula (IIa), or a pharmaceutically acceptable salt, solvate, or stereoisomer thereof, wherein q is 1. In some embodiments is a compound of Formula (IIa), or a pharmaceutically acceptable salt, solvate, or stereoisomer thereof, wherein q is 2. In some embodiments is a compound of Formula (IIa), or a pharmaceutically acceptable salt, solvate, or stereoisomer thereof, wherein q is 3. In some embodiments is a compound of Formula (IIa), or a pharmaceutically acceptable salt, solvate, or stereoisomer thereof, wherein q is 1, 2, or 3. In some embodiments is a compound of Formula (IIa), or a pharmaceutically acceptable salt, solvate, or stereoisomer thereof, wherein q is 1, 2, or 3 and each R$^5$ is independently halo, cyano, C$_1$-C$_6$alkyl, C$_1$-C$_6$haloalkyl, —C(O)R$^6$, —C(O)OR$^7$, or —C(O)N(R$^7$)$_2$. In some embodiments is a compound of Formula (IIa), or a pharmaceutically acceptable salt, solvate, or stereoisomer thereof, wherein q is 1, 2, or 3 and each R$^5$ is independently halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein q is 1 and R is halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein q is 2 and each R$^5$ is independently halo, C$_1$-C$_6$alkyl, or C$_1$-C$_6$haloalkyl. In some embodiments is a compound of Formula (IIa), or a pharmaceutically acceptable salt, solvate, or stereoisomer thereof, wherein q is 3 and each R$^5$ is independently halo, C$_1$-C$_6$alkyl, or C$_1$-C$_6$haloalkyl.

In some embodiments is a compound of Formula (IIa), or a pharmaceutically acceptable salt, solvate, or stereoisomer thereof, wherein k is 0, 1, 2, 3, or 4. In some embodiments is a compound of Formula (IIa), or a pharmaceutically acceptable salt, solvate, or stereoisomer thereof, wherein k is 0, 1, 2, or 3. In some embodiments is a compound of Formula (IIa), or a pharmaceutically acceptable salt, solvate, or stereoisomer thereof, wherein k is 0, 1, or 2. In some embodiments is a compound of Formula (IIa), or a pharmaceutically acceptable salt, solvate, or stereoisomer thereof, wherein k is 0 or 1. In some embodiments is a compound of Formula (IIa), or a pharmaceutically acceptable salt, solvate, or stereoisomer thereof, wherein k is 0. In some embodiments is a compound of Formula (IIa), or a pharmaceutically acceptable salt, solvate, or stereoisomer thereof, wherein k is 1. In some embodiments is a compound of Formula (IIa), or a pharmaceutically acceptable salt, solvate, or stereoisomer thereof, wherein k is 1 and $R^3$ is halo. In some embodiments is a compound of Formula (IIa), or a pharmaceutically acceptable salt, solvate, or stereoisomer thereof, wherein k is 1 and $R^3$ is $C_1$-$C_6$alkyl. In some embodiments is a compound of Formula (IIa), or a pharmaceutically acceptable salt, solvate, or stereoisomer thereof, wherein k is 1 and $R^3$ is —$CH_3$. In some embodiments is a compound of Formula (IIa), or a pharmaceutically acceptable salt, solvate, or stereoisomer thereof, wherein k is 2. In some embodiments is a compound of Formula (IIa), or a pharmaceutically acceptable salt, solvate, or stereoisomer thereof, wherein k is 2 and each $R^3$ is $C_1$-$C_6$alkyl. In some embodiments is a compound of Formula (IIa), or a pharmaceutically acceptable salt, solvate, or stereoisomer thereof, wherein k is 2 and each $R^3$ is —$CH_3$.

In some embodiments, provided herein is a compound of Formula (IIb), or a pharmaceutically acceptable salt, solvate, or stereoisomer thereof:

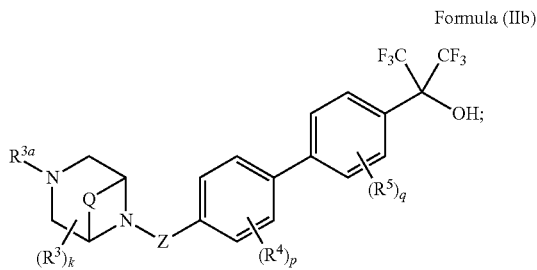

Formula (IIb)

wherein:
Q is —$(CH_2)_n$—, —$CH_2YCH_2$—, or —$(CH_2)_mY$—;
Y is —O—, —S—, or —$N(R^{3d})$—;
Z is —$(C(R^1)(R^2))_t$—;
each $R^1$ and each $R^2$ are each independently hydrogen, halo, or $C_1$-$C_6$alkyl;
each $R^3$ is independently selected from halo and $C_1$-$C_6$alkyl;
$R^{3a}$ is hydrogen, $C_1$-$C_6$alkyl, $C_1$-$C_6$haloalkyl, $C_2$-$C_9$heteroaryl, ($C_2$-$C_9$heteroaryl)-$C_1$-$C_6$alkylene-, —$S(O)_2R^{10}$, —$C(O)R^{10}$, —$C(O)OR^{11}$, or —$C(O)N(R^{11})_2$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl;
$R^{3d}$ is selected from hydrogen, $C_1$-$C_6$alkyl, $C_1$-$C_6$haloalkyl, —$S(O)_2R^8$, —$C(O)R^8$, —$C(O)OR^9$, and —$C(O)N(R^9)_2$;
each $R^4$ and each $R^5$ are each independently selected from halo, cyano, $C_1$-$C_6$alkyl, $C_1$-$C_6$haloalkyl, $C_1$-$C_6$alkoxy, —$N(R^7)_2$, —$C(O)R^6$, —$C(O)OR^7$, —$C(O)N(R^7)_2$, —$N(R^7)C(O)R^6$, —$N(R^7)SO_2R^6$, —$SO_2R^6$, and —$SO_2N(R^7)_2$;
each $R^6$ is independently $C_1$-$C_6$alkyl or $C_1$-$C_6$haloalkyl;
each $R^7$ is independently hydrogen, $C_1$-$C_6$alkyl, or $C_1$-$C_6$haloalkyl;

$R^8$ is $C_1$-$C_6$alkyl or $C_1$-$C_6$haloalkyl;
each $R^9$ is independently hydrogen, $C_1$-$C_6$alkyl, or $C_1$-$C_6$haloalkyl;
$R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 to 3 groups selected from halo, $C_1$-$C_6$alkyl, $C_1$-$C_6$haloalkyl, and hydroxyl;
each $R^{11}$ is independently hydrogen, $C_1$-$C_6$alkyl, or $C_1$-$C_6$haloalkyl;
k is 0, 1, 2, 3, or 4;
m is 1 or 2;
n is 1, 2, 3, or 4;
p is 0, 1, 2, 3, or 4;
q is 0, 1, 2, 3, or 4; and
t is 0, 1, 2, or 3.

In some embodiments, provided herein is a compound of Formula (IIb), or a pharmaceutically acceptable salt, solvate, or stereoisomer thereof, wherein each $R^1$ and each $R^2$ are each independently hydrogen or $C_1$-$C_6$alkyl. In some embodiments, provided herein is a compound of Formula (IIb), or a pharmaceutically acceptable salt, solvate, or stereoisomer thereof, wherein each $R^1$ and each $R^2$ are hydrogen. In some embodiments, provided herein is a compound of Formula (IIb), or a pharmaceutically acceptable salt, solvate, or stereoisomer thereof, wherein each $R^1$ and each $R^2$ are each independently $C_1$-$C_6$alkyl. In some embodiments, provided herein is a compound of Formula (IIb), or a pharmaceutically acceptable salt, solvate, or stereoisomer thereof, wherein each $R^1$ and each $R^2$ are —$CH_3$. In some embodiments, provided herein is a compound of Formula (IIb), or a pharmaceutically acceptable salt, solvate, or stereoisomer thereof, wherein each $R^1$ and each $R^2$ are each independently halo.

In some embodiments, provided herein is a compound of Formula (IIb), or a pharmaceutically acceptable salt, solvate, or stereoisomer thereof, wherein t is 0. In some embodiments, provided herein is a compound of Formula (IIb), or a pharmaceutically acceptable salt, solvate, or stereoisomer thereof, wherein t is 1. In some embodiments, provided herein is a compound of Formula (IIb), or a pharmaceutically acceptable salt, solvate, or stereoisomer thereof, wherein t is 2. In some embodiments, provided herein is a compound of Formula (IIb), or a pharmaceutically acceptable salt, solvate, or stereoisomer thereof, wherein t is 3.

In some embodiments, provided herein is a compound of Formula (IIb), or a pharmaceutically acceptable salt, solvate, or stereoisomer thereof, wherein Z is —$CH_2$—. In some embodiments, provided herein is a compound of Formula (IIb), or a pharmaceutically acceptable salt, solvate, or stereoisomer thereof, wherein Z is —$CH_2CH_2$—. In some embodiments, provided herein is a compound of Formula (IIb), or a pharmaceutically acceptable salt, solvate, or stereoisomer thereof, wherein Z is —$CH_2CH_2CH_2$—.

In some embodiments is a compound of Formula (IIb), or a pharmaceutically acceptable salt, solvate, or stereoisomer thereof, wherein Q is —$(CH_2)_n$—. In some embodiments is a compound of Formula (IIb), or a pharmaceutically acceptable salt, solvate, or stereoisomer thereof, wherein Q is —$CH_2$—. In some embodiments is a compound of Formula (IIb), or a pharmaceutically acceptable salt, solvate, or stereoisomer thereof, wherein Q is —$CH_2CH_2$—. In some embodiments is a compound of Formula (IIb), or a pharmaceutically acceptable salt, solvate, or stereoisomer thereof, wherein Q is —CH$_2$CH$_2$CH$_2$—. In some embodiments is a compound of Formula (IIb), or a pharmaceutically acceptable salt, solvate, or stereoisomer thereof, wherein Q is —CH$_2$CH$_2$CH$_2$CH$_2$—. In some embodiments is a compound of Formula (IIb), or a pharmaceutically acceptable salt, solvate, or stereoisomer thereof, wherein Q is —CH$_2$YCH$_2$—. In some embodiments is a compound of Formula (IIb), or a pharmaceutically acceptable salt, solvate, or stereoisomer thereof, wherein Q is —CH$_2$OCH$_2$—. In some embodiments is a compound of Formula (IIb), or a pharmaceutically acceptable salt, solvate, or stereoisomer thereof, wherein Q is —CH$_2$N(R$^{3d}$)CH$_2$—. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, —C(O)R$^8$, —C(O)OR$^9$, and —C(O)N(R$^9$)$_2$. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is selected from hydrogen, C$_1$-C$_6$alkyl, —S(O)$_2$R$^8$, and —C(O)R$^8$. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is hydrogen. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is C$_1$-C$_6$alkyl. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is —CH$_3$. In some embodiments is a compound of Formula (Ib), or a pharmaceutically acceptable salt, solvate, or stereoisomer thereof, wherein Q is —CH$_2$N(R$^{3d}$)CH$_2$— and R$^{3d}$ is —S(O)$_2$R$^8$. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is —S(O)$_2$CH$_3$. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is —C(O)R$^8$. In some embodiments is a compound of Formula (IIb), or a pharmaceutically acceptable salt, solvate, or stereoisomer thereof, wherein Q is —CH$_2$N(R$^{3d}$)CH$_2$— and R$^{3d}$ is —C(O)CH$_3$. In some embodiments is a compound of Formula (IIb), or a pharmaceutically acceptable salt, solvate, or stereoisomer thereof, wherein Q is —CH$_2$SCH$_2$—. In some embodiments is a compound of Formula (IIb), or a pharmaceutically acceptable salt, solvate, or stereoisomer thereof, wherein Q is —(CH$_2$)$_m$Y—. In some embodiments is a compound of Formula (IIb), or a pharmaceutically acceptable salt, solvate, or stereoisomer thereof, wherein Q is —(CH$_2$)$_m$Y— and Y is —O—. In some embodiments is a compound of Formula (IIb), or a pharmaceutically acceptable salt, solvate, or stereoisomer thereof, wherein Q is —CH$_2$O—. In some embodiments is a compound of Formula (Ib), or a pharmaceutically acceptable salt, solvate, or stereoisomer thereof, wherein Q is —CH$_2$CH$_2$O—. In some embodiments is a compound of Formula (IIb), or a pharmaceutically acceptable salt, solvate, or stereoisomer thereof, wherein Q is —CH$_2$CH$_2$CH$_2$O—. In some embodiments is a compound of Formula (IIb), or a pharmaceutically acceptable salt, solvate, or stereoisomer thereof, wherein Q is —(CH$_2$)$_m$Y— and Y is —N(R$^{3d}$)—. In some embodiments is a compound of Formula (Ib), or a pharmaceutically acceptable salt, solvate, or stereoisomer thereof, wherein Q is —(CH$_2$)$_m$Y—, Y is —N(R$^{3d}$)—, and R$^{3d}$ is hydrogen. In some embodiments is a compound of Formula (IIb), or a pharmaceutically acceptable salt, solvate, or stereoisomer thereof, wherein Q is —(CH$_2$)$_m$Y—, Y is —N(R$^{3d}$)—, and R$^{3d}$ is C$_1$-C$_6$alkyl. In some embodiments is a compound of Formula (Ib), or a pharmaceutically acceptable salt, solvate, or stereoisomer thereof, wherein Q is —(CH$_2$)$_m$Y— and Y is —S—.

In some embodiments is a compound of Formula (IIb), or a pharmaceutically acceptable salt, solvate, or stereoisomer thereof, wherein R$^{3a}$ is C$_1$-C$_6$alkyl, C$_2$-C$_9$heteroaryl, (C$_2$-C$_9$heteroaryl)-C$_1$-C$_6$alkylene-, —S(O)$_2$R$^{10}$, —C(O)R$^{10}$, or —C(O)OR$^{11}$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl.

In some embodiments is a compound of Formula (IIb), or a pharmaceutically acceptable salt, solvate, or stereoisomer thereof, wherein R$^{3a}$ is C$_1$-C$_6$alkyl.

In some embodiments is a compound of Formula (IIb), or a pharmaceutically acceptable salt, solvate, or stereoisomer thereof, wherein R$^{3a}$ is C$_2$-C$_9$heteroaryl optionally substituted with 1 to 2 groups each independently selected from halo, C$_1$-C$_6$alkyl, C$_1$-C$_6$haloalkyl, and hydroxyl.

In some embodiments is a compound of Formula (IIb), or a pharmaceutically acceptable salt, solvate, or stereoisomer thereof, wherein R$^{3a}$ is (C$_2$-C$_9$heteroaryl)-C$_1$-C$_6$alkylene- optionally substituted with 1 to 2 groups each independently selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein R$^{3a}$ is (C$_2$-C$_9$heteroaryl)-CH$_2$— optionally substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl. In some embodiments is a compound of Formula (IIb), or a pharmaceutically acceptable salt, solvate, or stereoisomer thereof, wherein R$^{3a}$ is (C$_2$-C$_9$heteroaryl)-CH$_2$— substituted with 1 to 2 groups each independently selected from halo, C$_1$-C$_6$alkyl, C$_1$-C$_6$haloalkyl, and hydroxyl, wherein the C$_2$-C$_9$heteroaryl is pyridyl.

In some embodiments is a compound of Formula (IIb), or a pharmaceutically acceptable salt, solvate, or stereoisomer thereof, wherein R$^{3a}$ is —S(O)$_2$R$^{10}$. In some embodiments is a compound of Formula (IIb), or a pharmaceutically acceptable salt, solvate, or stereoisomer thereof, wherein R$^{3a}$ is —S(O)$_2$R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein R$^{3a}$ is —S(O)$_2$R$^{10}$ and R$^{10}$ is C$_1$-C$_6$alkyl. In some embodiments is a compound of Formula (IIb), or a pharmaceutically acceptable salt, solvate, or stereoisomer thereof, wherein R$^{3a}$ is —S(O)$_2$R$^{10}$ and R$^{10}$ is —CH$_3$. In some embodiments is a compound of Formula (Ib), or a pharmaceutically acceptable salt, solvate, or stereoisomer thereof, wherein R$^{3a}$ is —S(O)$_2$R$^{10}$ and R$^{10}$ is —CH$_2$CH$_3$. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is —CH$_2$CH$_2$CH$_3$. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is C$_1$-C$_6$haloalkyl. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is —CF$_3$. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is C$_3$-C$_8$cycloalkyl. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein $R^{3a}$ is —S(O)$_2$R$^{10}$ and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (Ib), or a pharmaceutically acceptable salt, solvate, or stereoisomer thereof, wherein $R^{3a}$ is —S(O)$_2$R$^{10}$ and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (IIb), or a pharmaceutically acceptable salt, solvate, or stereoisomer thereof, wherein $R^{3a}$ is —C(O)R$^{10}$. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_1$-C$_6$alkyl. In some embodiments is a compound of Formula (IIb), or a pharmaceutically acceptable salt, solvate, or stereoisomer thereof, wherein $R^{3a}$ is —C(O)R$^{10}$ and R$^{10}$ is —CH$_3$. In some embodiments is a compound of Formula (IIb), or a pharmaceutically acceptable salt, solvate, or stereoisomer thereof, wherein $R^{3a}$ is —C(O)R$^{10}$ and R$^{10}$ is —CH$_2$CH$_3$. In some embodiments is a compound of Formula (IIb), or a pharmaceutically acceptable salt, solvate, or stereoisomer thereof, wherein $R^{3a}$ is —C(O)R$^{10}$ and R$^{10}$ is —CH$_2$CH$_2$CH$_3$. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_1$-C$_6$alkyl-O—C$_1$-C$_6$alkyl-. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_3$-C$_8$cycloalkyl. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_2$-C$_9$heterocyclyl. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_2$-C$_9$heterocyclyl. In some embodiments is a compound of Formula (IIb), or a pharmaceutically acceptable salt, solvate, or stereoisomer thereof, wherein $R^{3a}$ is —C(O)R$^{10}$ and R$^{10}$ is C$_6$-C$_{10}$aryl optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein $R^{3a}$ is —C(O)R$^{10}$ and R$^{10}$ is phenyl optionally substituted with 1 or 2 groups selected from halo, C$_1$-C$_6$alkyl, C$_1$-C$_6$haloalkyl, and hydroxyl. In some embodiments is a compound of Formula (IIb), or a pharmaceutically acceptable salt, solvate, or stereoisomer thereof, wherein $R^{3a}$ is —C(O)R$^{10}$ and R$^{10}$ is (C$_6$-C$_{10}$aryl)-C$_1$-C$_6$alkylene- optionally substituted with 1 or 2 groups selected from halo, C$_1$-C$_6$alkyl, C$_1$-C$_6$haloalkyl, and hydroxyl. In some embodiments is a compound of Formula (Ib), or a pharmaceutically acceptable salt, solvate, or stereoisomer thereof, wherein $R^{3a}$ is —C(O)R$^{10}$ and R$^{10}$ is (phenyl)-CH$_2$— optionally substituted with 1 or 2 groups selected from halo, C$_1$-C$_6$alkyl, C$_1$-C$_6$haloalkyl, and hydroxyl.

In some embodiments is a compound of Formula (IIb), or a pharmaceutically acceptable salt, solvate, or stereoisomer thereof, wherein $R^{3a}$ is —C(O)OR$^{11}$. In some embodiments is a compound of Formula (IIb), or a pharmaceutically acceptable salt, solvate, or stereoisomer thereof, wherein $R^{3a}$ is —C(O)OR$^{11}$ and R$^{11}$ is C$_1$-C$_6$alkyl. In some embodiments is a compound of Formula (IIb), or a pharmaceutically acceptable salt, solvate, or stereoisomer thereof, wherein $R^{3a}$ is —C(O)OR$^{11}$ and R$^{11}$ is —CH$_3$. In some embodiments is a compound of Formula (Ib), or a pharmaceutically acceptable salt, solvate, or stereoisomer thereof, wherein $R^{3a}$ is —C(O)OR$^{11}$ and R$^{11}$ is —CH$_2$CH$_3$. In some embodiments is a compound of Formula (IIb), or a pharmaceutically acceptable salt, solvate, or stereoisomer thereof, wherein $R^{3a}$ is —C(O)OR$^{11}$ and R$^{11}$ is —CH$_2$CH$_2$CH$_3$.

In some embodiments is a compound of Formula (IIb), or a pharmaceutically acceptable salt, solvate, or stereoisomer thereof, wherein p is 0, 1, 2, or 3. In some embodiments is a compound of Formula (IIb), or a pharmaceutically acceptable salt, solvate, or stereoisomer thereof, wherein p is 0. In some embodiments is a compound of Formula (IIb), or a pharmaceutically acceptable salt, solvate, or stereoisomer thereof, wherein p is 1. In some embodiments is a compound of Formula (IIb), or a pharmaceutically acceptable salt, solvate, or stereoisomer thereof, wherein p is 2. In some embodiments is a compound of Formula (IIb), or a pharmaceutically acceptable salt, solvate, or stereoisomer thereof, wherein p is 3. In some embodiments is a compound of Formula (IIb), or a pharmaceutically acceptable salt, solvate, or stereoisomer thereof, wherein p is 1, 2, or 3. In some embodiments is a compound of Formula (IIb), or a pharmaceutically acceptable salt, solvate, or stereoisomer thereof, wherein p is 1, 2, or 3 and each R$^4$ is independently halo, cyano, C$_1$-C$_6$alkyl, C$_1$-C$_6$haloalkyl, —C(O)R$^6$, —C(O)OR$^7$, or —C(O)N(R$^7$)$_2$. In some embodiments is a compound of Formula (IIb), or a pharmaceutically acceptable salt, solvate, or stereoisomer thereof, wherein p is 1, 2, or 3 and each R$^4$ is independently halo, C$_1$-C$_6$alkyl, or C$_1$-C$_6$haloalkyl. In some embodiments is a compound of Formula (Ib), or a pharmaceutically acceptable salt, solvate, or stereoisomer thereof, wherein p is 1 and R$^4$ is halo, C$_1$-C$_6$alkyl, or C$_1$-C$_6$haloalkyl. In some embodiments is a compound of Formula (IIb), or a pharmaceutically acceptable salt, solvate, or stereoisomer thereof, wherein p is 2 and each R$^4$ is independently halo, C$_1$-C$_6$alkyl, or C$_1$-C$_6$haloalkyl. In some embodiments is a compound of Formula (IIb), or a pharmaceutically acceptable salt, solvate, or stereoisomer thereof, wherein p is 3 and each R$^4$ is independently halo, C$_1$-C$_6$alkyl, or C$_1$-C$_6$haloalkyl.

In some embodiments is a compound of Formula (IIb), or a pharmaceutically acceptable salt, solvate, or stereoisomer thereof, wherein q is 0, 1, 2, or 3. In some embodiments is a compound of Formula (IIb), or a pharmaceutically acceptable salt, solvate, or stereoisomer thereof, wherein q is 0. In some embodiments is a compound of Formula (IIb), or a pharmaceutically acceptable salt, solvate, or stereoisomer thereof, wherein q is 1. In some embodiments is a compound of Formula (IIb), or a pharmaceutically acceptable salt, solvate, or stereoisomer thereof, wherein q is 2. In some embodiments is a compound of Formula (IIb), or a pharmaceutically acceptable salt, solvate, or stereoisomer thereof, wherein q is 3. In some embodiments is a compound of Formula (IIb), or a pharmaceutically acceptable salt, solvate, or stereoisomer thereof, wherein q is 1, 2, or 3. In some embodiments is a compound of Formula (IIb), or a pharmaceutically acceptable salt, solvate, or stereoisomer thereof, wherein q is 1, 2, or 3 and each R$^5$ is independently halo, cyano, C$_1$-C$_6$alkyl, C$_1$-C$_6$haloalkyl, —C(O)R$^6$, —C(O)OR$^7$, or —C(O)N(R$^7$)$_2$. In some embodiments is a compound of Formula (IIb), or a pharmaceutically acceptable salt, solvate, or stereoisomer thereof, wherein q is 1, 2, or 3 and each R$^5$ is independently halo, C$_1$-C$_6$alkyl, or C$_1$-C$_6$haloalkyl. In some embodiments is a compound of Formula (IIb), or a pharmaceutically acceptable salt, solvate, or stereoisomer thereof, wherein q is 1 and R$^5$ is halo, C$_1$-C$_6$alkyl, or C$_1$-C$_6$haloalkyl. In some embodiments is a compound of Formula (Ib), or a pharmaceutically acceptable salt, solvate, or stereoisomer thereof, wherein q is 2 and each R$^5$ is independently halo, C$_1$-C$_6$alkyl, or C$_1$-C$_6$haloalkyl. In some embodiments is a compound of Formula (IIb), or a pharmaceutically acceptable salt, solvate, or stereoisomer thereof, wherein q is 3 and each R$^5$ is independently halo, C$_1$-C$_6$alkyl, or C$_1$-C$_6$haloalkyl.

In some embodiments is a compound of Formula (IIb), or a pharmaceutically acceptable salt, solvate, or stereoisomer thereof, wherein k is 0, 1, 2, 3, or 4. In some embodiments is a compound of Formula (IIb), or a pharmaceutically acceptable salt, solvate, or stereoisomer thereof, wherein k is 0, 1, 2, or 3. In some embodiments is a compound of Formula (IIb), or a pharmaceutically acceptable salt, solvate, or stereoisomer thereof, wherein k is 0, 1, or 2. In some embodiments is a compound of Formula (IIb), or a pharmaceutically acceptable salt, solvate, or stereoisomer thereof, wherein k is 0 or 1. In some embodiments is a compound of Formula (IIb), or a pharmaceutically acceptable salt, solvate, or stereoisomer thereof, wherein k is 0. In some embodiments is a compound of Formula (IIb), or a pharmaceutically acceptable salt, solvate, or stereoisomer thereof, wherein k is 1. In some embodiments is a compound of Formula (Ib), or a pharmaceutically acceptable salt, solvate, or stereoisomer thereof, wherein k is 1 and R$^3$ is halo. In some embodiments is a compound of Formula (IIb), or a pharmaceutically acceptable salt, solvate, or stereoisomer thereof, wherein k is 1 and R$^3$ is C$_1$-C$_6$alkyl. In some embodiments is a compound of Formula (IIb), or a pharmaceutically acceptable salt, solvate, or stereoisomer thereof, wherein k is 1 and R$^3$ is —CH$_3$. In some embodiments is a compound of Formula (IIb), or a pharmaceutically acceptable salt, solvate, or stereoisomer thereof, wherein k is 2. In some embodiments is a compound of Formula (IIb), or a pharmaceutically acceptable salt, solvate, or stereoisomer thereof, wherein k is 2 and each R$^3$ is C$_1$-C$_6$alkyl. In some embodiments is a compound of Formula (Ib), or a pharmaceutically acceptable salt, solvate, or stereoisomer thereof, wherein k is 2 and each R$^3$ is —CH$_3$.

In some embodiments, provided herein is a compound of Formula (Ic), or a pharmaceutically acceptable salt, solvate, or stereoisomer thereof:

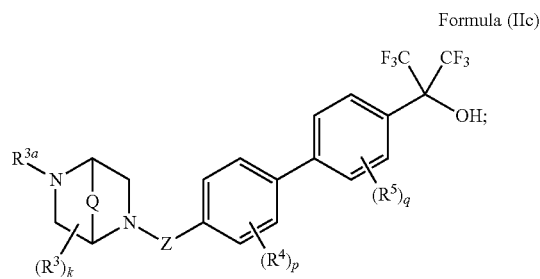

Formula (IIc)

wherein:
Q is —(CH$_2$)$_n$—, —CH$_2$YCH$_2$—, or —(CH$_2$)$_m$Y—;
Y is —O—, —S—, or —N(R$^{3d}$)—;
Z is —(C(R$^1$)(R$^2$))$_t$—;
each R$^1$ and each R$^2$ are each independently hydrogen, halo, or C$_1$-C$_6$alkyl;
each R$^3$ is independently selected from halo and C$_1$-C$_6$alkyl;
R$^{3a}$ is hydrogen, C$_1$-C$_6$alkyl, C$_1$-C$_6$haloalkyl, C$_2$-C$_9$heteroaryl, (C$_2$-C$_9$heteroaryl)-C$_1$-C$_6$alkylene-, —S(O)$_2$R$^{10}$, —C(O)R$^{10}$, —C(O)OR$^{11}$, or —C(O)N(R$^{11}$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl;
R$^{3d}$ is selected from hydrogen, C$_1$-C$_6$alkyl, C$_1$-C$_6$haloalkyl, —S(O)$_2$R$^8$, —C(O)R$^8$, —C(O)OR$^9$, and —C(O)N(R$^9$)$_2$;
each R$^4$ and each R$^5$ are each independently selected from halo, cyano, C$_1$-C$_6$alkyl, C$_1$-C$_6$haloalkyl, C$_1$-C$_6$alkoxy, —N(R$^7$)$_2$, —C(O)R$^6$, —C(O)OR$^7$, —C(O)N(R$^7$)$_2$, —N(R$^7$)C(O)R$^6$, —N(R$^7$)SO$_2$R$^6$, —SO$_2$R$^6$, and —SO$_2$N(R$^7$)$_2$;
each R$^6$ is independently C$_1$-C$_6$alkyl or C$_1$-C$_6$haloalkyl;
each R$^7$ is independently hydrogen, C$_1$-C$_6$alkyl, or C$_1$-C$_6$haloalkyl;
R$^8$ is C$_1$-C$_6$alkyl or C$_1$-C$_6$haloalkyl;
each R$^9$ is independently hydrogen, C$_1$-C$_6$alkyl, or C$_1$-C$_6$haloalkyl;
R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 to 3 groups selected from halo, C$_1$-C$_6$alkyl, C$_1$-C$_6$haloalkyl, and hydroxyl;
each R$^{11}$ is independently hydrogen, C$_1$-C$_6$alkyl, or C$_1$-C$_6$haloalkyl;
k is 0, 1, 2, 3, or 4;
m is 1 or 2;
n is 1, 2, 3, or 4;
p is 0, 1, 2, 3, or 4;

q is 0, 1, 2, 3, or 4; and t is 0, 1, 2, or 3.

In some embodiments, provided herein is a compound of Formula (IIc), or a pharmaceutically acceptable salt, solvate, or stereoisomer thereof, wherein each $R^1$ and each $R^2$ are each independently hydrogen or $C_1$-$C_6$alkyl. In some embodiments, provided herein is a compound of Formula (IIc), or a pharmaceutically acceptable salt, solvate, or stereoisomer thereof, wherein each $R^1$ and each $R^2$ are hydrogen. In some embodiments, provided herein is a compound of Formula (IIc), or a pharmaceutically acceptable salt, solvate, or stereoisomer thereof, wherein each $R^1$ and each $R^2$ are each independently $C_1$-$C_6$alkyl. In some embodiments, provided herein is a compound of Formula (IIc), or a pharmaceutically acceptable salt, solvate, or stereoisomer thereof, wherein each $R^1$ and each $R^2$ are —$CH_3$. In some embodiments, provided herein is a compound of Formula (IIc), or a pharmaceutically acceptable salt, solvate, or stereoisomer thereof, wherein each $R^1$ and each $R^2$ are each independently halo.

In some embodiments, provided herein is a compound of Formula (IIc), or a pharmaceutically acceptable salt, solvate, or stereoisomer thereof, wherein t is 0. In some embodiments, provided herein is a compound of Formula (IIc), or a pharmaceutically acceptable salt, solvate, or stereoisomer thereof, wherein t is 1. In some embodiments, provided herein is a compound of Formula (IIc), or a pharmaceutically acceptable salt, solvate, or stereoisomer thereof, wherein t is 2. In some embodiments, provided herein is a compound of Formula (IIc), or a pharmaceutically acceptable salt, solvate, or stereoisomer thereof, wherein t is 3.

In some embodiments, provided herein is a compound of Formula (IIc), or a pharmaceutically acceptable salt, solvate, or stereoisomer thereof, wherein Z is —$CH_2$—. In some embodiments, provided herein is a compound of Formula (IIc), or a pharmaceutically acceptable salt, solvate, or stereoisomer thereof, wherein Z is —$CH_2CH_2$—. In some embodiments, provided herein is a compound of Formula (IIc), or a pharmaceutically acceptable salt, solvate, or stereoisomer thereof, wherein Z is —$CH_2CH_2CH_2$—.

In some embodiments is a compound of Formula (IIc), or a pharmaceutically acceptable salt, solvate, or stereoisomer thereof, wherein Q is —$(CH_2)_n$—. In some embodiments is a compound of Formula (IIc), or a pharmaceutically acceptable salt, solvate, or stereoisomer thereof, wherein Q is —$CH_2$—. In some embodiments is a compound of Formula (IIc), or a pharmaceutically acceptable salt, solvate, or stereoisomer thereof, wherein Q is —$CH_2CH_2$—. In some embodiments is a compound of Formula (IIc), or a pharmaceutically acceptable salt, solvate, or stereoisomer thereof, wherein Q is —$CH_2CH_2CH_2$—. In some embodiments is a compound of Formula (IIc), or a pharmaceutically acceptable salt, solvate, or stereoisomer thereof, wherein Q is —$CH_2CH_2CH_2CH_2$—. In some embodiments is a compound of Formula (IIc), or a pharmaceutically acceptable salt, solvate, or stereoisomer thereof, wherein Q is —$CH_2YCH_2$—. In some embodiments is a compound of Formula (IIc), or a pharmaceutically acceptable salt, solvate, or stereoisomer thereof, wherein Q is —$CH_2OCH_2$—. In some embodiments is a compound of Formula (IIc), or a pharmaceutically acceptable salt, solvate, or stereoisomer thereof, wherein Q is —$CH_2N(R^{3d})CH_2$—. In some embodiments is a compound of Formula (IIc), or a pharmaceutically acceptable salt, solvate, or stereoisomer thereof, wherein Q is —$CH_2N(R^{3d})CH_2$— and $R^{3d}$ is selected from hydrogen, $C_1$-$C_6$alkyl, —$S(O)_2R^8$, —$C(O)R^8$, —$C(O)OR^9$, and —$C(O)N(R^9)_2$. In some embodiments is a compound of Formula (IIc), or a pharmaceutically acceptable salt, solvate, or stereoisomer thereof, wherein Q is —$CH_2N(R^{3d})CH_2$— and $R^{3d}$ is selected from hydrogen, $C_1$-$C_6$alkyl, —$S(O)_2R^8$, and —$C(O)R^8$. In some embodiments is a compound of Formula (IIc), or a pharmaceutically acceptable salt, solvate, or stereoisomer thereof, wherein Q is —$CH_2N(R^{3d})CH_2$— and $R^{3d}$ is hydrogen. In some embodiments is a compound of Formula (IIc), or a pharmaceutically acceptable salt, solvate, or stereoisomer thereof, wherein Q is —$CH_2N(R^{3d})CH_2$— and $R^{3d}$ is $C_1$-$C_6$alkyl. In some embodiments is a compound of Formula (IIc), or a pharmaceutically acceptable salt, solvate, or stereoisomer thereof, wherein Q is —$CH_2N(R^{3d})CH_2$— and $R^{3d}$ is —$CH_3$. In some embodiments is a compound of Formula (Ic), or a pharmaceutically acceptable salt, solvate, or stereoisomer thereof, wherein Q is —$CH_2N(R^{3d})CH_2$— and $R^{3d}$ is —$S(O)_2R^8$. In some embodiments is a compound of Formula (IIc), or a pharmaceutically acceptable salt, solvate, or stereoisomer thereof, wherein Q is —$CH_2N(R^{3d})CH_2$— and $R^{3d}$ is —$S(O)_2CH_3$. In some embodiments is a compound of Formula (IIc), or a pharmaceutically acceptable salt, solvate, or stereoisomer thereof, wherein Q is —$CH_2N(R^{3d})CH_2$— and $R^{3d}$ is —$C(O)R^8$. In some embodiments is a compound of Formula (IIc), or a pharmaceutically acceptable salt, solvate, or stereoisomer thereof, wherein Q is —$CH_2N(R^{3d})CH_2$— and $R^{3d}$ is —$C(O)CH_3$. In some embodiments is a compound of Formula (IIc), or a pharmaceutically acceptable salt, solvate, or stereoisomer thereof, wherein Q is —$CH_2SCH_2$—. In some embodiments is a compound of Formula (IIc), or a pharmaceutically acceptable salt, solvate, or stereoisomer thereof, wherein Q is —$(CH_2)_mY$—. In some embodiments is a compound of Formula (IIc), or a pharmaceutically acceptable salt, solvate, or stereoisomer thereof, wherein Q is —$(CH_2)_mY$— and Y is —O—. In some embodiments is a compound of Formula (IIc), or a pharmaceutically acceptable salt, solvate, or stereoisomer thereof, wherein Q is —$CH_2O$—. In some embodiments is a compound of Formula (Ic), or a pharmaceutically acceptable salt, solvate, or stereoisomer thereof, wherein Q is —$CH_2CH_2O$—. In some embodiments is a compound of Formula (IIc), or a pharmaceutically acceptable salt, solvate, or stereoisomer thereof, wherein Q is —$CH_2CH_2CH_2O$—. In some embodiments is a compound of Formula (IIc), or a pharmaceutically acceptable salt, solvate, or stereoisomer thereof, wherein Q is —$(CH_2)_mY$— and Y is —$N(R^{3d})$—. In some embodiments is a compound of Formula (Ic), or a pharmaceutically acceptable salt, solvate, or stereoisomer thereof, wherein Q is —$(CH_2)_mY$—, Y is —$N(R^{3d})$—, and $R^{3d}$ is hydrogen. In some embodiments is a compound of Formula (Ic), or a pharmaceutically acceptable salt, solvate, or stereoisomer thereof, wherein Q is —$(CH_2)_mY$—, Y is —$N(R^{3d})$—, and $R^{3d}$ is $C_1$-$C_6$alkyl. In some embodiments is a compound of Formula (IIc), or a pharmaceutically acceptable salt, solvate, or stereoisomer thereof, wherein Q is —$(CH_2)_mY$— and Y is —S—.

In some embodiments is a compound of Formula (IIc), or a pharmaceutically acceptable salt, solvate, or stereoisomer thereof, wherein $R^{3a}$ is $C_1$-$C_6$alkyl, $C_2$-$C_9$heteroaryl, ($C_2$-$C_9$heteroaryl)-$C_1$-$C_6$alkylene-, —$S(O)_2R^{10}$, —$C(O)R^{10}$, or —$C(O)OR^{11}$, wherein $C_2$-$C_9$heteroaryl and ($C_2$-$C_9$heteroaryl)-$C_1$-$C_6$alkylene- are optionally substituted with 1 to 3 groups independently selected from halo, $C_1$-$C_6$alkyl, $C_1$-$C_6$haloalkyl, and hydroxyl.

In some embodiments is a compound of Formula (IIc), or a pharmaceutically acceptable salt, solvate, or stereoisomer thereof, wherein $R^{3a}$ is $C_1$-$C_6$alkyl.

In some embodiments is a compound of Formula (IIc), or a pharmaceutically acceptable salt, solvate, or stereoisomer thereof, wherein $R^{3a}$ is $C_2$-$C_9$heteroaryl optionally substituted with 1 to 2 groups each independently selected from halo, $C_1$-$C_6$alkyl, $C_1$-$C_6$haloalkyl, and hydroxyl.

In some embodiments is a compound of Formula (IIc), or a pharmaceutically acceptable salt, solvate, or stereoisomer thereof, wherein $R^{3a}$ is ($C_2$-$C_9$heteroaryl)-$C_1$-$C_6$alkylene- optionally substituted with 1 to 2 groups each independently selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is ($C_2$-$C_9$heteroaryl)-$CH_2$— optionally substituted with 1 to 2 groups each independently selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is ($C_2$-$C_9$heteroaryl)-$CH_2$— optionally substituted with 1 to 2 groups each independently selected from halo, $C_1$-$C_6$alkyl, $C_1$-$C_6$haloalkyl, and hydroxyl, wherein the $C_2$-$C_9$heteroaryl is pyridyl. In some embodiments is a compound of Formula (IIc), or a pharmaceutically acceptable salt, solvate, or stereoisomer thereof, wherein $R^{3a}$ is ($C_2$-$C_9$heteroaryl)-$CH_2$— substituted with 1 to 2 groups each independently selected from halo, $C_1$-$C_6$alkyl, $C_1$-$C_6$haloalkyl, and hydroxyl, wherein the $C_2$-$C_9$heteroaryl is pyridyl.

In some embodiments is a compound of Formula (IIc), or a pharmaceutically acceptable salt, solvate, or stereoisomer thereof, wherein $R^{3a}$ is —$S(O)_2R^{10}$. In some embodiments is a compound of Formula (IIc), or a pharmaceutically acceptable salt, solvate, or stereoisomer thereof, wherein $R^{3a}$ is —$S(O)_2R^{10}$ and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 or 2 groups selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is $C_1$-$C_6$alkyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is —$CH_3$. In some embodiments is a compound of Formula (Ic), or a pharmaceutically acceptable salt, solvate, or stereoisomer thereof, wherein $R^{3a}$ is —$S(O)_2R^{10}$ and $R^{10}$ is —$CH_2CH_3$. In some embodiments is a compound of Formula (IIc), or a pharmaceutically acceptable salt, solvate, or stereoisomer thereof, wherein $R^{3a}$ is —$S(O)_2R^{10}$ and $R^{10}$ is —$CH_2CH_2CH_3$. In some embodiments is a compound of Formula (IIc), or a pharmaceutically acceptable salt, solvate, or stereoisomer thereof, wherein $R^{3a}$ is —$S(O)_2R^{10}$ and $R^{10}$ is $C_1$-$C_6$haloalkyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is —$CF_3$. In some embodiments is a compound of Formula (IIc), or a pharmaceutically acceptable salt, solvate, or stereoisomer thereof, wherein $R^{3a}$ is —$S(O)_2R^{10}$ and $R^{10}$ is $C_3$-$C_8$cycloalkyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is $C_6$-$C_{10}$aryl optionally substituted with 1 or 2 groups selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is phenyl optionally substituted with 1 or 2 groups selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is —$S(O)_2R^{10}$ and $R^{10}$ is ($C_6$-$C_{10}$aryl)-$C_1$-$C_6$alkylene- optionally substituted with 1 or 2 groups selected from halo, $C_1$-$C_6$alkyl, $C_1$-$C_6$haloalkyl, and hydroxyl. In some embodiments is a compound of Formula (Ic), or a pharmaceutically acceptable salt, solvate, or stereoisomer thereof, wherein $R^{3a}$ is —$S(O)_2R^{10}$ and $R^{10}$ is (phenyl)-$CH_2$— optionally substituted with 1 or 2 groups selected from halo, $C_1$-$C_6$alkyl, $C_1$-$C_6$haloalkyl, and hydroxyl.

In some embodiments is a compound of Formula (IIc), or a pharmaceutically acceptable salt, solvate, or stereoisomer thereof, wherein $R^{3a}$ is —$C(O)R^{10}$. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_1$-$C_6$alkyl, $C_1$-$C_6$haloalkyl, $C_1$-$C_6$alkyl-O—$C_1$-$C_6$alkyl-, $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene-, wherein the $C_3$-$C_8$cycloalkyl, $C_2$-$C_9$heterocyclyl, phenyl, (phenyl)-$C_1$-$C_6$alkylene-, $C_2$-$C_9$heteroaryl, or ($C_2$-$C_9$heteroaryl)-$C_1$-$C_6$alkylene- is optionally substituted with 1 or 2 groups selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_1$-$C_6$alkyl. In some embodiments is a compound of Formula (IIc), or a pharmaceutically acceptable salt, solvate, or stereoisomer thereof, wherein $R^{3a}$ is —$C(O)R^{10}$ and $R^{10}$ is —$CH_3$. In some embodiments is a compound of Formula (Ic), or a pharmaceutically acceptable salt, solvate, or stereoisomer thereof, wherein $R^{3a}$ is —$C(O)R^{10}$ and $R^{10}$ is —$CH_2CH_3$. In some embodiments is a compound of Formula (IIc), or a pharmaceutically acceptable salt, solvate, or stereoisomer thereof, wherein $R^{3a}$ is —$C(O)R^{10}$ and $R^{10}$ is —$CH_2CH_2CH_3$. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_1$-$C_6$alkyl-O—$C_1$-$C_6$alkyl-. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_3$-$C_8$cycloalkyl. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_2$-$C_9$heterocyclyl. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_2$-$C_9$heterocyclyl. In some embodiments is a compound of Formula (IIc), or a pharmaceutically acceptable salt, solvate, or stereoisomer thereof, wherein $R^{3a}$ is —$C(O)R^{10}$ and $R^{10}$ is $C_6$-$C_{10}$aryl optionally substituted with 1 or 2 groups selected from halo, $C_1$-$C_6$alkyl, $C_1$-$C_6$haloalkyl, and hydroxyl. In some embodiments is a compound of Formula (Ic), or a pharmaceutically acceptable salt, solvate, or stereoisomer thereof, wherein $R^{3a}$ is —$C(O)R^{10}$ and $R^{10}$ is phenyl optionally substituted with 1 or 2 groups selected from halo, $C_1$-$C_6$alkyl, $C_1$-$C_6$haloalkyl, and hydroxyl. In some embodiments is a compound of Formula (IIc), or a pharmaceutically acceptable salt, solvate, or stereoisomer thereof, wherein $R^{3a}$ is —$C(O)R^{10}$ and $R^{10}$ is ($C_6$-$C_{10}$aryl)-$C_1$-$C_6$alkylene- optionally substituted with 1 or 2 groups selected from halo, $C_1$-$C_6$alkyl, $C_1$-$C_6$haloalkyl, and hydroxyl. In some embodiments is a compound of Formula (Ic), or a pharmaceutically acceptable salt, solvate, or stereoisomer thereof, wherein $R^{3a}$ is —C(O)$R^{10}$ and $R^{10}$ is (phenyl)-CH$_2$— optionally substituted with 1 or 2 groups selected from halo, $C_1$-$C_6$alkyl, $C_1$-$C_6$haloalkyl, and hydroxyl.

In some embodiments is a compound of Formula (IIc), or a pharmaceutically acceptable salt, solvate, or stereoisomer thereof, wherein $R^{3a}$ is —C(O)O$R^{11}$. In some embodiments is a compound of Formula (IIc), or a pharmaceutically acceptable salt, solvate, or stereoisomer thereof, wherein $R^{3a}$ is —C(O)O$R^{11}$ and $R^{11}$ is $C_1$-$C_6$alkyl. In some embodiments is a compound of Formula (IIc), or a pharmaceutically acceptable salt, solvate, or stereoisomer thereof, wherein $R^{3a}$ is —C(O)O$R^{11}$ and $R^{11}$ is —CH$_3$. In some embodiments is a compound of Formula (IIc), or a pharmaceutically acceptable salt, solvate, or stereoisomer thereof, wherein $R^{3a}$ is —C(O)O$R^{11}$ and $R^{11}$ is —CH$_2$CH$_3$. In some embodiments is a compound of Formula (IIc), or a pharmaceutically acceptable salt, solvate, or stereoisomer thereof, wherein $R^{3a}$ is —C(O)O$R^{11}$ and $R^{11}$ is —CH$_2$CH$_2$CH$_3$.

In some embodiments is a compound of Formula (IIc), or a pharmaceutically acceptable salt, solvate, or stereoisomer thereof, wherein p is 0, 1, 2, or 3. In some embodiments is a compound of Formula (IIc), or a pharmaceutically acceptable salt, solvate, or stereoisomer thereof, wherein p is 0. In some embodiments is a compound of Formula (IIc), or a pharmaceutically acceptable salt, solvate, or stereoisomer thereof, wherein p is 1. In some embodiments is a compound of Formula (IIc), or a pharmaceutically acceptable salt, solvate, or stereoisomer thereof, wherein p is 2. In some embodiments is a compound of Formula (IIc), or a pharmaceutically acceptable salt, solvate, or stereoisomer thereof, wherein p is 3. In some embodiments is a compound of Formula (IIc), or a pharmaceutically acceptable salt, solvate, or stereoisomer thereof, wherein p is 1, 2, or 3. In some embodiments is a compound of Formula (IIc), or a pharmaceutically acceptable salt, solvate, or stereoisomer thereof, wherein p is 1, 2, or 3 and each $R^4$ is independently halo, cyano, $C_1$-$C_6$alkyl, $C_1$-$C_6$haloalkyl, —C(O)$R^6$, —C(O)O$R^7$, or —C(O)N($R^7$)$_2$. In some embodiments is a compound of Formula (IIc), or a pharmaceutically acceptable salt, solvate, or stereoisomer thereof, wherein p is 1, 2, or 3 and each $R^4$ is independently halo, $C_1$-$C_6$alkyl, or $C_1$-$C_6$haloalkyl. In some embodiments is a compound of Formula (Ic), or a pharmaceutically acceptable salt, solvate, or stereoisomer thereof, wherein p is 1 and $R^4$ is halo, $C_1$-$C_6$alkyl, or $C_1$-$C_6$haloalkyl. In some embodiments is a compound of Formula (Ic), or a pharmaceutically acceptable salt, solvate, or stereoisomer thereof, wherein p is 2 and each $R^4$ is independently halo, $C_1$-$C_6$alkyl, or $C_1$-$C_6$haloalkyl. In some embodiments is a compound of Formula (IIc), or a pharmaceutically acceptable salt, solvate, or stereoisomer thereof, wherein p is 3 and each $R^4$ is independently halo, $C_1$-$C_6$alkyl, or $C_1$-$C_6$haloalkyl.

In some embodiments is a compound of Formula (IIc), or a pharmaceutically acceptable salt, solvate, or stereoisomer thereof, wherein q is 0, 1, 2, or 3. In some embodiments is a compound of Formula (IIc), or a pharmaceutically acceptable salt, solvate, or stereoisomer thereof, wherein q is 0. In some embodiments is a compound of Formula (IIc), or a pharmaceutically acceptable salt, solvate, or stereoisomer thereof, wherein q is 1. In some embodiments is a compound of Formula (IIc), or a pharmaceutically acceptable salt, solvate, or stereoisomer thereof, wherein q is 2. In some embodiments is a compound of Formula (IIc), or a pharmaceutically acceptable salt, solvate, or stereoisomer thereof, wherein q is 3. In some embodiments is a compound of Formula (IIc), or a pharmaceutically acceptable salt, solvate, or stereoisomer thereof, wherein q is 1, 2, or 3. In some embodiments is a compound of Formula (IIc), or a pharmaceutically acceptable salt, solvate, or stereoisomer thereof, wherein q is 1, 2, or 3 and each $R^5$ is independently halo, cyano, $C_1$-$C_6$alkyl, $C_1$-$C_6$haloalkyl, —C(O)$R^6$, —C(O)$R^7$, or —C(O)N($R^7$)$_2$. In some embodiments is a compound of Formula (IIc), or a pharmaceutically acceptable salt, solvate, or stereoisomer thereof, wherein q is 1, 2, or 3 and each $R^5$ is independently halo, $C_1$-$C_6$alkyl, or $C_1$-$C_6$haloalkyl. In some embodiments is a compound of Formula (Ic), or a pharmaceutically acceptable salt, solvate, or stereoisomer thereof, wherein q is 1 and $R^5$ is halo, $C_1$-$C_6$alkyl, or $C_1$-$C_6$haloalkyl. In some embodiments is a compound of Formula (IIc), or a pharmaceutically acceptable salt, solvate, or stereoisomer thereof, wherein q is 2 and each $R^5$ is independently halo, $C_1$-$C_6$alkyl, or $C_1$-$C_6$haloalkyl. In some embodiments is a compound of Formula (IIc), or a pharmaceutically acceptable salt, solvate, or stereoisomer thereof, wherein q is 3 and each $R^5$ is independently halo, $C_1$-$C_6$alkyl, or $C_1$-$C_6$haloalkyl.

In some embodiments is a compound of Formula (IIc), or a pharmaceutically acceptable salt, solvate, or stereoisomer thereof, wherein k is 0, 1, 2, 3, or 4. In some embodiments is a compound of Formula (IIc), or a pharmaceutically acceptable salt, solvate, or stereoisomer thereof, wherein k is 0, 1, 2, or 3. In some embodiments is a compound of Formula (IIc), or a pharmaceutically acceptable salt, solvate, or stereoisomer thereof, wherein k is 0, 1, or 2. In some embodiments is a compound of Formula (IIc), or a pharmaceutically acceptable salt, solvate, or stereoisomer thereof, wherein k is 0 or 1. In some embodiments is a compound of Formula (IIc), or a pharmaceutically acceptable salt, solvate, or stereoisomer thereof, wherein k is 0. In some embodiments is a compound of Formula (IIc), or a pharmaceutically acceptable salt, solvate, or stereoisomer thereof, wherein k is 1. In some embodiments is a compound of Formula (Ic), or a pharmaceutically acceptable salt, solvate, or stereoisomer thereof, wherein k is 1 and $R^3$ is halo. In some embodiments is a compound of Formula (IIc), or a pharmaceutically acceptable salt, solvate, or stereoisomer thereof, wherein k is 1 and $R^3$ is $C_1$-$C_6$alkyl. In some embodiments is a compound of Formula (IIc), or a pharmaceutically acceptable salt, solvate, or stereoisomer thereof, wherein k is 1 and $R^3$ is —CH$_3$. In some embodiments is a compound of Formula (IIc), or a pharmaceutically acceptable salt, solvate, or stereoisomer thereof, wherein k is 2. In some embodiments is a compound of Formula (IIc), or a pharmaceutically acceptable salt, solvate, or stereoisomer thereof, wherein k is 2 and each $R^3$ is $C_1$-$C_6$alkyl. In some embodiments is a compound of Formula (IIc), or a pharmaceutically acceptable salt, solvate, or stereoisomer thereof, wherein k is 2 and each $R^3$ is —CH$_3$.

In some embodiments, provided herein is a compound selected from 2-(2'-ethyl-4'-(((1R,5S)-7-(methylsulfonyl)-3-oxa-7,9-diazabicyclo[3.3.1]nonan-9-yl)methyl)-[1,1'-biphenyl]-4-yl)-1,1,1,3,3,3-hexafluoropropan-2-ol;

2-(2'-ethyl-4'-(((1R,5S)-9-(methylsulfonyl)-3-oxa-7,9-diazabicyclo[3.3.1]nonan-7-yl)methyl)-[1,1'-biphenyl]-4-yl)-1,1,1,3,3,3-hexafluoropropan-2-ol;

2-(2-chloro-2'-ethyl-3',5'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-2,3',5'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-3',5'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(3-chloro-4-(4-ethyl-6-((8-(methylsulfonyl)-3,8-diazabicyclo[3.2.1]octan-3-yl)methyl)pyridin-3-yl)phenyl)-1,1,1,3,3,3-hexafluoropropan-2-ol;

2-(2-chloro-2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol;

2-(2-chloro-5'-fluoro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-2,6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-chloro-2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-chloro-2'-ethyl-5'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol;

1,1,1,3,3,3-hexafluoro-2-(5'-fluoro-2'-isopropyl-2-methyl-4'-((8-(methylsulfonyl)-3,8-diazabicyclo[3.2.1]octan-3-yl)methyl)-[1,1'-biphenyl]-4-yl)propan-2-ol;

2-(2-chloro-2'-isopropyl-4'-((3-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-chloro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-2,3',6'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-chloro-2'-ethyl-3',6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-2-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2,2'-diethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-ethyl-2'-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2-chloro-2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-3',5'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(6'-ethyl-2',3'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-3',6'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(4-(2-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol;

2-(4-(4-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol;

2'-ethyl-4-(1,1,1,3,3,3-hexafluoro-2-hydroxypropan-2-yl)-4'-((8-(methylsulfonyl)-3,8-diazabicyclo[3.2.1]octan-3-yl)methyl)-[1,1'-biphenyl]-2-carboxamide;

2-(6-(2-ethyl-4-((8-(methylsulfonyl)-3,8-diazabicyclo[3.2.1]octan-3-yl)methyl)phenyl)pyridin-3-yl)-1,1,1,3,3,3-hexafluoropropan-2-ol;

2-(4-(3-ethyl-5-((8-(methylsulfonyl)-3,8-diazabicyclo[3.2.1]octan-3-yl)methyl)pyridin-2-yl)-3-methylphenyl)-1,1,1,3,3,3-hexafluoropropan-2-ol;

1,1,1,3,3,3-hexafluoro-2-(3'-(8-(methylsulfonyl)-3,8-diazabicyclo[3.2.1]octan-3-yl)-[1,1'-biphenyl]-4-yl)propan-2-ol;

2-(2'-ethyl-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(2'-isopropyl-2-methyl-4'-((8-(methylsulfonyl)-3,8-diazabicyclo[3.2.1]octan-3-yl)methyl)-[1,1'-biphenyl]-4-yl)propan-2-ol;

2-(4'-((8-(5-(tert-butyl)-1,2,4-oxadiazol-3-yl)-3,8-diazabicyclo[3.2.1]octan-3-yl)methyl)-2'-methyl-[1,1'-biphenyl]-4-yl)-1,1,1,3,3,3-hexafluoropropan-2-ol;

2-(2'-ethyl-4'-((5-(methylsulfonyl)-2,5-diazabicyclo[2.2.2]octan-2-yl)methyl)-[1,1'-biphenyl]-4-yl)-1,1,1,3,3,3-hexafluoropropan-2-ol;

2-(2'-ethyl-4'-((5-(methylsulfonyl)-2,5-diazabicyclo[2.2.1]heptan-2-yl)methyl)-[1,1'-biphenyl]-4-yl)-1,1,1,3,3,3-hexafluoropropan-2-ol;

1-(3-((2-ethyl-4'-(1,1,1,3,3,3-hexafluoro-2-hydroxypropan-2-yl)-[1,1'-biphenyl]-4-yl)methyl)-3,8-diazabicyclo[3.2.1]octan-8-yl)ethan-1-one;

2-(2'-bromo-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-bromo-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

2-(4'-((8-ethyl-3,8-diazabicyclo[3.2.1]octan-3-yl)methyl)-2'-methyl-[1,1'-biphenyl]-4-yl)-1,1,1,3,3,3-hexafluoropropan-2-ol;

(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(tetrahydro-2H-pyran-4-yl)methanone;

ethyl 3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octane-8-carboxylate;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-3-methoxypropan-1-one;

N-(3-((4'-(1,1,1,3,3,3-hexafluoro-2-hydroxypropan-2-yl)-2-methyl-[1,1'-biphenyl]-4-yl)methyl)-3-azabicyclo[3.2.1]octan-8-yl)methanesulfonamide;

1,1,1,3,3,3-hexafluoro-2-(2'-methyl-4'-((8-(pyrimidin-4-ylmethyl)-3,8-diazabicyclo[3.2.1]octan-3-yl)methyl)-[1,1'-biphenyl]-4-yl)propan-2-ol;

2-(2'-chloro-4'-((8-((2-methylpyridin-4-yl)methyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(2'-methyl-4'-((5-(methylsulfonyl)-2,5-diazabicyclo[2.2.1]heptan-2-yl)methyl)-[1,1'-biphenyl]-4-yl)propan-2-ol;

1,1,1,3,3,3-hexafluoro-2-(2'-methyl-4'-((5-(methylsulfonyl)-2,5-diazabicyclo[2.2.2]octan-2-yl)methyl)-[1,1'-biphenyl]-4-yl)propan-2-ol;

1,1,1,3,3,3-hexafluoro-2-(2'-methyl-4'-((8-(pyridazin-4-ylmethyl)-3,8-diazabicyclo[3.2.1]octan-3-yl)methyl)-[1,1'-biphenyl]-4-yl)propan-2-ol;

2-(2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-2-methoxyethan-1-one;

2-(2'-chloro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-chloro-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(4'-((8-(methylsulfonyl)-3,8-diazabicyclo[3.2.1]octan-3-yl)methyl)-2'-(trifluoromethyl)-[1,1'-biphenyl]-4-yl)propan-2-ol;

1,1,1,3,3,3-hexafluoro-2-(4'-((8-(pyridin-4-ylmethyl)-3,8-diazabicyclo[3.2.1]octan-3-yl)methyl)-2'-(trifluoromethyl)-[1,1'-biphenyl]-4-yl)propan-2-ol;

1,1,1,3,3,3-hexafluoro-2-(2'-fluoro-4'-((8-(pyridin-4-ylmethyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-((trifluoromethyl)sulfonyl)-3,8-diazabicyclo[3.2.1]octan-3-yl)methyl)-[1,1'-biphenyl]-4-yl)propan-2-ol;

1,1,1,3,3,3-hexafluoro-2-(2'-fluoro-4'-((8-(methylsulfonyl)-3,8-diazabicyclo[3.2.1]octan-3-yl)methyl)-[1,1'-biphenyl]-4-yl)propan-2-ol;

1,1,1,3,3,3-hexafluoro-2-(4'-((8-((4-fluorophenyl)sulfonyl)-3,8-diazabicyclo[3.2.1]octan-3-yl)methyl)-2'-methyl-[1,1'-biphenyl]-4-yl)propan-2-ol;

1,1,1,3,3,3-hexafluoro-2-(4'-((8-((3-fluoropyridin-4-yl)methyl)-3,8-diazabicyclo[3.2.1]octan-3-yl)methyl)-2'-methyl-[1,1'-biphenyl]-4-yl)propan-2-ol;

2-(4'-((8-(cyclopropylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

2-(4'-((8-(benzylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

1,1,1,3,3,3-hexafluoro-2-(2'-methyl-4'-((8-((2-methylpyridin-4-yl)methyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-((2,2,2-trifluoroethyl)sulfonyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-(propylsulfonyl)-3,8-diazabicyclo[3.2.1]octan-3-yl)methyl)-[1,1'-biphenyl]-4-yl)propan-2-ol;

2-(4'-((8-(ethylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

4-((3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)methyl)pyridin-2-ol;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one;

1,1,1,3,3,3-hexafluoro-2-(2'-methyl-4'-((5-(pyridin-4-ylmethyl)-2,5-diazabicyclo[2.2.1]heptan-2-yl)methyl)-[1,1'-biphenyl]-4-yl)propan-2-ol;

1,1,1,3,3,3-hexafluoro-2-(2'-methyl-4'-((8-(methylsulfonyl)-3,8-diazabicyclo[3.2.1]octan-3-yl)methyl)-[1,1'-biphenyl]-4-yl)propan-2-ol;

2-(2,6-difluorophenyl)-1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one;

(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(pyridin-4-yl)methanone;

1,1,1,3,3,3-hexafluoro-2-(2'-methyl-4'-((5-(pyridin-4-ylmethyl)-2,5-diazabicyclo[2.2.2]octan-2-yl)methyl)-[1,1'-biphenyl]-4-yl)propan-2-ol;

1,1,1,3,3,3-hexafluoro-2-(4'-((8-(4-fluorobenzyl)-3,8-diazabicyclo[3.2.1]octan-3-yl)methyl)-2'-methyl-[1,1'-biphenyl]-4-yl)propan-2-ol;

1,1,1,3,3,3-hexafluoro-2-(2'-methyl-4'-((8-(pyridin-4-ylmethyl)-3,8-diazabicyclo[3.2.1]octan-3-yl)methyl)-[1,1'-biphenyl]-4-yl)propan-2-ol;

1,1,1,3,3,3-hexafluoro-2-(4'-((3-(pyridin-4-ylmethyl)-3,8-diazabicyclo[3.2.1]octan-8-yl)methyl)-[1,1'-biphenyl]-4-yl)propan-2-ol; and 1,1,1,3,3,3-hexafluoro-2-(4'-((8-(pyridin-4-ylmethyl)-3,8-diazabicyclo[3.2.1]octan-3-yl)methyl)-[1,1'-biphenyl]-4-yl)propan-2-ol; or a pharmaceutically acceptable salt or solvate thereof.

In some embodiments, the compounds provided herein were found to have $IC_{50}$s of about or less than 50 nM in the RORγ Gal4 ligand binding assay. In some embodiments, the compounds provided herein were found to have $IC_{50}$s of about or less than 100 nM in the RORγ Gal4 ligand binding assay. In some embodiments, the compounds provided herein have $IC_{50}$s of about 10 nM or less, about 20 nM or less, about 25 nM or less, about 50 nM or less, about 100 nM or less, about 250 nM or less, or about 500 nM or less in the RORγ Gal4 ligand binding assay. In another embodiment, the compounds provided herein modulate RORγ selectively over RORalpha.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I), (II), (IIa), (IIb), or (IIc)) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula (I), (II), (IIa), (IIb), or (IIc) is used as a single enantiomer. In some embodiments, a compound of Formula (I), (II), (IIa), (IIb), or (IIc) is used as a racemic mixture.

The methods and formulations described herein include the use of N-oxides (if appropriate), or pharmaceutically acceptable salts of compounds having the structures presented herein, as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula (I), (II), (IIa), (IIb), or (IIc) described herein include solvent addition forms thereof. Solvates contain either stoichiometric or non-stoichiometric amounts of a solvent with pharmaceutically acceptable solvents such as water, ethanol, and the like. Hydrates are formed when the solvent is water, or alcoholates are formed when the solvent is alcohol.

In some embodiments, sites on the compounds of Formula (I), (II), (IIa), (Ib), or (IIc) disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula (I), (II), (IIa), (IIb), or (IIc) disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements and thus decreasing toxicity or lowering the probability of drug-drug interactions.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

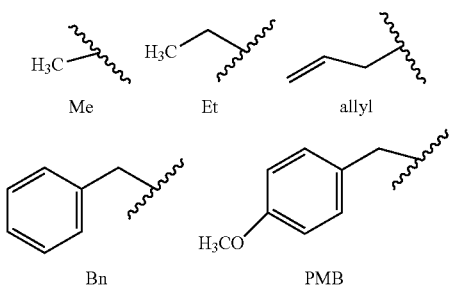

Protecting groups shown:
- trityl: (C₆H₅)₃C—
- t-butyl: (H₃C)₃C—
- Cbz: Bn-O-C(=O)—
- Boc: (CH₃)₃C-O-C(=O)—
- alloc: CH₂=CH-CH₂-O-C(=O)—
- acetyl: H₃C-C(=O)—
- Fmoc: fluorenylmethyloxycarbonyl
- TBDMS: (H₃C)₃C-Si(CH₃)₂—

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In one embodiment, provided herein are methods for modulating of RORγ activity in a cell by contacting the cell with an RORγ modulator. Examples of such RORγ modulators are described above.

In some embodiments is a method of treating a disease, disorder, or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is psoriasis. In some embodiments is a method of treating a disease, disorder or condition in an individual in need thereof comprising administering to the individual a therapeutically effective amount of a compound of Formula (I), (II), (IIa), (Ib), or (Ic), or a pharmaceutically acceptable salt or solvate thereof, wherein the disease, disorder, or condition is psoriatic arthritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is uveitis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is ulcerative colitis. In some embodiments is a method of treating a disease, disorder or condition in an individual in need thereof comprising administering to the individual a therapeutically effective amount of a compound of Formula (I), (II), (IIa), (Ib), or (IIc), or a pharmaceutically acceptable salt or solvate thereof, wherein the disease, disorder, or condition is asthma. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is allergic rhinitis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is chronic obstructive pulmonary disease (COPD). In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is atopic dermatitis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is vitiligo. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is vesiculobullous dermatosis. In some embodiments is a method of treating a disease, disorder or condition in an individual in need thereof comprising administering to the individual a therapeutically effective amount of a compound of Formula (I), (II), (IIa), (Ib), or (IIc), or a pharmaceutically acceptable salt or solvate thereof, wherein the disease, disorder, or condition is rheumatoid arthritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is ankylosing spondylitis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is reactive arthritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is arthritis associated with inflammatory bowel disease. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is juvenile rheumatoid arthritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is Crohn's disease. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is inflammatory bowel disease. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is lupus. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is lupus nephritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is multiple sclerosis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is axial spodyloarthritides. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is hidraenitis suppurativa. In some embodiments is a method of treating a disease, disorder or condition in an individual in need thereof comprising administering to the individual a therapeutically effective amount of a compound of Formula (I), (II), (IIa), (Ib), or (IIc), or a pharmaceutically acceptable salt or solvate thereof, wherein the disease, disorder, or condition is Sjögren's syndrome. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is regional enteritis. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is Tolosa-Hunt syndrome. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is undifferentiated connective tissue disease. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is obesity. In some embodiments is a method of treating a disease, disorder or condition in an individual in need thereof comprising administering to the individual a therapeutically effective amount of a compound of Formula (I), (II), (IIa), (IIb), or (IIc), or a pharmaceutically acceptable salt or solvate thereof, wherein the disease, disorder, or condition is obesity-induced insulin resistance. In some embodiments is a method of treating a disease, disorder or condition in an individual in need thereof comprising administering to the individual a therapeutically effective amount of a compound of Formula (I), (II), (IIa), (Ib), or (IIc), or a pharmaceutically acceptable salt or solvate thereof, wherein the disease, disorder, or condition is atherosclerosis. In some embodiments is a method of treating a disease, disorder or condition in an individual in need thereof comprising administering to the individual a therapeutically effective amount of a compound of Formula (I), (II), (IIa), (Ib), or (IIc), or a pharmaceutically acceptable salt or solvate thereof, wherein the disease, disorder, or condition is type II diabetes.

Pharmaceutical Compositions and Methods of Administration of RORγ Modulators

RORγ modulators described herein are administered to subjects in a biologically compatible form suitable for administration to treat or prevent diseases, disorders or conditions. Administration of RORγ modulators as described herein can be in any pharmacological form including a therapeutically effective amount of an RORγ modulator alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I), (II), (IIa), (IIb), or (IIc), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (II), or a pharmaceutically acceptable salt or solvate thereof. In some embodiments is a pharmaceutical composition comprising a pharmaceutically acceptable carrier and a compound of Formula (IIa), (IIb), or a pharmaceutically acceptable salt or solvate thereof. In some embodiments is a pharmaceutical composition comprising a pharmaceutically acceptable carrier and a compound of Formula (IIc), or a pharmaceutically acceptable salt or solvate thereof.

Another embodiment provides a pharmaceutical composition consisting essentially of a pharmaceutically acceptable carrier and a compound of Formula (I), (II), (IIa), (Ib), or (Ic), or a pharmaceutically acceptable salt or solvate thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (II), or a pharmaceutically acceptable salt or solvate thereof. In some embodiments is a pharmaceutical composition consisting essentially of a pharmaceutically acceptable carrier and a compound of Formula (IIa), (IIb), or a pharmaceutically acceptable salt or solvate thereof. In some embodiments is a pharmaceutical composition consisting essentially of a pharmaceutically acceptable carrier and a compound of Formula (IIc), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the RORγ modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the ROR modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such RORγ modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. RORγ modulators that exhibit large therapeutic indices are preferred. While RORγ modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such RORγ modulators lies preferably within a range of circulating concentrations that include the $ED_{50}$ with little or no toxicity. The dosage may vary within this range depending upon the dosage form employed and the route of administration utilized. For any RORγ modulator used in a method described herein, the therapeutically effective dose can be estimated initially from cell culture assays. A dose may be formulated in animal models to achieve a circulating plasma concentration range that includes the $IC_{50}$ (i.e., the concentration of RORγ modulator that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DMP | Dess-Martin periodinane |
| dppf | (diphenylphosphino)ferrocene |
| EtOAc | ethyl acetate |
| HBTU | N,N,N',N'-tetramethyl-O-(1H-benzotriazol-1-yl)uronium hexafluorophosphate |
| LC-MS | liquid chromatography-mass spectrometry |
| MeOH | methanol |
| TEA | triethylamine |
| rt | room temperature |

General Synthetic Scheme

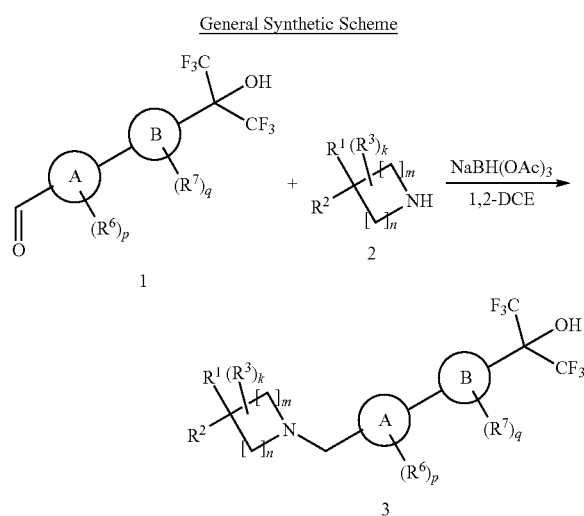

General Procedure

Aldehyde (1) (1.0 equiv) and secondary amine (2) (1.2 equiv) were combined in 1,2-DCE with catalytic amount of acid such as acetic acid or TFA. The mixture was stirred at rt for 1 to 3h. NaBH(OAc)$_3$ (3.0 equiv) was added to the solution. The resulting mixture was stirred at room temperature overnight. The reaction was quenched with MeOH, extracted with ethyl acetate (2×20 mL). The crude mixture was purified on a silica gel column to afford clean product (3).

Example A: Synthesis of Aldehyde Intermediate

Synthesis of Intermediate 1, Intermediate 2, and Intermediates 2A-2D

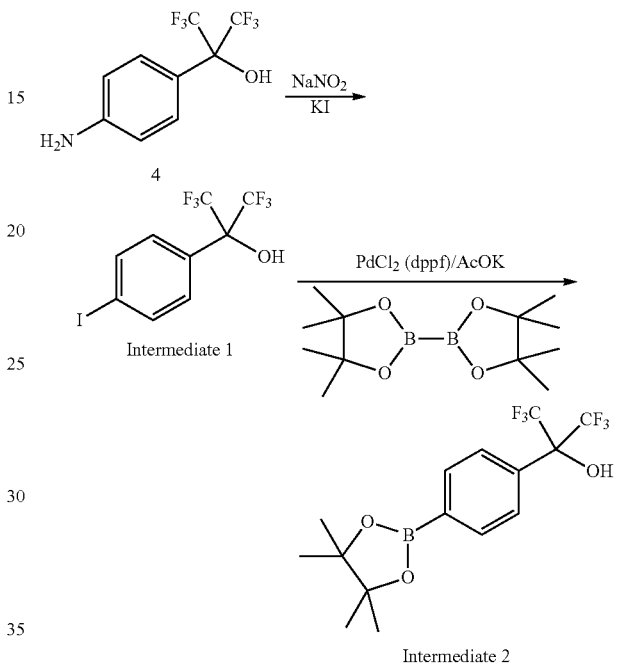

Procedure 1, Step A. To a solution of 2-(4-aminophenyl)-1,1,1,3,3,3-hexafluoropropan-2-ol (4) (15 g, 1.0 equiv) in DMF (120 mL) was added a solution of NaNO$_2$ (4.4 g, 1.1 equiv) in 30 mL water. The mixture was cooled to 0° C. for 15 min. 6 N HCl (29 mL, 3.0 equiv) was added dropwise to the reaction mixture for over 15 min at 0° C. The resulting mixture was stirred at 0° C. for 1 h. KI (10.1 g, 1.05 equiv) was added with portions (over 15 mins). The reaction mixture was stirred at 0° C. for 1 h, and then at room temperature overnight. The reaction was diluted with water (~500 mL) and extracted with EtOAc/hexane (2:1, 3×150 mL). The combined organic phase was washed with NaHSO$_3$, water, and brine. The crude mixture was purified on a silica gel column to afford 1,1,1,3,3,3-hexafluoro-2-(4-iodophenyl)propan-2-ol (Intermediate 1) (18.85 g, yield 88%) as a pale yellow oil.

Procedure 1, Step B. To a solution of compound Intermediate 1 (1 g, 1.0 equiv) in anhydrous 1,4-dioxane (20 mL) was added bis(pinacolato)diboron (0.89 g, 1.3 equiv), potassium acetate (0.265 g, 3 equiv), and Pd(dppf)$_2$Cl$_2$ (100 mg, 0.05 equiv). The mixture was degassed and then bubbled with N$_2$ for 5 min, and then stirred at 90° C. overnight. Upon cooling to room temperature, the mixture was poured into NH$_4$Cl solution and extracted with DCM. The organic phase was dried over MgSO$_4$, concentrated, and purified with silica gel column chromatography to afford 1,1,1,3,3,3-hexafluoro-2-(4-(4,4,5,5-tetramethyl-1,3,2-dioxaborolan-2-yl)phenyl)propan-2-ol (Intermediate 2) (450 mg, yield 45%) as a white solid.

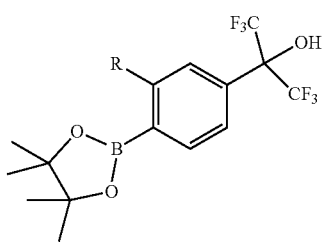

| R = —CH₃ | Intermediate 2A |
| R = —CH₂CH₃ | Intermediate 2B |
| R = F | Intermediate 2C |
| R = Cl | Intermediate 2D |

Procedure 2, Step A. 4-Bromo-3-chlorobenzaldehyde (1.0 g, 1.0 equiv) and TMSCF₃ (1.0 g, 1.5 equiv) were combined in dry THF (12 mL). The mixture was cooled over ice-water bath for 5 min. CsF (powder, 210 mg, 0.3 equiv) was added. The resulting mixture was stirred at 0° C. for 20 min and then at rt for 15 min. To the reaction mixture was added 1N TABF (1.0 equiv) at rt. The mixture was then stirred for 5 min. The reaction was quenched with 2N HCl and extracted with hexane (3×30 mL). The combined organic phase was washed with brine and dried over MgSO₄ to afford 1-(4-bromo-3-chlorophenyl)-2,2,2-trifluoroethan-1-ol.

Procedure 2, Step B. 1-(4-Bromo-3-chlorophenyl)-2,2,2-trifluoroethan-1-ol was dissolved in DCM, treated with DMP (1.5 equiv) at 0° C., and then stirred at rt for 1.5h. The reaction was quenched with saturated NaHCO₃ and Na₂S₃O₄. The organic phase was washed with brine. The crude product was purified by column chromatography to provide 1-(4-bromo-3-chlorophenyl)-2,2,2-trifluoroethan-1-one (1.3 g).

Procedure 2, Step C. 1-(4-bromo-3-chlorophenyl)-2,2,2-trifluoroethan-1-one (1.0 equiv) and TMSCF₃ (1.5 equiv) were combined in 15 mL THF and cooled with ice-water. CsF (powder, 1.0 equiv) was added. The mixture was stirred at 0° C. for 30 min and then for 10 min at rt. The reaction was quenched with 1N HCl and extracted with 3×30 mL hexane. The crude mixture was purified by column chromatography to afford 2-(4-bromo-3-chlorophenyl)-1,1,1,3,3,3-hexafluoropropan-2-ol (1.0 g).

Procedure 2, Step D. To 2-(4-bromo-3-chlorophenyl)-1,1,1,3,3,3-hexafluoropropan-2-ol (1.0 equiv) in anhydrous toluene (20 mL) was added 6 bis(pinacolato)diboron (1.05 equiv), potassium acetate (3 equiv), and Pd(dppf)₂Cl₂ (0.08 equiv). The mixture was degassed and then bubbled with N₂ for 5 min, and then stirred at 100° C. overnight. Upon cooling to room temperature, the mixture was poured into NH₄Cl solution and extracted with DCM. The organic phase was dried over MgSO₄, concentrated, and purified with column chromatography to afford 2-(3-chloro-4-(4,4,5,5-tetramethyl-1,3,2-dioxaborolan-2-yl)phenyl)-1,1,1,3,3,3-hexafluoropropan-2-ol (Intermediate 2D) as a white solid.

Procedure 3. 1,1,1,3,3,3-Hexafluoro-2-(3-methyl-4-(4,4,5,5-tetramethyl-1,3,2-dioxaborolan-2-yl)phenyl)propan-2-ol (Intermediate 2A) was prepared as described in Procedure 2, substituting 4-bromo-3-methylbenzaldehyde for 4-bromo-3-chlorobenzaldehyde in Step A.

Procedure 4. 2-(3-ethyl-4-(4,4,5,5-tetramethyl-1,3,2-dioxaborolan-2-yl)phenyl)-1,1,1,3,3,3-hexafluoropropan-2-ol (Intermediate 2B) was prepared as described in Procedure 2, substituting 4-bromo-3-ethylbenzaldehyde for 4-bromo-3-chlorobenzaldehyde in Step A.

Procedure 5. 1,1,1,3,3,3-hexafluoro-2-(3-fluoro-4-(4,4,5,5-tetramethyl-1,3,2-dioxaborolan-2-yl)phenyl)propan-2-ol (Intermediate 2C) was prepared as described in Procedure 2, substituting 4-bromo-3-fluorobenzaldehyde for 4-bromo-3-chlorobenzaldehyde in Step A.

Example B: Synthesis of Aldehyde Intermediates 1 and 1A-1

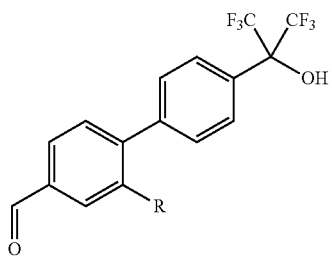

| R = —H | Aldehyde Intermediate 1 |
| R = —CH₃ | Aldehyde Intermediate 1A |
| R = —CF₃ | Aldehyde Intermediate 1B |
| R = F | Aldehyde Intermediate 1C |
| R = Cl | Aldehyde Intermediate 1D |
| R = Br | Aldehyde Intermediate 1E |

Synthesis of 4'-(1,1,1,3,3,3-hexafluoro-2-hydroxy-propan-2-yl)-[1,1'-biphenyl]-4-carbaldehyde (Aldehyde Intermediate 1)

Step A. To a solution of 2-(4-aminophenyl)-1,1,1,3,3,3-hexafluoropropan-2-ol (15 g, 1.0 equiv) in DMF (120 mL) was added a solution of NaNO₂ (4.4 g, 1.1 equiv) in 30 mL water. The mixture was cooled to 0° C. for 15 min. 6 N HCl (29 mL, 3.0 equiv) was added dropwise to the reaction mixture for over 15 min at 0° C. The resulting mixture was stirred at 0° C. for 1h. KI (10.1 g, 1.05 equiv) was added with portions (over 15 min) and the reaction mixture was stirred at 0° C. for 1 h, then rt overnight. The reaction was diluted with water (~500 mL) and extracted with EtOAc/hexane (2:1, 3×150 mL). The combined organic phase was washed with NaHSO₃, water, and brine. The crude mixture was purified on a silica gel column to afford 1,1,1,3,3,3-hexafluoro-2-(4-iodophenyl)propan-2-ol (18.9 g, yield 88%) as a pale yellow oil.

Step B. 1,1,1,3,3,3-hexafluoro-2-(4-iodophenyl)propan-2-ol (6.6 g, 1.0 equiv), (4-formylphenyl)boronic acid (3.21 g, 1.2 equiv), Pd(PPh₃)₄ (2.05 g, 0.1 equiv) and K₂CO₃ (7.4 g, 3.0 equiv) were combined in 150 mL dioxane and 40 water. The mixture was flushed with N₂ for 5 min and then heated at 80° C. for 8h under N₂. The reaction was extracted with EtOAc (2×200 mL). The combined organic phase was washed with 1N HCl and brine. The crude mixture was purified on a silica gel column to afford 4'-(1,1,1,3,3,3-hexafluoro-2-hydroxypropan-2-yl)-[1,1'-biphenyl]-4-carbaldehyde (Aldehyde Intermediate 1) (4.6 g, yield 74%) as a white solid.

Synthesis of 4'-(1,1,1,3,3,3-hexafluoro-2-hydroxypropan-2-yl)-2-methyl-[1,1'-biphenyl]-4-carbaldehyde (Aldehyde Intermediate 1A)

Aldehyde Intermediate 1A was prepared using the method described for Aldehyde Intermediate 1, but substituting (4-formyl-2-methylphenyl)boronic acid for (4-formylphenyl)boronic acid in Step B.

Synthesis of 4'-(1,1,1,3,3,3-hexafluoro-2-hydroxypropan-2-yl)-2-(trifluoromethyl)-[1,1'-biphenyl]-4-carbaldehyde (Aldehyde Intermediate 1B)

Aldehyde Intermediate 1B was prepared using the method described for Aldehyde Intermediate 1, but substituting (4-formyl-2-(trifluoromethyl)phenyl)boronic acid for (4-formylphenyl)boronic acid in Step B.

Synthesis of 2-fluoro-4'-(1,1,1,3,3,3-hexafluoro-2-hydroxypropan-2-yl)-[1,1'-biphenyl]-4-carbaldehyde (Aldehyde Intermediate 1C)

Aldehyde Intermediate 1C was prepared using the method described for Aldehyde Intermediate 1, but substituting (2-fluoro-4-formylphenyl)boronic acid for (4-formylphenyl) boronic acid in Step B.

Synthesis of 2-chloro-4'-(1,1,1,3,3,3-hexafluoro-2-hydroxypropan-2-yl)-[1,1'-biphenyl]-4-carbaldehyde (Aldehyde Intermediate 1D)

Aldehyde Intermediate 1D was prepared using the same method described for Aldehyde Intermediate 1, but substituting (2-chloro-4-formylphenyl)boronic acid for (4-formylphenyl)boronic acid in Step B.

Synthesis of 2-bromo-4'-(1,1,1,3,3,3-hexafluoro-2-hydroxypropan-2-yl)-[1,1'-biphenyl]-4-carbaldehyde (Aldehyde Intermediate 1E)

Aldehyde Intermediate 1E was prepared using the same method described for Aldehyde Intermediate 1, but substituting (2-bromo-4-formylphenyl)boronic acid for (4-formylphenyl)boronic acid in Step B.

Example C: Synthesis of Aldehyde Intermediates 2A-2D

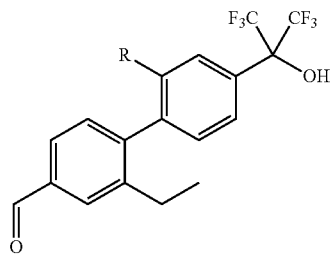

R = —H      Aldehyde Intermediate 2
R = —CH$_3$      Aldehyde Intermediate 2A
R = —CH$_2$CH$_3$      Aldehyde Intermediate 2B
R = F      Aldehyde Intermediate 2C
R = Cl      Aldehyde Intermediate 2D

Synthesis of 2-ethyl-4'-(1,1,1,3,3,3-hexafluoro-2-hydroxypropan-2-yl)-[1,1'-biphenyl]-4-carbaldehyde (Aldehyde Intermediate 2)

Step A. 4-bromo-3-ethylbenzoic acid (5.0 g, 1.0 equiv), N,O-dimethylhydroxylamine hydrochloride (3.2 g, 1.5 equiv) and HBTU (9.6 g, 1.15 equiv) were combined in 80 mL DMF at room temperature. To the reaction mixture was added Et$_3$N (11.2 g, 4.0 equiv) dropwise. The resulting mixture was stirred at rt overnight.

Step B. The reaction was diluted with 200 mL of ethyl acetate and 100 mL of hexane, then washed with 2×150 mL water, 2×100 mL 1N HCl, 2×100 mL saturated NaHCO$_3$, and brine. The organic phase was dried over MgSO$_4$ and concentrated in vacuum to provide 4-bromo-3-ethyl-N-methoxy-N-methylbenzamide (5.8 g, yield 97%) as a pale yellow oil which was used without further purification.

Step C. 4-Bromo-3-ethyl-N-methoxy-N-methylbenzamide (3.0 g, 1.0 equiv) and 4,4,4',4',5,5,5',5'-octamethyl-2,2'-bi(1,3,2-dioxaborolane) (3.22 g, 1.15 equiv) were dissolved in dry dioxane (25 mL). The mixture was degassed by bubbling N$_2$ for 5 min. PdCl$_2$(dppf) (0.81 g, 0.1 equiv) and potassium acetate (1.63 g, 1.5 equiv) were added to the reaction mixture. The resulting mixture was heated at 100° C. in a sealed-tube for 15h. The reaction mixture was diluted with 80 mL acetate and 80 mL hexane, washed with 3×80 mL water and 50 mL brine. The crude mixture was purified on a silica gel column to afford 3-ethyl-N-methoxy-N-methyl-4-(4,4,5,5-tetramethyl-1,3,2-dioxaborolan-2-yl)benzamide (3.34 g, yield 95%) as a pale yellow oil.

Step D. 3-ethyl-N-methoxy-N-methyl-4-(4,4,5,5-tetramethyl-1,3,2-dioxaborolan-2-yl)benzamide (2.24 g, 1.0 equiv), 1,1,1,3,3,3-hexafluoro-2-(4-iodophenyl)propan-2-ol (2.85 g, 1.1 equiv), Pd(PPh$_3$)$_4$ (0.81 g, 0.1 equiv) and K$_2$CO$_3$ (2.9 g, 3.0 equiv) were combined in 35 mL dioxane and 10 mL water. The mixture was flushed with N$_2$ for 5 min, and then heated at 95° C. for 14h under N$_2$. The reaction was extracted with EtOAc (2×200 mL). The combined organic phase was washed with 1N HCl and brine. The crude mixture was purified on a silica gel column to afford 2-ethyl-4'-(1,1,1,3,3,3-hexafluoro-2-hydroxypropan-2-yl)-N-methoxy-N-methyl-[1,1'-biphenyl]-4-carboxamide (2.28 g, yield 74.8%) as a white solid.

Step E. 2-ethyl-4'-(1,1,1,3,3,3-hexafluoro-2-hydroxypropan-2-yl)-N-methoxy-N-methyl-[1,1'-biphenyl]-4-carboxamide (2 g, 1.0 equiv) was dissolved in dry THF (20 mL) and the solution was cooled to −50° C. under N$_2$. LAH (4.6 mL, 1.0 equiv) was added dropwise. The mixture was stirred at −30° C. to −10° C. for an additional 40 min. The reaction was quenched with 1 mL water at −10° C. and then diluted with 50 mL 2N HCl. The mixture was extracted with 2×50 mL of ethyl acetate. The crude mixture was purified on a silica gel column to provide 2-ethyl-4'-(1,1,1,3,3,3-hexafluoro-2-hydroxypropan-2-yl)-[1,1'-biphenyl]-4-carbaldehyde (Aldehyde Intermediate 2) (1.41 g, yield 82%) as a white solid.

Synthesis of 2-ethyl-4'-(1,1,1,3,3,3-hexafluoro-2-hydroxypropan-2-yl)-2'-methyl-[1,1'-biphenyl]-4-carbaldehyde (Aldehyde Intermediate 2A)

2-ethyl-4'-(1,1,1,3,3,3-hexafluoro-2-hydroxypropan-2-yl)-2'-methyl-[1,1'-biphenyl]-4-carbaldehyde was prepared using the above procedure but substituting 1,1,1,3,3,3- hexafluoro-2-(4-iodo-3-methylphenyl)propan-2-ol for 1,1,1,3,3,3-hexafluoro-2-(4-iodophenyl)propan-2-ol in Step D.

Synthesis of 2,2'-diethyl-4'-(1,1,1,3,3,3-hexafluoro-2-hydroxypropan-2-yl)-[1,1'-biphenyl]-4-carbaldehyde (Aldehyde Intermediate 2B)

2,2'-diethyl-4'-(1,1,1,3,3,3-hexafluoro-2-hydroxypropan-2-yl)-[1,1'-biphenyl]-4-carbaldehyde was prepared using the above procedure, but substituting 2-(3-ethyl-4-iodophenyl)-1,1,1,3,3,3-hexafluoropropan-2-ol for 1,1,1,3,3,3-hexafluoro-2-(4-iodophenyl)propan-2-ol in Step D.

Synthesis of 2-ethyl-2'-fluoro-4'-(1,1,1,3,3,3-hexafluoro-2-hydroxypropan-2-yl)-[1,1'-biphenyl]-4-carbaldehyde (Aldehyde Intermediate 2C)

2-ethyl-2'-fluoro-4'-(1,1,1,3,3,3-hexafluoro-2-hydroxypropan-2-yl)-[1,1'-biphenyl]-4-carbaldehyde was prepared using the above procedure, but substituting 1,1,1,3,3,3-hexafluoro-2-(3-fluoro-4-iodophenyl)propan-2-ol for 1,1,1,3,3,3-hexafluoro-2-(4-iodophenyl)propan-2-ol in Step D.

Synthesis of 2'-chloro-2-ethyl-4'-(1,1,1,3,3,3-hexafluoro-2-hydroxypropan-2-yl)-[1,1'-biphenyl]-4-carbaldehyde (Aldehyde Intermediate 2D)

2'-chloro-2-ethyl-4'-(1,1,1,3,3,3-hexafluoro-2-hydroxypropan-2-yl)-[1,1'-biphenyl]-4-carbaldehyde was prepared using the above procedure, but substituting 2-(3-chloro-4-iodophenyl)-1,1,1,3,3,3-hexafluoropropan-2-ol for 1,1,1,3,3,3-hexafluoro-2-(4-iodophenyl)propan-2-ol in Step D.

Example D: Synthesis of Aldehyde Intermediates 3A, 3C and 3D

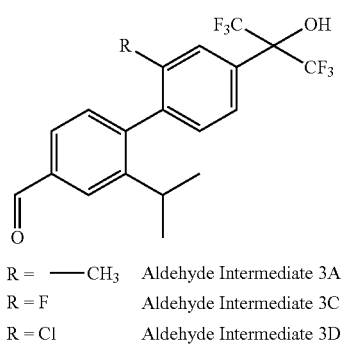

R = —CH₃  Aldehyde Intermediate 3A
R = F     Aldehyde Intermediate 3C
R = Cl    Aldehyde Intermediate 3D Synthesis of 4'-(1,1,1,3,3,3-hexafluoro-2-hydroxypropan-2-yl)-2-isopropyl-2'-methyl-[1,1'-biphenyl]-4-carbaldehyde (Aldehyde Intermediate 3A)

Step A. To a mixture of 4-hydroxy-3-isopropylbenzoic acid (2.0 g, 11 mmol), triethylamine (3.3 g, 33 mmol) and N,O-dimethylhydroxylamine hydrochloride (1.1 g, 110 mmol) in DCM (100 mL) was added HBTU (6.3 g, 1.7 mmol). The mixture was stirred at room temperature overnight. The reaction mixture was washed with saturated NaHCO₃ solution, 2N HCl, and water. The organic phase was dried over MgSO₄, and concentrated in vacuo to afford 4-hydroxy-3-isopropyl-N-methoxy-N-methylbenzamide (4.5 g) as a pale red solid which was used without further purification.

Step B. To a mixture of 4-hydroxy-3-isopropyl-N-methoxy-N-methylbenzamide (500 mg, 2.2 mmol) and pyridine (530 µL, 6.6 mmol) in DCM (30 mL) was added trifluoromethanesulfonic anhydride (0.93 g, 3.3 mmol) dropwise at 0° C. The mixture was stirred at 0° C. for 1 h, and washed with saturated NaHCO₃ solution, and water. The organic phase was dried over MgSO₄, concentrated, and purified by column chromatography to afford 2-isopropyl-4-(methoxy(methyl)carbamoyl)phenyl trifluoromethanesulfonate (680 mg) as a white solid.

Step C. The mixture of 2-isopropyl-4-(methoxy(methyl)carbamoyl)phenyl trifluoromethanesulfonate (1.0 equiv), and 1,1,1,3,3,3-hexafluoro-2-(3-methyl-4-(4,4,5,5-tetramethyl-1,3,2-dioxaborolan-2-yl)phenyl)propan-2-ol (Intermediate 2A) (1.2 equiv), Pd(PPh₃)₄ (0.1 equiv) K₂CO₃ (3.0 equiv) in dioxane (10 mL) and water (4 mL) was heated at 90° C. under N₂ overnight. The mixture was cooled to rt and washed with water and brine. The organic layer was concentrated and purified by column chromatography to afford 4'-(1,1,1,3,3,3-hexafluoro-2-hydroxypropan-2-yl)-2-isopropyl-N-methoxy-N,2'-dimethyl-[1,1'-biphenyl]-4-carboxamide.

Step D. To a solution of 4'-(1,1,1,3,3,3-hexafluoro-2-hydroxypropan-2-yl)-2-isopropyl-N-methoxy-N,2'-dimethyl-[1,1'-biphenyl]-4-carboxamide (1 equiv) in anhydrous THF (2 mL) was added 1.0 M LAH solution in THF (1.0 equiv) at −78° C. The reaction was stirred at −78° C. for 1 h and quenched by adding EtOAc. The mixture was poured into 1N HCl solution and extracted with DCM. The organic phase was dried over MgSO₄, concentrated, and purified by column chromatography to afford 4'-(1,1,1,3,3,3-hexafluoro-2-hydroxypropan-2-yl)-2-isopropyl-2'-methyl-[1,1'-biphenyl]-4-carbaldehyde as a white solid (Aldehyde Intermediate 3A).

Synthesis of 2'-fluoro-4'-(1,1,1,3,3,3-hexafluoro-2-hydroxypropan-2-yl)-2-isopropyl-[1,1'-biphenyl]-4-carbaldehyde (Aldehyde Intermediate 3C)

Aldehyde Intermediate 3C was prepared as described above, but substituting Intermediate 2C for Intermediate 2A in Step C.

Synthesis of 2'-chloro-4'-(1,1,1,3,3,3-hexafluoro-2-hydroxypropan-2-yl)-2-isopropyl-[1,1'-biphenyl]-4-carbaldehyde (Aldehyde intermediate 3D)

Aldehyde Intermediate 3D was prepared as described above, but substituting Intermediate 2D for Intermediate 2A in Step C.

Example E: Synthesis of 5-ethyl-6-(4-(1,1,1,3,3,3-hexafluoro-2-hydroxypropan-2-yl)-2-methylphenyl)nicotinaldehyde (Aldehyde Intermediate 4)

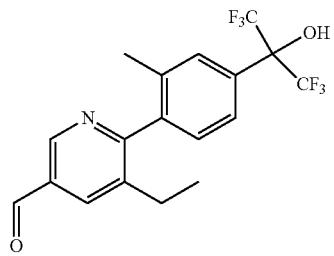 [SMILES: CCc1cc(C=O)cnc1-c1ccc(C(O)(C(F)(F)F)C(F)(F)F)cc1C]

To a solution of 3-ethylpyridin-2-amine (1 g, 8.2 mmol, 1 equiv) in 1,4-dioxane (10 mL) and water (2 mL) at 0° C. was added NBS (1.45 g, 8.2 mmol, 1 equiv). The resulting mixture was stirring at 0° C. for 2h. The reaction was diluted with water (50 mL) and extracted with DCM. The organic phase was separated and concentrated. The residue was purified with column chromatography to afford 5-bromo-3-ethylpyridin-2-amine (1.5 g) as a white solid.

5-Bromo-3-ethylpyridin-2-amine (1 g, 1 equiv), Zn(CN)$_2$ (1.5 equiv), and PdCl$_2$(dppf) (10%) were combined in dry DMF (18 mL). The resulting mixture was heated to 120° C. overnight. The reaction mixture was cooled to room temperature, poured into DCM (100 mL), and washed with water and saturated NaHCO$_3$. The organic phase was dried over MgSO$_4$ and concentrated. The residue was purified with column chromatography to afford 6-amino-5-ethylnicotinonitrile (0.7 g) as a white solid.

To a solution of 6-amino-5-ethylnicotinonitrile (0.7 g, 1 equiv) in CH$_3$CN (15 mL) was added CuCl$_2$ (2 equiv) and CuCl (2 equiv). To the mixture was added n-BuONO (1.3 equiv) at rt. The resulting mixture was stirred at rt for 1 h and then heated at reflux overnight. The reaction mixture was cooled and diluted with CH$_2$C$_2$. The mixture was washed with water, saturated NaHCO$_3$ solution, and water. The organic phase was dried over MgSO$_4$, concentrated, and purified by column chromatography to afford 6-chloro-5-ethylnicotinonitrile (0.42 g) as a white solid.

6-chloro-5-ethylnicotinonitrile (200 mg, 0.53 mmol, 1 equiv) was dissolved in 6 N HCl solution. The reaction was stirred at 100° C. for 3h, and then concentrated to give 6-chloro-5-ethylnicotinic acid which was used without purification.

To a mixture of 6-chloro-5-ethylnicotinic acid (220 mg, 1 equiv), triethylamine (150 mg, 3 equiv) and N,O-dimethylhydroxylamine hydrochloride (85 mg, 1.5 equiv) in DCM (10 mL) was added HBTU (280 mg, 1.4 equiv). The mixture was stirred at room temperature overnight. The reaction was washed with saturated NaHCO$_3$ solution, 2N HCl, and water. The organic phase was dried over MgSO$_4$ and concentrated in vacuo to afford 6-chloro-5-ethyl-N-methoxy-N-methylnicotinamide (150 mg) which was used without further purification.

6-chloro-5-ethyl-N-methoxy-N-methylnicotinamide was combined with Intermediate 2A under Suzuki reaction conditions described in Step B of Example B to provide 5-ethyl-6-(4-(1,1,1,3,3,3-hexafluoro-2-hydroxypropan-2-yl)-2-methylphenyl)-N-methoxy-N-methylnicotinamide. 5-Ethyl-6-(4-(1,1,1,3,3,3-hexafluoro-2-hydroxypropan-2-yl)-2-methylphenyl)-N-methoxy-N-methylnicotinamide was treated with 1M LAH (1.2 equiv) at −78° C. to afford aldehyde 5-ethyl-6-(4-(1,1,1,3,3,3-hexafluoro-2-hydroxypropan-2-yl)-2-methylphenyl)nicotinaldehyde (Aldehyde Intermediate 4).

Example F: Synthesis of 3-ethyl-4-(5-(1,1,1,3,3,3-hexafluoro-2-hydroxypropan-2-yl)pyridin-2-yl)benzaldehyde (Aldehyde Intermediate 5)

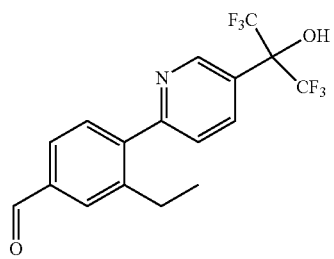 [SMILES: CCc1cc(C=O)ccc1-c1ccc(C(O)(C(F)(F)F)C(F)(F)F)cn1]

Methyl 6-bromonicotinate (1.0 equiv) was dissolved in THF (20 mL), added TMSCF$_3$ (5.0 equiv), the mixture was cooled at −15° C. To the mixture was added 1M TBAF in THE (3.0 equiv) dropwise for over 20 min. After addition of TMSCF$_3$, saturated NH$_4$Cl (50 mL) was added slowly. The mixture was stirred at rt for 15 min and extracted with 2×40 mL hexane. The organic phase was dried over MgSO$_4$ and concentrated in vacuum to afford 1-(6-bromopyridin-3-yl)-2,2,2-trifluoroethan-1-one as an oil that was used for next reaction without purification. 1-(6-Bromopyridin-3-yl)-2,2,2-trifluoroethan-1-one and TMSCF$_3$ (5.0 equiv) was dissolved in anhydrous THF (20 mL), cooled with ice-water. TBAF (1M, 5 mL) was added dropwise. The resulting mixture was stirred at 0° C. for 2h. The reaction was quenched with saturated NH$_4$Cl (80 mL). The mixture was extracted with 2×40 mL hexane. The crude mixture was purified on a silica gel column to afford 2-(6-bromopyridin-3-yl)-1,1,1,3,3,3-hexafluoropropan-2-ol.

2-(6-Bromopyridin-3-yl)-1,1,1,3,3,3-hexafluoropropan-2-ol (1.0 equiv) was combined with 3-ethyl-N-methoxy-N-methyl-4-(4,4,5,5-tetramethyl-1,3,2-dioxaborolan-2-yl)benzamide (1.2 equiv) under Suzuki coupling conditions described in Step B of Example B to afford 3-ethyl-4-(5-(1,1,1,3,3,3-hexafluoro-2-hydroxypropan-2-yl)pyridin-2-yl)-N-methoxy-N-methylbenzamide. 3-Ethyl-4-(5-(1,1,1,3,3,3-hexafluoro-2-hydroxypropan-2-yl)pyridin-2-yl)-N-methoxy-N-methylbenzamide was reduced by LAH at −78° C. to afford 3-ethyl-4-(5-(1,1,1,3,3,3-hexafluoro-2-hydroxypropan-2-yl)pyridin-2-yl)benzaldehyde aldehyde (Aldehyde Intermediate 5).

Example G: Synthesis of 2'-ethyl-4'-formyl-4-(1,1,1,3,3,3-hexafluoro-2-hydroxypropan-2-yl)-[1,1'-biphenyl]-2-carboxamide (Aldehyde Intermediate 6A) and 2'-ethyl-4'-formyl-4-(1,1,1,3,3,3-hexafluoro-2-hydroxypropan-2-yl)-[1,1'-biphenyl]-2-carbonitrile (Aldehyde Intermediate 6B)

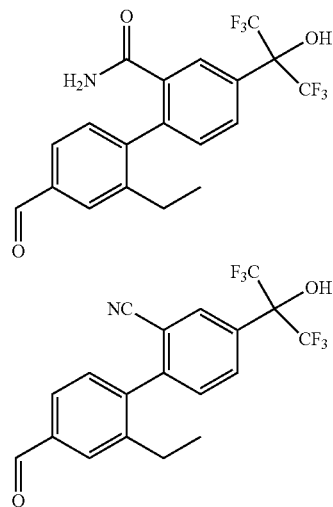

Step A. 4-Bromo-3-ethyl-N-methoxy-N-methylbenzamide (1.0 equiv) was dissolved in dry THF and cooled to −50° C. To the solution was added 1M LAH in THF (0.6 equiv). The reaction was stirred at −30° C. for 1 h and then quenched with 1N HCl at −10° C. to afford 4-bromo-3-ethylbenzaldehyde aldehyde which was used without purification.

Step B. 4-Bromo-3-ethylbenzaldehyde (1.0 equiv) and 4,4,4',4',5,5,5',5'-octamethyl-2,2'-bi(1,3,2-dioxaborolane) (1.15 equiv) were dissolved in dry toluene (25 mL). The mixture was degassed by bubbling N₂ for 5 min. PdCl₂(dppf)(0.1 equiv) and potassium acetate (1.5 equiv) were added to reaction mixture. The resulting mixture was heated at 100° C. in a sealed-tube for 15h. The reaction mixture was dried in vacuum. The crude mixture was purified on a silica gel column to afford 3-ethyl-4-(4,4,5,5-tetramethyl-1,3,2-dioxaborolan-2-yl)benzaldehyde.

Step C. 2-Bromo-5-formylbenzonitrile (1.0 equiv) was dissolved in anhydrous THF and TMSCF₃ (2.0 equiv) was added. The mixture was cooled at 0° C. To the mixture was added CsF (0.3 equiv). The resulting mixture was stirred at 0° C. for 30 min, then at rt for 1 h. To the mixture was added 1M TABF (2.0 equiv). The reaction was then quenched with saturated NH₄Cl (50 mL), extracted with 2×40 mL hexane. The organic phase was dried over MgSO₄ and concentrated in vacuum to afford 2-bromo-5-(2,2,2-trifluoro-1-hydroxyethyl)benzonitrile as an oil that was used for next reaction without purification.

Step D. 2-Bromo-5-(2,2,2-trifluoro-1-hydroxyethyl)benzonitrile was dissolved in DCM and DMP (1.5 equiv) was added at rt. The mixture was stirred at rt for 1 h and then quenched with saturated NaHCO₃. The crude mixture was purified on a silica gel column to afford 2-bromo-5-(2,2,2-trifluoroacetyl)benzonitrile.

Step E. 2-Bromo-5-(2,2,2-trifluoroacetyl)benzonitrile and TMSCF₃ (2 equiv) was dissolved in anhydrous THF (20 mL) and cooled with ice-water. 1M TBAF in THF (1.0 equiv) was added dropwise. The resulting mixture was stirred at 0° C. for 2h. The reaction was quenched with saturated NH₄Cl (80 mL). The mixture was extracted with 2×40 mL hexane. The crude mixture was purified on a silica gel column to afford 2-bromo-5-(1,1,1,3,3,3-hexafluoro-2-hydroxypropan-2-yl)benzonitrile.

Step F. 2-bromo-5-(1,1,1,3,3,3-hexafluoro-2-hydroxypropan-2-yl)benzonitrile was combined with 3-ethyl-4-(4,4,5,5-tetramethyl-1,3,2-dioxaborolan-2-yl)benzaldehyde from Step B under Suzuki coupling conditions under Step B of Example B to afford 2'-ethyl-4'-formyl-4-(1,1,1,3,3,3-hexafluoro-2-hydroxypropan-2-yl)-[1,1'-biphenyl]-2-carboxamide (Aldehyde Intermediate 6A) and 2'-ethyl-4'-formyl-4-(1,1,1,3,3,3-hexafluoro-2-hydroxypropan-2-yl)-[1,1'-biphenyl]-2-carbonitrile (Aldehyde Intermediate 6B).

Example H: Synthesis of Aldehyde Intermediates 7A, 7C and 7D

Synthesis of 2-ethyl-3,6-difluoro-4'-(1,1,1,3,3,3-hexafluoro-2-hydroxypropan-2-yl)-2'-methyl-[1,1'-biphenyl]-4-carbaldehyde (Aldehyde Intermediate 7A)

Step A. To a mixture of 2,5-difluoro-4-hydroxybenzoic acid (1 equiv), triethylamine (3 equiv), and N,O-dimethylhydroxylamine hydrochloride (10 equiv) in DCM (20 mL) was added HBTU (2.5 equiv). The mixture was stirred at room temperature overnight and the washed with 2N HCl and water. The organic phase was dried over MgSO₄, concentrated, and purified on a silica gel column to afford 2,5-difluoro-4-hydroxy-N-methoxy-N-methylbenzamide as a colorless oil.

Step B. To a solution of 2,5-difluoro-4-hydroxy-N-methoxy-N-methylbenzamide (1 equiv) in acetic acid (4 mL) was added NBS (1.1 equiv) at 0° C. The reaction mixture was warmed to room temperature and stirred for 2h. The solvent was removed under reduced pressure. The residue was dissolved in EtOAc, washed with water, concentrated, and purified on a silica gel column to afford 3-bromo-2,5-difluoro-4-hydroxy-N-methoxy-N-methylbenzamide as a white solid.

Step C. To a solution of 3-bromo-2,5-difluoro-4-hydroxy-N-methoxy-N-methylbenzamide (1 equiv) in 1,4-dioxane (5 mL) was added 4,4,5,5-tetramethyl-2-vinyl-1,3,2-dioxaborolane (1.5 equiv), 2M potassium carbonate solution (3 equiv), and Pd(PPh₃)₄ (0.05 equiv). The mixture was degassed and then bubbled with N₂ for 5 min, and then stirred at 90° C. overnight. Upon cooling to room temperature, the mixture was poured into NH₄Cl solution and extracted with DCM. The organic phase was dried over MgSO₄, concentrated, and purified on a silica gel column to afford 2,5-difluoro-4-hydroxy-N-methoxy-N-methyl-3-vinylbenzamide as a white solid.

Step D. To a solution of 2,5-difluoro-4-hydroxy-N-methoxy-N-methyl-3-vinylbenzamide (1.0 equiv) in MeOH (10 mL) was added Pd/C (10% wt.). The reaction was shaken under H₂ (50 psi) environment for 14h. The mixture was filtered to remove catalyst and concentrated to afford 3-ethyl-2,5-difluoro-4-hydroxy-N-methoxy-N-methylbenzamide as a white solid.

Step E. To a mixture of 3-ethyl-2,5-difluoro-4-hydroxy-N-methoxy-N-methylbenzamide (1 equiv) and pyridine (0.5 mL) in DCM (10 mL) was added trifluoromethanesulfonic anhydride (1.5 equiv) dropwise at 0° C. The mixture was stirred at 0° C. for 1 h and washed with saturated NaHCO₃ solution and water. The organic phase was dried over MgSO₄, concentrated, and purified on a silica gel column to afford 2-ethyl-3,6-difluoro-4-(methoxy(methyl)carbamoyl) phenyl trifluoromethanesulfonate as a pale yellow oil.

Step F. To a solution of 2-ethyl-3,6-difluoro-4-(methoxy (methyl)carbamoyl)phenyl trifluoromethanesulfonate (1 equiv) in 1,4-dioxane (10 mL) was added Intermediate 2A (1.5 equiv), 2M potassium carbonate solution (3 equiv), and Pd(PPh₃)₄ (0.05 equiv). The mixture was degassed and then bubbled with N₂ for 5 min, and then stirred at 90° C. overnight. Upon cooling to room temperature, the mixture was poured into NH₄Cl solution and extracted with DCM. The organic phase was dried over MgSO₄, concentrated, and purified on a silica gel column to afford 2-ethyl-3,6-difluoro-4'-(1,1,1,3,3,3-hexafluoro-2-hydroxypropan-2-yl)-N-methoxy-N,2'-dimethyl-[1,1'-biphenyl]-4-carboxamide as a white solid.

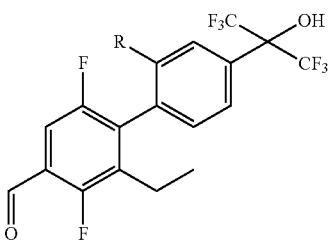

R = —CH₃  Aldehyde Intermediate 7A
R = F     Aldehyde Intermediate 7C
R = Cl    Aldehyde Intermediate 7D Step G. To a solution of 2-ethyl-3,6-difluoro-4'-(1,1,1,3,3,3-hexafluoro-2-hydroxypropan-2-yl)-N-methoxy-N,2'-dimethyl-[1,1'-biphenyl]-4-carboxamide (120 mg, 0.25 mmol, 1 equiv) in anhydrous THF (2 mL) was added 1.0 M LAH solution in THF (1.0 equiv) at −78° C. The reaction was stirred at −7° C. for 1 h and quenched by adding EtOAc before being warmed to room temperature. The mixture was poured into $NH_4Cl$ solution and extracted with DCM. The organic phase was dried over $MgSO_4$, concentrated, and purified on a silica gel column to afford 2-ethyl-3,6-difluoro-4'-(1,1,1,3,3,3-hexafluoro-2-hydroxypropan-2-yl)-2'-methyl-[1,1'-biphenyl]-4-carbaldehyde aldehyde (Aldehyde Intermediate 7A) as a white solid.

Synthesis of 2-ethyl-2',3,6-trifluoro-4'-(1,1,1,3,3,3-hexafluoro-2-hydroxypropan-2-yl)-[1,1'-biphenyl]-4-carbaldehyde (Aldehyde Intermediate 7C)

2-Ethyl-2',3,6-trifluoro-4'-(1,1,1,3,3,3-hexafluoro-2-hydroxypropan-2-yl)-[1,1'-biphenyl]-4-carbaldehyde was prepared using the above procedure, but substituting Intermediate 2C for Intermediate 2A in Step F.

Synthesis of 2'-chloro-2-ethyl-3,6-difluoro-4'-(1,1,1,3,3,3-hexafluoro-2-hydroxypropan-2-yl)-[1,1'-biphenyl]-4-carbaldehyde (Aldehyde Intermediate 7D)

2'-Chloro-2-ethyl-3,6-difluoro-4'-(1,1,1,3,3,3-hexafluoro-2-hydroxypropan-2-yl)-[1,1'-biphenyl]-4-carbaldehyde was prepared using the above procedure, but substituting Intermediate 2D for Intermediate 2A in Step F.

Example I: Synthesis of 6-ethyl-2,3-difluoro-4'-(1,1,1,3,3,3-hexafluoro-2-hydroxypropan-2-yl)-2'-methyl-[1,1'-biphenyl]-4-carbaldehyde (Aldehyde Intermediate 8)

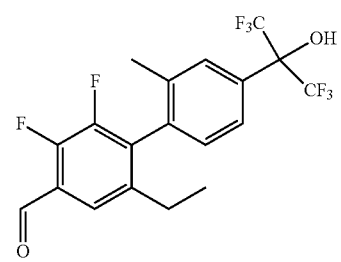 [SMILES: CCc1cc(C=O)c(F)c(F)c1-c1ccc(C(O)(C(F)(F)F)C(F)(F)F)cc1C]

6-ethyl-2,3-difluoro-4'-(1,1,1,3,3,3-hexafluoro-2-hydroxypropan-2-yl)-2'-methyl-[1,1'-biphenyl]-4-carbaldehyde was prepared using the same procedure described for Aldehyde Intermediate 7 except that 2,3-difluoro-4-hydroxybenzoic acid was substituted for 2,5-difluoro-4-hydroxybenzoic acid in Step A.

Example K: Synthesis of Aldehyde Intermediates 10, 10 A, 1° C. and 10D

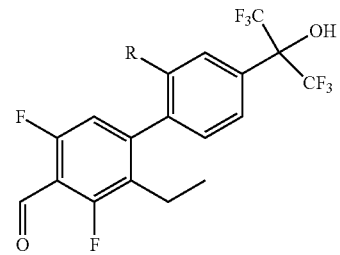

| R = | —H | Aldehyde Intermediate 10 |
| R = | —$CH_3$ | Aldehyde Intermediate 10A |
| R = F | | Aldehyde Intermediate 10C |
| R = Cl | | Aldehyde Intermediate 10D |

Synthesis of 2-ethyl-3,5-difluoro-4'-(1,1,1,3,3,3-hexafluoro-2-hydroxypropan-2-yl)-[1,1'-biphenyl]-4-carbaldehyde (Aldehyde Intermediate 10)

Aldehyde Intermediate 10 was prepared using the same procedure described for Aldehyde Intermediate 7, but substituting 2,6-difluoro-4-hydroxybenzoic acid for 2,5-difluoro-4-hydroxybenzoic acid in Step A and substituting Intermediate 2 for Intermediate 2A in Step F.

Synthesis of 2-ethyl-3,5-difluoro-4'-(1,1,1,3,3,3-hexafluoro-2-hydroxypropan-2-yl)-2'-methyl-[1,1'-biphenyl]-4-carbaldehyde (Aldehyde Intermediate 10A)

Aldehyde intermediate 2-ethyl-3,5-difluoro-4'-(1,1,1,3,3,3-hexafluoro-2-hydroxypropan-2-yl)-2'-methyl-[1,1'-biphenyl]-4-carbaldehyde was prepared using the same procedure described for Aldehyde Intermediate 7, but substituting 2,6-difluoro-4-hydroxybenzoic acid for 2,5-difluoro-4-hydroxybenzoic acid in Step A.

Synthesis of 2-ethyl-2',3,5-trifluoro-4'-(1,1,1,3,3,3-hexafluoro-2-hydroxypropan-2-yl)-[1,1'-biphenyl]-4-carbaldehyde (Aldehyde Intermediate 10C)

Aldehyde Intermediate 10C was prepared using the same procedure described for Aldehyde Intermediate 7, but substituting 2,6-difluoro-4-hydroxybenzoic acid for 2,5-difluoro-4-hydroxybenzoic acid in Step A and substituting Intermediate 2C for Intermediate 2A in Step F.

Synthesis of 2'-chloro-2-ethyl-3,5-difluoro-4'-(1,1,1,3,3,3-hexafluoro-2-hydroxypropan-2-yl)-[1,1'-biphenyl]-4-carbaldehyde (Aldehyde Intermediate 10D)

Aldehyde Intermediate 10D was prepared using the same procedure described for Aldehyde Intermediate 7, but substituting 2,6-difluoro-4-hydroxybenzoic acid for 2,5-difluoro-4-hydroxybenzoic acid in Step A and substituting Intermediate 2D for Intermediate 2A in Step F.

Example L: Synthesis of 2'-ethyl-4'-(1,1,1,3,3,3-hexafluoro-2-hydroxypropan-2-yl)-2-methyl-[1,1'-biphenyl]-4-carbaldehyde (Aldehyde Intermediate 11)

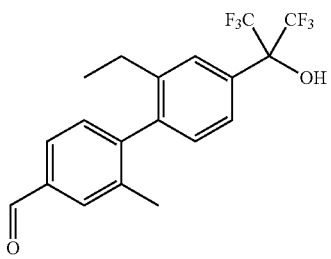 [SMILES: CCc1cc(C(O)(C(F)(F)F)C(F)(F)F)ccc1-c1ccc(C=O)cc1C]

2'-Ethyl-4'-(1,1,1,3,3,3-hexafluoro-2-hydroxypropan-2-yl)-2-methyl-[1,1'-biphenyl]-4-carbaldehyde (Aldehyde Intermediate 11) was prepared by combining a mixture of 4-bromo-3-methylbenzaldehyde and Intermediate 2B, Pd(PPh$_3$)$_4$ and Na$_2$CO$_3$ (2N solution) in 1,4-dioxane and water and heating at 90° C. under nitrogen gas overnight.

Example M: Synthesis of 5-fluoro-4'-(1,1,1,3,3,3-hexafluoro-2-hydroxypropan-2-yl)-2-isopropyl-2'-methyl-[1,1'-biphenyl]-4-carbaldehyde (Aldehyde Intermediate 12A)

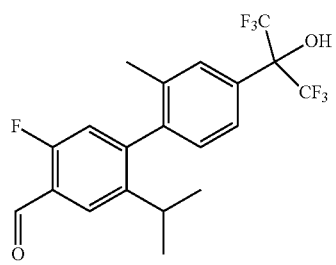 [SMILES: Cc1cc(C(O)(C(F)(F)F)C(F)(F)F)ccc1-c1cc(F)c(C=O)cc1C(C)C]

Step A. To a mixture of 2-fluoro-4-hydroxybenzoic acid (1 equiv), triethylamine (3 equiv) and N,O-dimethylhydroxylamine hydrochloride (10 equiv) in DMF (10 mL) was added HBTU (2.5 equiv). The mixture was stirred at room temperature overnight. The reaction mixture was diluted with 40 mL ethyl acetate and 20 mL hexane, washed with 2N HCl, water, and brine. The organic phase was dried over MgSO$_4$, concentrated, and purified on a silica gel column to afford 2-fluoro-4-hydroxy-N-methoxy-N-methylbenzamide.

Step B. To a solution of 2-fluoro-4-hydroxy-N-methoxy-N-methylbenzamide (1.0 equiv) in AcOH (10 mL) was added NBS (1.0 g) at 0° C. The reaction mixture was stirred at 0° C. to rt for 1 h, diluted with EtOAc, and washed with water. The organic layer was concentrated and purified on a silica gel column to give 5-bromo-2-fluoro-4-hydroxy-N-methoxy-N-methylbenzamide.

Step C. 5-Bromo-2-fluoro-4-hydroxy-N-methoxy-N-methylbenzamide was dissolved in DMF, and K$_2$CO$_3$ (3.0 equiv) and benzyl bromide (1.2 equiv) were added. The resulting mixture was heated at 50° C. for 1h. The reaction was diluted with ethyl acetate and washed with water. The crude mixture was purified on a silica gel column to afford 4-(benzyloxy)-5-bromo-2-fluoro-N-methoxy-N-methylbenzamide.

Step D. 4-(Benzyloxy)-5-bromo-2-fluoro-N-methoxy-N-methylbenzamide and 4,4,5,5-tetramethyl-2-(prop-1-en-2-yl)-1,3,2-dioxaborolane were combined under the following Suzuki coupling reaction conditions, Pd(PPh$_3$)$_4$ and K$_2$CO$_3$ in 1,4-dioxane and water, and the reaction was heated at 90° C. under nitrogen gas overnight, to afford 4-(benzyloxy)-2-fluoro-N-methoxy-N-methyl-5-(prop-1-en-2-yl)benzamide.

Step E. 4-(Benzyloxy)-2-fluoro-N-methoxy-N-methyl-5-(prop-1-en-2-yl)benzamide in MeOH was hydrogenated at 50 PSI in presence of Pd/C (10% by weight) for 5h to afford 2-fluoro-4-hydroxy-5-isopropyl-N-methoxy-N-methylbenzamide.

Step F. To a mixture of 2-fluoro-4-hydroxy-5-isopropyl-N-methoxy-N-methylbenzamide (1 equiv) and pyridine (3 equiv) in DCM (10 mL) was added trifluoromethanesulfonic anhydride (1.5 equiv) dropwise at 0° C. The mixture was stirred at 0° C. for 1 h and washed with saturated NaHCO$_3$ solution and water. The organic phase was dried over MgSO$_4$, concentrated, and purified on a silica gel column to afford 5-fluoro-2-isopropyl-4-(methoxy(methyl)carbamoyl)phenyl trifluoromethanesulfonate as a white solid.

Step G. To a solution of 5-fluoro-2-isopropyl-4-(methoxy(methyl)carbamoyl)phenyl trifluoromethanesulfonate (1 equiv) in 1,4-dioxane (2 mL) was added Intermediate 2A (1.3 equiv), 2M potassium carbonate solution (3 equiv), and Pd(PPh$_3$)$_4$ (0.05 equiv). The mixture was bubbled N$_2$ for 5 min, and then stirred at 90° C. in a sealed tube for 3h. Upon cooling to room temperature, the mixture was poured into NH$_4$Cl solution and extracted with DCM. The organic phase was dried over MgSO$_4$, concentrated, and purified on a silica gel column to afford 5-fluoro-4'-(1,1,1,3,3,3-hexafluoro-2-hydroxypropan-2-yl)-2-isopropyl-N-methoxy-N,2'-dimethyl-[1,1'-biphenyl]-4-carboxamide as a white solid.

Step H. To a solution of 5-fluoro-4'-(1,1,1,3,3,3-hexafluoro-2-hydroxypropan-2-yl)-2-isopropyl-N-methoxy-N,2'-dimethyl-[1,1'-biphenyl]-4-carboxamide (1 equiv) in anhydrous THF (2 mL) was added 1.0 M LAH solution in THF (1.0 equiv) at −78° C. The reaction was stirred at −78° C. for 1 h and quenched by adding EtOAc before being warmed to room temperature. The mixture was poured into NH$_4$Cl solution and extracted with DCM. The organic phase was dried over MgSO$_4$, concentrated, and purified on a silica gel column to afford 5-fluoro-4'-(1,1,1,3,3,3-hexafluoro-2-hydroxypropan-2-yl)-2-isopropyl-2'-methyl-[1,1'-biphenyl]-4-carbaldehyde (Aldehyde Intermediate 12A) as a white solid.

Synthesis of 2'-chloro-5-fluoro-4'-(1,1,1,3,3,3-hexafluoro-2-hydroxypropan-2-yl)-2-isopropyl-[1,1'-biphenyl]-4-carbaldehyde (Aldehyde Intermediate 12D)

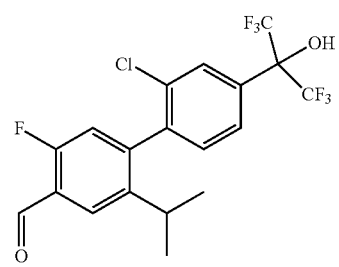 [SMILES: CC(C)c1cc(C=O)c(F)cc1-c1ccc(C(O)(C(F)(F)F)C(F)(F)F)cc1Cl]

Aldehyde Intermediate 12D was prepared using the same procedures used for Aldehyde Intermediate 12A, but substituting Intermediate 2D for Intermediate 2A in Step G.

Example N: Synthesis of Aldehyde Intermediates 13, 13C, and 13D

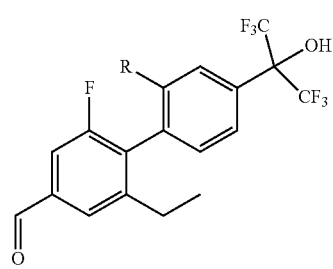

R = H   Aldehyde Intermediate 13
R = F   Aldehyde Intermediate 13C
R = Cl  Aldehyde Intermediate 13D Synthesis of 2-ethyl-6-fluoro-4'-(1,1,1,3,3,3-hexafluoro-2-hydroxypropan-2-yl)-[1,1'-biphenyl]-4-carbaldehyde (Aldehyde Intermediate 13)

Aldehyde Intermediate 13 was prepared using the same procedure described for the synthesis of Aldehyde Intermediate 13A, but substituting 3-fluoro-4-hydroxybenzoic acid for 2-fluoro-4-hydroxybenzoic acid and substituting Intermediate 2 for Intermediate 2A.

Synthesis of 2-ethyl-2',6-difluoro-4'-(1,1,1,3,3,3-hexafluoro-2-hydroxypropan-2-yl)-[1,1'-biphenyl]-4-carbaldehyde (Aldehyde Intermediate 13C)

Aldehyde Intermediate 13C as prepared using the same procedure described for the synthesis of Aldehyde Intermediate 12A, but substituting 3-fluoro-4-hydroxybenzoic acid for 2-fluoro-4-hydroxybenzoic acid and substituting Intermediate 2C for Intermediate 2A.

Synthesis of 2'-chloro-2-ethyl-6-fluoro-4'-(1,1,1,3,3,3-hexafluoro-2-hydroxypropan-2-yl)-[1,1'-biphenyl]-4-carbaldehyde (Aldehyde Intermediate 13D)

Aldehyde Intermediate 13D as prepared using the same procedure described for the synthesis of Aldehyde Intermediate 12A, but substituting 3-fluoro-4-hydroxybenzoic acid for 2-fluoro-4-hydroxybenzoic acid and substituting Intermediate 2D for Intermediate 2A.

Example O: Synthesis of 2'-chloro-2-ethyl-5-fluoro-4'-(1,1,1,3,3,3-hexafluoro-2-hydroxypropan-2-yl)-[1,1'-biphenyl]-4-carbaldehyde (Aldehyde Intermediate 14)

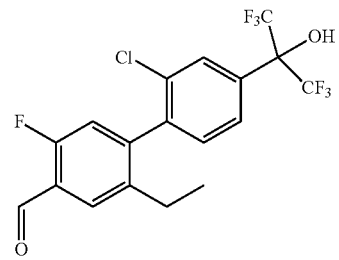 [SMILES: CCc1cc(C=O)c(F)cc1-c1ccc(C(O)(C(F)(F)F)C(F)(F)F)cc1Cl]

Aldehyde Intermediate 14 was prepared using the same procedure described for Aldehyde Intermediate 12A, but substituting 4,4,5,5-tetramethyl-2-vinyl-1,3,2-dioxaborolane for 4,4,5,5-tetramethyl-2-(prop-1-en-2-yl)-1,3,2-dioxaborolane in Step D.

Example P: Synthesis of Amine Intermediates 1A-1G

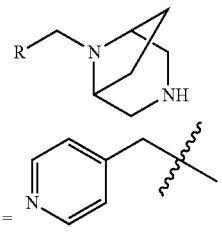

Amine Intermediate 1A

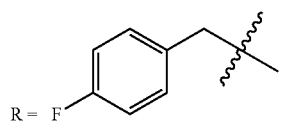

Amine Intermediate 1B

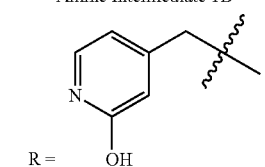

Amine Intermediate 1C

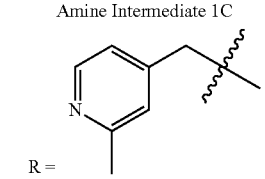

Amine Intermediate 1D

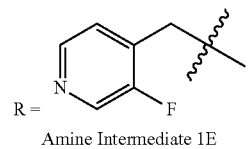

Amine Intermediate 1E

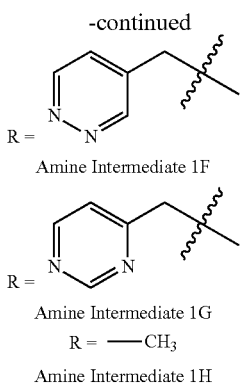

R = [pyridazin-4-ylmethyl]  Amine Intermediate 1F

R = [pyrimidin-4-ylmethyl]  Amine Intermediate 1G

R = —CH₃  Amine Intermediate 1H

Synthesis of 8-(pyridin-4-ylmethyl)-3,8-diazabicyclo[3.2.1]octane TFA (Amine Intermediate 1A)

Step A. tert-Butyl 3,8-diazabicyclo[3.2.1]octane-3-carboxylate (1.0 equiv) and isonicotinaldehyde (1.2 equiv) were combined in 1,2-DCE. To the mixture was added acetic acid (0.1 equiv). The mixture was stirred at rt for 3h. NaBH(OAc)₃ (3.0 equiv) was then added into the reaction mixture. The resulting mixture was stirred at rt overnight. The reaction mixture was quenched with MeOH (30 mL) and washed with saturated NaHCO₃, water, and brine. The crude mixture was purified on a silica gel column to afford tert-butyl 8-(pyridin-4-ylmethyl)-3,8-diazabicyclo[3.2.1]octane-3-carboxylate.

Step B. tert-Butyl 8-(pyridin-4-ylmethyl)-3,8-diazabicyclo[3.2.1]octane-3-carboxylate (1.0 equiv) was dissolved in CH₂Cl₂ (1 mL) and TFA (1 mL) was added. The mixture was stirred at rt for 2h. The solvent was removed in vacuo to afford 8-(pyridin-4-ylmethyl)-3,8-diazabicyclo[3.2.1]octane (Amine Intermediate 1A) as a TFA salt.

Synthesis of 8-(4-fluorobenzyl)-3,8-diazabicyclo[3.2.1]octane TFA (Amine Intermediate 1B)

Amine Intermediate 1B was prepared using the same procedure above, but substituting 4-fluorobenzaldehyde for isconicotinaldehyde in Step A.

Synthesis of 4-((3,8-diazabicyclo[3.2.1]octan-8-yl)methyl)pyridin-2-ol TFA (Amine Intermediate 1C)

Amine Intermediate 1C was prepared using the same procedure above, but substituting 2-hydroxyisonicotinaldehyde for isconicotinaldehyde in Step A.

Synthesis of 8-((2-methylpyridin-4-yl)methyl)-3,8-diazabicyclo[3.2.1]octane TFA (Amine Intermediate 1D)

Amine Intermediate 1D was prepared using the same procedure above, but substituting 2-methylisonicotinaldehyde for isconicotinaldehyde in Step A.

Synthesis of 8-((3-fluoropyridin-4-yl)methyl)-3,8-diazabicyclo[3.2.1]octane TFA (Amine Intermediate 1E)

Amine Intermediate 1E was prepared using the same procedure above, but substituting 3-fluoroisonicotinaldehyde for isconicotinaldehyde in Step A.

Synthesis of 8-(pyridazin-4-ylmethyl)-3,8-diazabicyclo[3.2.1]octane TFA (Amine Intermediate 1F)

Amine Intermediate 1F was prepared using the same procedure above, but substituting pyridazine-4-carbaldehyde for isconicotinaldehyde in Step A.

Synthesis of 8-(pyrimidin-4-ylmethyl)-3,8-diazabicyclo[3.2.1]octane TFA (Amine Intermediate 1G)

Amine Intermediate 1B was prepared using the same procedure above, but substituting pyrimidine-4-carbaldehyde for isconicotinaldehyde in Step A.

Synthesis of 8-ethyl-3,8-diazabicyclo[3.2.1]octane TFA (Amine Intermediate 1H)

Amine Intermediate 1B was prepared using the same procedure above, but substituting acetaldehyde for isconicotinaldehyde in Step A.

Example Q: Synthesis of Amine Intermediates 2A-2G

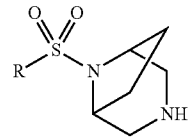

| | |
|---|---|
| R = —CH₃ | Amine Intermediate 2A |
| R = —CH₂CH₃ | Amine Intermediate 2B |
| R = —CH₂CH₂CH₃ | Amine Intermediate 2C |
| R = cyclopropyl | Amine Intermediate 2D |
| R = —CF₃ | Amine Intermediate 2E |
| R = —CH₂CF₃ | Amine Intermediate 2F |

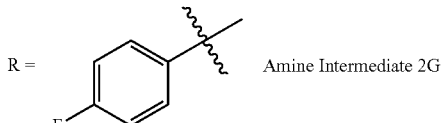

R =  Amine Intermediate 2G

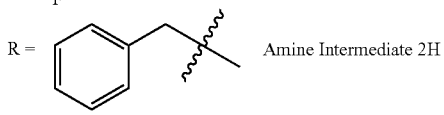

R =  Amine Intermediate 2H

Synthesis of 8-(methylsulfonyl)-3,8-diazabicyclo[3.2.1]octane TFA (Amine Intermediate 2A)

tert-Butyl 3,8-diazabicyclo[3.2.1]octane-3-carboxylate (1.0 equiv) was dissolved in 5 mL DCM. To the solution was added 2 mL saturated NaHCO₃ and methanesulfonyl chloride. The mixture was stirred at 0° C. MsCl (2.0 equiv) was added. The resulting mixture was stirred at rt for overnight. The organic phase was separated and washed with 1N HCl and brine to afford tert-butyl 8-(methylsulfonyl)-3,8-diazabicyclo[3.2.1]octane-3-carboxylate (>95% yield). To a solution of tert-butyl 8-(methylsulfonyl)-3,8-diazabicyclo[3.2.1]octane-3-carboxylate in 2 mL DCM was added 2 mL TFA. The mixture was stirred at rt for 2h. The solvent was removed in high vacuo to afford 8-(methylsulfonyl)-3,8-diazabicyclo[3.2.1]octane (Amine Intermediate 2A) as a TFA salt which was used without further purification.

Synthesis of 8-(ethylsulfonyl)-3,8-diazabicyclo[3.2.1]octane TFA (Amine Intermediate 2B)

Amine Intermediate 2B was prepared using the procedure as above, but substituting ethanesulfonyl chloride for methanesulfonyl chloride.

Synthesis of 8-(propylsulfonyl)-3,8-diazabicyclo[3.2.1]octane TFA (Amine Intermediate 2C)

Amine Intermediate 2B was prepared using the procedure as above, but substituting propane-1-sulfonyl chloride for methanesulfonyl chloride.

Synthesis of 8-(cyclopropylsulfonyl)-3,8-diazabicyclo[3.2.1]octane TFA (Amine Intermediate 2D)

Amine Intermediate 2B was prepared using the procedure as above, but substituting cyclopropanesulfonyl chloride for methanesulfonyl chloride.

Synthesis of 8-((trifluoromethyl)sulfonyl)-3,8-diazabicyclo[3.2.1]octane TFA (Amine Intermediate 2E)

Amine Intermediate 2B was prepared using the procedure as above, but substituting trifluoromethanesulfonyl chloride for methanesulfonyl chloride.

Synthesis of 8-((2,2,2-trifluoroethyl)sulfonyl)-3,8-diazabicyclo[3.2.1]octane TFA (Amine Intermediate 2F)

Amine Intermediate 2B was prepared using the procedure as above, but substituting 2,2,2-trifluoroethane-1-sulfonyl chloride for methanesulfonyl chloride.

Synthesis of (8-((4-fluorophenyl)sulfonyl)-3,8-diazabicyclo[3.2.1]octane TFA Amine Intermediate 2G)

Amine Intermediate 2B was prepared using the procedure as above, but substituting 4-fluorobenzenesulfonyl chloride for methanesulfonyl chloride.

Synthesis of 8-(benzylsulfonyl)-3,8-diazabicyclo[3.2.1]octane TFA (Amine Intermediate 2H)

Amine Intermediate 2B was prepared using the procedure as above, but substituting phenylmethanesulfonyl chloride for methanesulfonyl chloride.

Example R: Synthesis of Amine Intermediates 3A-3G

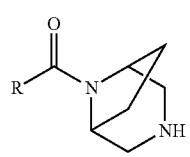

R = —CH₃  Amine Intermediate 3A
R = —CH₂OCH₃  Amine Intermediate 3B
R = —CH₂OCH₂OCH₃  Amine Intermediate 3C

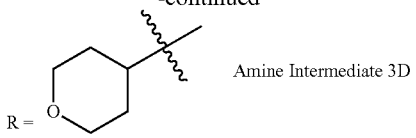  Amine Intermediate 3D

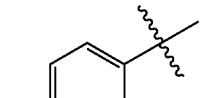  Amine Intermediate 3E

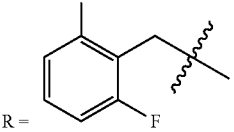  Amine Intermediate 3F

Amine Intermediate 3G

Synthesis of 1-(3,8-diazabicyclo[3.2.1]octan-8-yl)ethan-1-one (Amine Intermediate 3A)

tert-Butyl 3,8-diazabicyclo[3.2.1]octane-3-carboxylate (1.0 equiv) and DIEA (2.0 equiv) were combined in 5 mL DCM. The mixture was cooled to 0° C. To the mixture was added acetyl chloride (1.5 equiv). The resulting mixture was stirred at rt for 5h. The mixture was washed with saturated NaHCO₃, water, 1N HCl and brine to afford tert-butyl 8-acetyl-3,8-diazabicyclo[3.2.1]octane-3-carboxylate (yield 85%). To a solution of tert-butyl 8-acetyl-3,8-diazabicyclo[3.2.1]octane-3-carboxylate in 1 mL DCM was added 1 mL TFA. The mixture was stirred at rt for 1 h. The solvent was removed in high vacuo to afford (Amine Intermediate 3A) as TFA salt which was used without further purification.

Synthesis of 1-(3,8-diazabicyclo[3.2.1]octan-8-yl)-2-methoxyethan-1-one TFA(Amine Intermediate 3B)

Amine Intermediate 3B was prepared using the procedure above, but substituting 2-methoxyacetyl chloride for acetyl chloride.

Synthesis of 1-(3,8-diazabicyclo[3.2.1]octan-8-yl)-3-methoxypropan-1-one TFA (Amine Intermediate 3C)

Amine Intermediate 3C was prepared using the procedure above, but substituting 3-methoxypropanoyl chloride for acetyl chloride.

Synthesis of (3,8-diazabicyclo[3.2.1]octan-8-yl)(tetrahydro-2H-pyran-4-yl)methanone TFA (Amine Intermediate 3D)

Amine Intermediate 3C was prepared using the procedure above, but substituting tetrahydro-2H-pyran-4-carbonyl chloride for acetyl chloride.

Synthesis of ethyl 3,8-diazabicyclo[3.2.1]octane-8-carboxylate TFA (Amine Intermediate 3E)

Amine Intermediate 3C was prepared using the procedure above, but substituting ethyl carbonochloridate for acetyl chloride.

Synthesis of (3,8-diazabicyclo[3.2.1]octan-8-yl)(pyridin-4-yl)methanone (Amine Intermediate 3F)

Amine Intermediate 3C was prepared using the procedure above, but substituting isonicotinoyl chloride for acetyl chloride.

Synthesis of 1-(3,8-diazabicyclo[3.2.1]octan-8-yl)-2-(2,6-difluorophenyl)ethan-1-one (Amine Intermediate 3G)

Amine Intermediate 3C was prepared using the procedure above, but substituting 2-(2,6-difluorophenyl)acetyl chloride for acetyl chloride.

Example S: Synthesis of 3-(3,8-diazabicyclo[3.2.1]octan-8-yl)-5-(tert-butyl)-1,2,4-oxadiazole (Amine Intermediate 4)

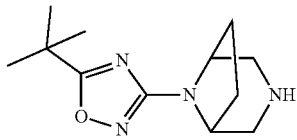 [SMILES: CC(C)(C)c1nc(N2C3CCC2CNC3)no1]

To a solution of tert-butyl 3,8-diazabicyclo[3.2.1]octane-3-carboxylate (1.0 equiv) and DIEA (2.0 equiv) in dry DCM at 0° C. was added BrCN (1.5 equiv). The mixture was stirred at 0° C. for 1 h and then at rt overnight. The reaction mixture was washed with water and brine to afford tert-butyl 8-cyano-3,8-diazabicyclo[3.2.1]octane-3-carboxylate which was used without further purification.

To a solution of tert-butyl 8-cyano-3,8-diazabicyclo[3.2.1]octane-3-carboxylate (1.0 equiv) in EtOH was added TEA (1.3 equiv) and hydroxylamine HCl salt (1.1 equiv) at rt. The resulting mixture was heated at 80° C. for 1h. The mixture was cooled to rt, diluted with EtOAc, and washed with water and brine. The crude was purified on a silica gel column to afford tert-butyl 8-(N-hydroxycarbamimidoyl)-3,8-diazabicyclo[3.2.1]octane-3-carboxylate.

tert-Butyl 8-(N-hydroxycarbamimidoyl)-3,8-diazabicyclo[3.2.1]octane-3-carboxylate (1.0 equiv) and pivalic anhydride (1.1 equiv) were combined in dry DMF. The mixture was stirred at rt for 1 h, then heated at 80° C. for 14h. The mixture was diluted with acetate and washed with saturated NaHCO₃. The crude product was purified on a silica gel column to afford tert-butyl 8-(5-(tert-butyl)-1,2,4-oxadiazol-3-yl)-3,8-diazabicyclo[3.2.1]octane-3-carboxylate (Amine Intermediate 4).

tert-Butyl 8-(5-(tert-butyl)-1,2,4-oxadiazol-3-yl)-3,8-diazabicyclo[3.2.1]octane-3-carboxylate was dissolved in 2 mL DCM, added 2 mL TFA. The mixture was stirred at rt for 1 h to afford Amine Intermediate 4 as a TFA salt which was used without further purification Example T: Synthesis of 2-(methylsulfonyl)-2,5-diazabicyclo[2.2.2]octane (Amine Intermediate 5)

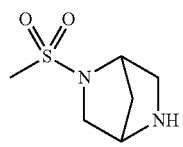

Amine Intermediate 5 was prepared using the same procedure for Amine Intermediate 2A, but substituting tert-butyl 2,5-diazabicyclo[2.2.2]octane-2-carboxylate for tert-butyl 3,8-diazabicyclo[3.2.1]octane-3-carboxylate.

Example U: Synthesis of 2-(methylsulfonyl)-2,5-diazabicyclo[2.2.2]octane (Amine Intermediate 6)

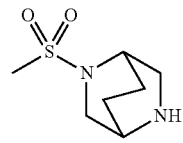

Amine Intermediate 6 was prepared using the same procedure for Amine Intermediate 2A, but substituting tert-butyl 2,5-diazabicyclo[2.2.2]octane-2-carboxylate for tert-butyl 3,8-diazabicyclo[3.2.1]octane-3-carboxylate Example V: Synthesis of N-(3-azabicyclo[3.2.1]octan-8-yl)methanesulfonamide (Amine Intermediate 7)

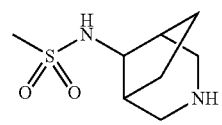

Amine Intermediate 7 was prepared using the same procedure as Amine Intermediate 2A, but substituting tert-butyl 8-amino-3-azabicyclo[3.2.1]octane-3-carboxylate for tert-butyl 3,8-diazabicyclo[3.2.1]octane-3-carboxylate Example W: Synthesis of (1R,5S)-9-(methylsulfonyl)-3-oxa-7,9-diazabicyclo[3.3.1]nonane (Amine Intermediate 8)

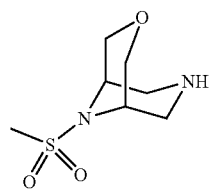

Amine Intermediate 8 was prepared using the same procedure as Amine Intermediate 2A, but substituting tert-butyl (1R,5S)-3-oxa-7,9-diazabicyclo[3.3.1]nonane-7-carboxylate for tert-butyl 3,8-diazabicyclo[3.2.1]octane-3-carboxylate Example X: Synthesis of 2-(pyridin-4-ylmethyl)-2,5-diazabicyclo[2.2.1]heptane (Amine Intermediate 9)

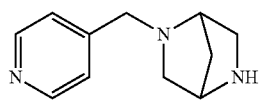 [SMILES: c1cc(CN2CC3CC2CN3)ccn1]

Amine Intermediate 9 was prepared using the same procedure as Amine Intermediate 1A but substituting tert-butyl 2,5-diazabicyclo[2.2.1]heptane-2-carboxylate for tert-butyl 3,8-diazabicyclo[3.2.1]octane-3-carboxylate.

Example Y: Synthesis of 2-(pyridin-4-ylmethyl)-2,5-diazabicyclo[2.2.2]octane (Amine Intermediate 10)

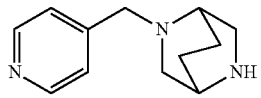 [SMILES: c1cc(CN2CC3CCC2CN3)ccn1]

Amine Intermediate 10 was prepared using the same procedure as Amine Intermediate 1A, but substituting tert-butyl 2,5-diazabicyclo[2.2.2]octane-2-carboxylate for tert-butyl 3,8-diazabicyclo[3.2.1]octane-3-carboxylate.

Example 1: Synthesis of 1,1,1,3,3,3-hexafluoro-2-(4'-((8-(pyridin-4-ylmethyl)-3,8-diazabicyclo[3.2.1]octan-3-yl)methyl)-[1,1'-biphenyl]-4-yl)propan-2-ol

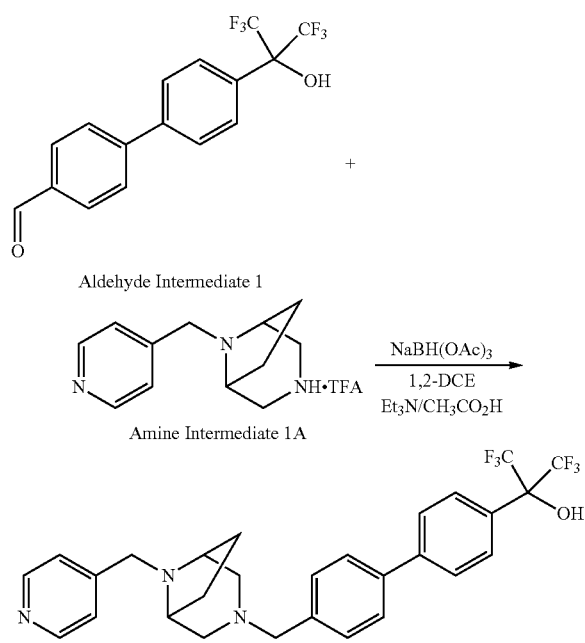

8-(Pyridin-4-ylmethyl)-3,8-diazabicyclo[3.2.1]octane TFA salt (1.2 equiv) was suspended into 5 mL 1,2-DCE, added Et₃N (3.0 equiv) and stirred at rt for 30 min. 4'-(1,1,1,3,3,3-hexafluoro-2-hydroxypropan-2-yl)-[1,1'-biphenyl]-4-carbaldehyde (Aldehyde Intermediate 1) (1.0 equiv) was added followed by acetic acid (1.0 equiv). The mixture was stirred at rt for 3h, Solid NaBH(OAc) (3.0 equiv) was added to the solution. The resulting mixture was stirred at rt overnight. The reaction was quenched with MeOH, and diluted with 20 mL saturated NaHCO₃ extracted with 2×20 mL ethyl acetate. The crude mixture was purified on a silica gel column to afford title compound as a white solid. LC-MS (ESI) m/z (M+H)⁺ 536.4.

Example 2: Synthesis of 1,1,1,3,3,3-hexafluoro-2-(4'-((3-(pyridin-4-ylmethyl)-3,8-diazabicyclo[3.2.1]octan-8-yl)methyl)-[1,1'-biphenyl]-4-yl)propan-2-ol

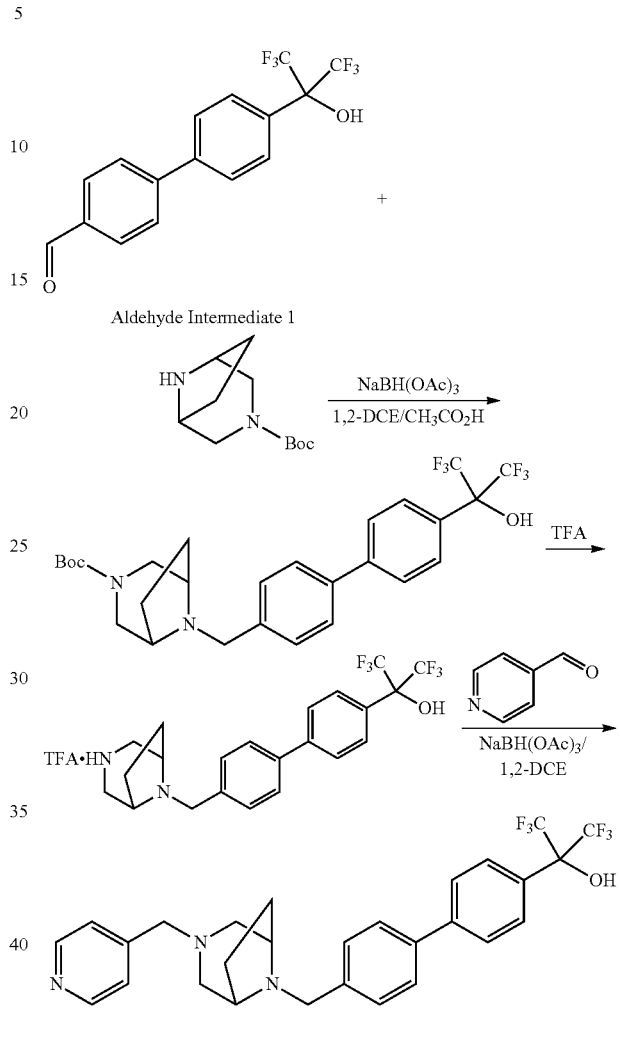

4'-(1,1,1,3,3,3-hexafluoro-2-hydroxypropan-2-yl)-[1,1'-biphenyl]-4-carbaldehyde (Aldehyde Intermediate 1) (1.0 equiv) and tert-butyl 3,8-diazabicyclo[3.2.1]octane-3-carboxylate (1.0 equiv) were combined into 1,2-DCE (5 mL). To the mixture was added acetic acid (0.5 equiv) was added. The mixture was stirred at rt for 3h. Solid NaBH(OAc)₃ (3.0 equiv) was then added into the reaction. The resulting mixture was stirred at rt overnight. The reaction was quenched with MeOH (10 mL) and washed with saturated NaHCO₃, water and brine. The crude mixture was purified on a silica gel column to afford tert-butyl 8-((4'-(1,1,1,3,3,3-hexafluoro-2-hydroxypropan-2-yl)-[1,1'-biphenyl]-4-yl)methyl)-3,8-diazabicyclo[3.2.1]octane-3-carboxylate (yield 65%) as a white solid.

To a solution of tert-butyl 8-((4'-(1,1,1,3,3,3-hexafluoro-2-hydroxypropan-2-yl)-[1,1'-biphenyl]-4-yl)methyl)-3,8-diazabicyclo[3.2.1]octane-3-carboxylate in 2 mL DCM was added 2 mL TFA. The mixture was stirred at rt for 1h. The solvent was removed in high vacuo to afford 2-(4'-((3,8-Diazabicyclo[3.2.1]octan-8-yl)methyl)-[1,1'-biphenyl]-4-yl)-1,1,1,3,3,3-hexafluoropropan-2-ol as TFA salt which was used without further purification.

2-(4'-((3,8-Diazabicyclo[3.2.1]octan-8-yl)methyl)-[1,1'-biphenyl]-4-yl)-1,1,1,3,3,3-hexafluoropropan-2-ol TFA (1.0 equiv) and isonicotinaldehyde (1.2 equiv) were combined in 1,2-DCE. The mixture was stirred at rt for 3h. Solid NaBH(OAc)₃ (3.0 equiv) was then added into the reaction mixture. The resulting mixture was stirred at rt overnight. The reaction mixture was quenched with MeOH (30 mL) and washed with saturated NaHCO₃, water, and brine. The crude mixture was purified on a silica gel column to afford the title compound as a white solid. LC-MS (ESI) m/z (M+H)+: 536.3.

Example 3: Synthesis of 2-(4-(4-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol

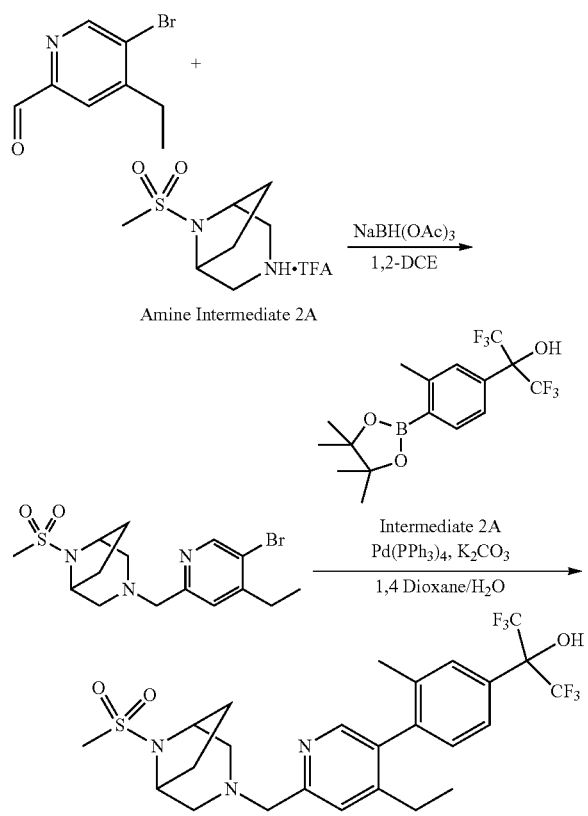

Step A. 5-bromo-4-ethylpicolinaldehyde (1.0 equiv) and 8-(methylsulfonyl)-3,8-diazabicyclo[3.2.1]octane TFA salt (Amine Intermediate 2A) (1.3 equiv) were combined into 5 mL 1,2-DCE. The mixture was stirred at rt for 3h. Solid NaBH(OAc)₃ (3.0 equiv) was then added into the reaction. The resulting mixture was stirred at rt overnight. The reaction was quenched with MeOH (10 mL) and washed with saturated NaHCO₃, water, and brine. The crude mixture was purified on a silica gel column to afford 3-((5-bromo-4-ethylpyridin-2-yl)methyl)-8-(methylsulfonyl)-3,8-diazabicyclo[3.2.1]octane (yield 72%) as a white solid.

Step B. 3-((5-Bromo-4-ethylpyridin-2-yl)methyl)-8-(methylsulfonyl)-3,8-diazabicyclo[3.2.1]octane (1.0 equiv), Intermediate 2A (1.3 equiv), Pd(PPh₃)₄ (0.1 equiv) and K₂CO₃ (3.0 equiv) were combined in 8 mL dioxane and 4 mL water. The mixture was flushed with N₂ for 5 min, and then heated at 95° C. for 14h under N₂. The reaction was extracted with EtOAc (2×30 mL). The combined organic phase was washed with brine. The crude mixture was purified on a silica gel column to afford the title compound (yield 48%) as a white solid. LC-MS (ESI) m/z (M+H)+: 566.5.

Example 4: Synthesis of 2-(3-chloro-4-(4-ethyl-6-((8-(methylsulfonyl)-3,8-diazabicyclo[3.2.1]octan-3-yl)methyl)pyridin-3-yl)phenyl)-1,1,1,3,3,3-hexafluoropropan-2-ol

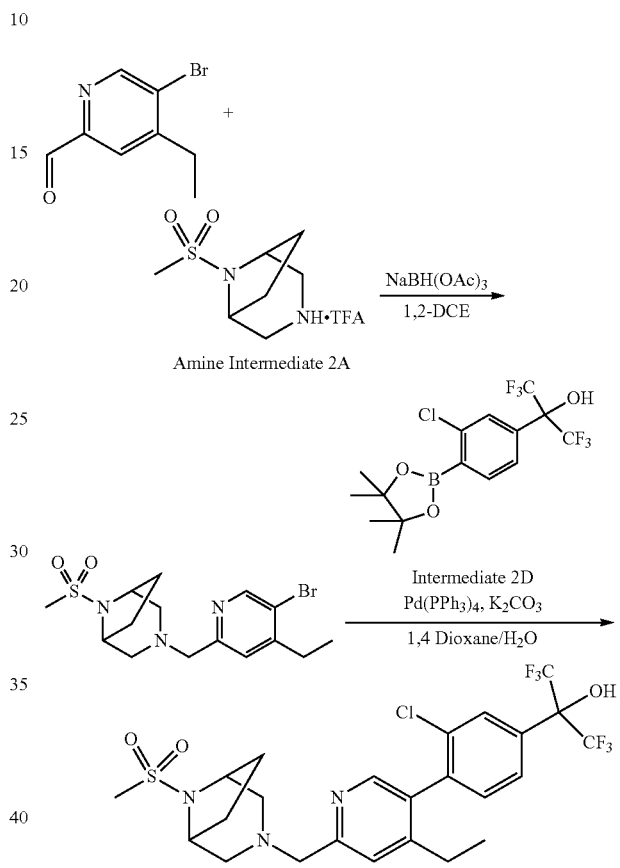

The title compound was prepared using the procedure described in Example 3, but substituting Intermediate 2D for Intermediate 2A in Step B. LC-MS (ESI) m/z (M+H)+: 586.3.

Example 5: Synthesis of 2-(4-(2-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol

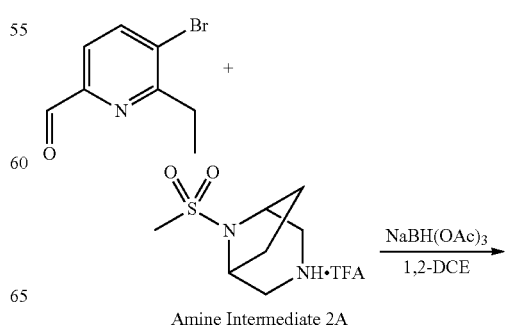

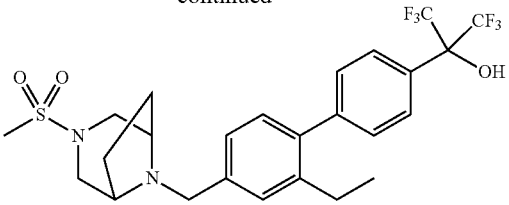

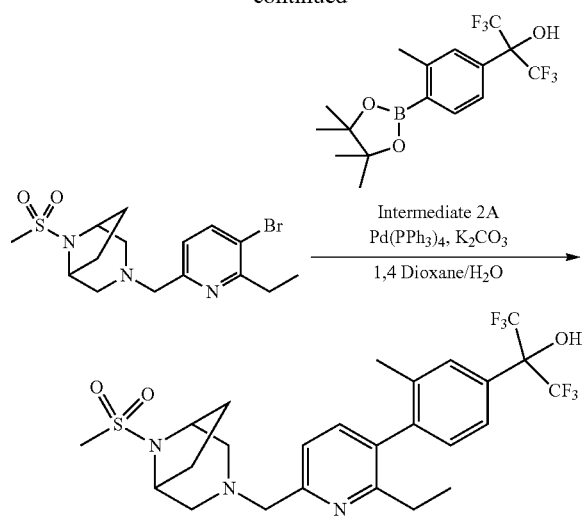

The title compound was prepared using the procedure described in Example 3, but substituting 5-bromo-6-ethylpicolinaldehyde for 5-bromo-4-ethylpicolinaldehyde in Step A. LC-MS (ESI) m/z (M+H)+: 566.5.

Example 6: Synthesis of 2-(2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol

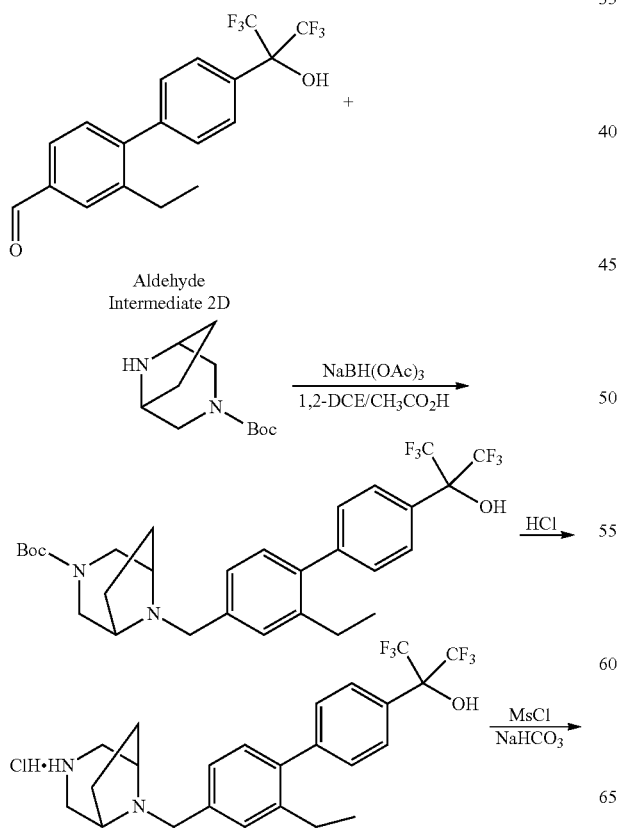

Aldehyde Intermediate 2 (1.0 equiv) and tert-butyl 3,8-diazabicyclo[3.2.1]octane-3-carboxylate (1.2 equiv) were combined into 1,2-DCE (5 mL). To the mixture was added acetic acid (0.5 equiv). The mixture was stirred at rt for 3h. Solid NaBH(OAc)$_3$ (3.0 equiv) was then added into the reaction. The resulting mixture was stirred at rt overnight. The reaction was quenched with MeOH (10 mL) and washed with saturated NaHCO$_3$, water, and brine. The crude mixture was purified on a silica gel column to afford tert-butyl 8-((2-ethyl-4'-(1,1,1,3,3,3-hexafluoro-2-hydroxypropan-2-yl)-[1,1'-biphenyl]-4-yl)methyl)-3,8-diazabicyclo[3.2.1]octane-3-carboxylate (yield 55%) as a white solid.

To a solution of tert-butyl 8-((2-ethyl-4'-(1,1,1,3,3,3-hexafluoro-2-hydroxypropan-2-yl)-[1,1'-biphenyl]-4-yl)methyl)-3,8-diazabicyclo[3.2.1]octane-3-carboxylate in 1 mL DCM was added 3 mL 4N HCl in dioxane. The mixture was stirred at rt for 3h. The solvent was removed in high vacuo to 2-(4'-((3,8-diazabicyclo[3.2.1]octan-8-yl)methyl)-2'-ethyl-[1,1'-biphenyl]-4-yl)-1,1,1,3,3,3-hexafluoropropan-2-ol as HCl salt which was used without further purification.

2-(4'-((3,8-diazabicyclo[3.2.1]octan-8-yl)methyl)-2'-ethyl-[1,1'-biphenyl]-4-yl)-1,1,1,3,3,3-hexafluoropropan-2-ol HCl was suspended into 5 mL DCM and 3 mL saturated NaHCO$_3$. The mixture was stirred at rt for 15 min. To the mixture was added MsCl (5.0 equiv). The resulting mixture was stirred at rt for 2h. The reaction was quenched with 2 mL saturated NH$_4$OH. The mixture was stirred at rt for 10 min. The organic phase was separated and washed with water and brine. The crude mixture was purified on a silica gel column to afford the title compound as a white solid. LC-MS (ESI) m/z (M+H)+ 551.5.

Example 7: Synthesis of 2-(2-chloro-2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol

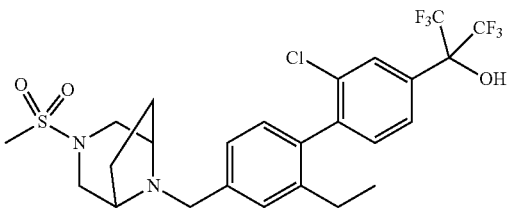 [SMILES: CCc1cc(CN2C3CCC2CN(S(C)(=O)=O)C3)ccc1-c1ccc(C(O)(C(F)(F)F)C(F)(F)F)cc1Cl]

The title compound was prepared using the procedure described in Example 6, but substituting Intermediate 2D for Intermediate 2, in Step A. LC-MS (ESI) m/z (M+H)+: 585.2.

Example 8: Synthesis of 2-(2'-ethyl-4'-(((1R,5S)-7-(methylsulfonyl)-3-oxa-7,9-diazabicyclo[3.3.1]nonan-9-yl)methyl)-[1,1'-biphenyl]-4-yl)-1,1,1,3,3,3-hexafluoropropan-2-ol

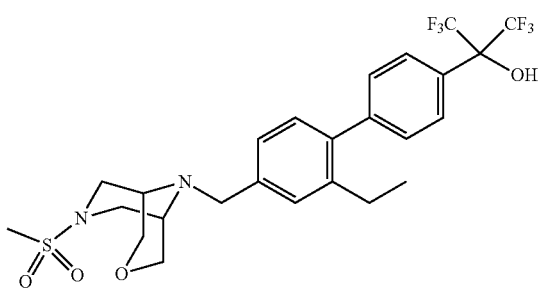 [SMILES: CCc1cc(CN2C3COCC2CN(S(C)(=O)=O)C3)ccc1-c1ccc(C(O)(C(F)(F)F)C(F)(F)F)cc1]

The title compound was prepared using the procedure described in Example 6, but substituting tert-butyl (1R,5S)-3-oxa-7,9-diazabicyclo[3.3.1]nonane-7-carboxylate for tert-butyl 3,8-diazabicyclo[3.2.1]octane-3-carboxylate in Step A. LC-MS (ESI) m/z (M+H)$^+$: 567.4.

Example 9: Synthesis of 1,1,1,3,3,3-hexafluoro-2-(3'-(8-(methylsulfonyl)-3,8-diazabicyclo[3.2.1]octan-3-yl)-[1,1'-biphenyl]-4-yl)propan-2-ol

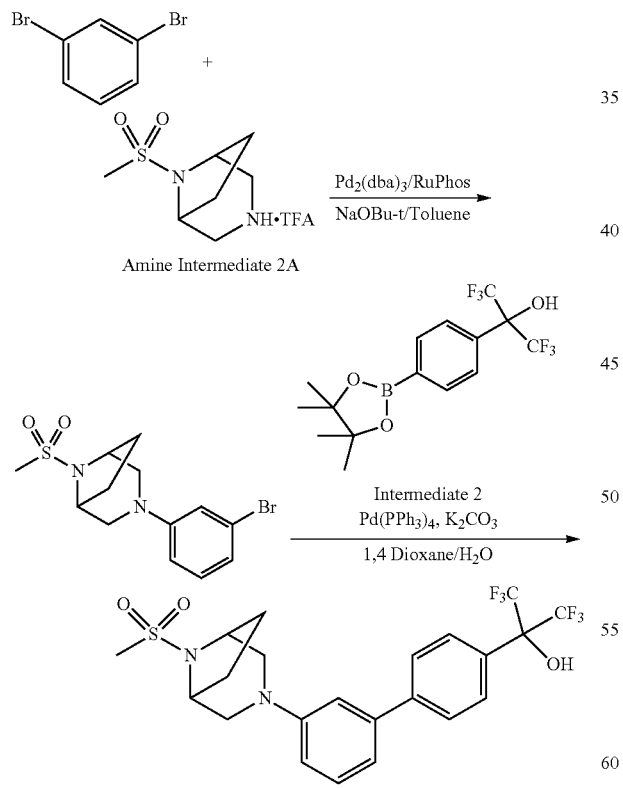

1,3-dibromobenzene (1.2 equiv) and Amine Intermediate 2A (1.0 equiv) were suspended into 5 mL dry toluene and Pd$_2$(dba)$_3$ (0.05 equiv), RuPhos (0.1 equiv), and sodium t-butyloxide (3.5 equiv) were added. N$_2$ was bubbled into the mixture for 5 min. The resulting mixture was heated at 100° C. for 5h. The solvent was removed in high vacuum. The residue was purified on a silica gel column with solid loading to afford 3-(3-bromophenyl)-8-(methylsulfonyl)-3,8-diazabicyclo[3.2.1]octane.

Standard Suzuki coupling between 3-(3-bromophenyl)-8-(methylsulfonyl)-3,8-diazabicyclo[3.2.1]octane and Intermediate 2 afforded the title compound. LC-MS (ESI) m/z (M+H)$^+$: 509.3.

Example 10: Synthesis of 2-(2-chloro-2'-ethyl-3',5'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol

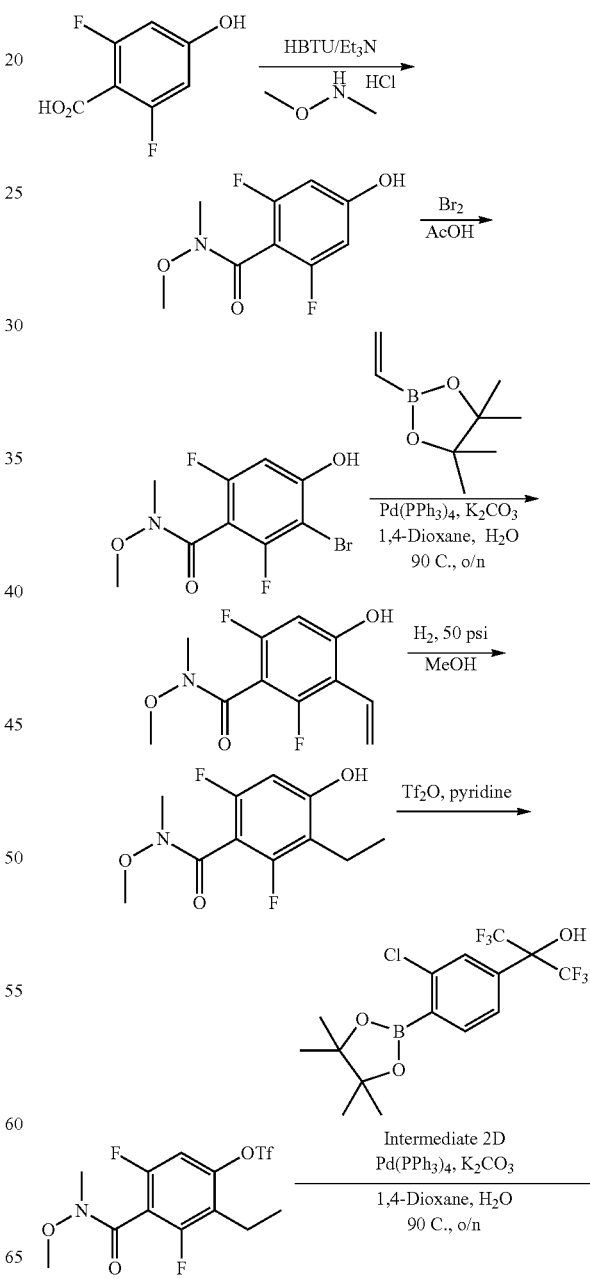

-continued

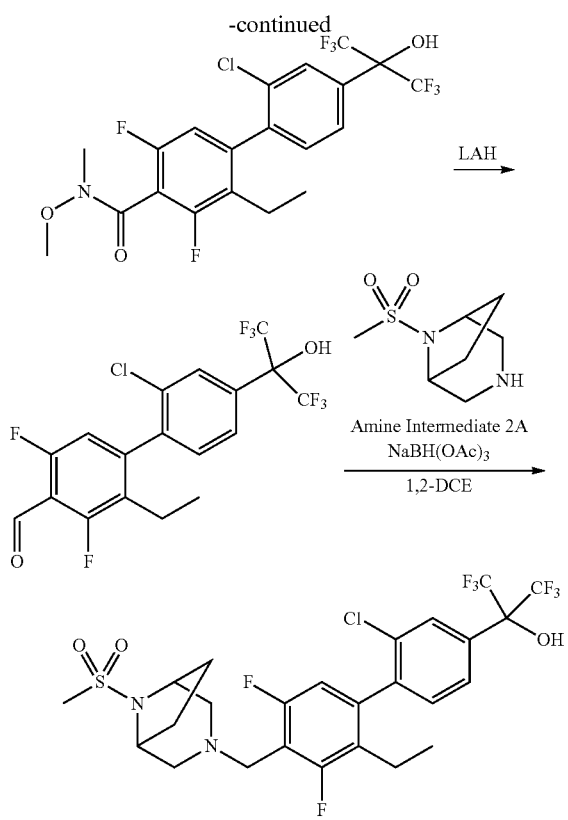

To a mixture of 2,6-difluoro-4-hydroxybenzoic acid (5.0 g, 1.0 equiv), triethylamine (12 mL, 3 equiv) and N, O-dimethylhydroxylamine hydrochloride (4.2 g, 1.5 equiv) in DMA (100 mL) was added HBTU (12 g, 1.1 equiv). The mixture was stirred at room temperature for 4h. Additional HBTU (4.4 g, 0.4 equiv) was added. The reaction was diluted with EtOAc-hexane (v/v 80/20, 3×80 mL) and washed with 1N HCl (2×150 mL). The organic phase was dried over $MgSO_4$, concentrated, and purified on a silica gel column to afford 2,6-difluoro-4-hydroxy-N-methoxy-N-methylbenzamide (4.7 g, 75% yield) as a white solid.

To a stirred solution of 2,6-difluoro-4-hydroxy-N-methoxy-N-methylbenzamide (4.7 g, 1.0 equiv) in acetic acid (50 mL) was added $Br_2$ (5.2 g, 1.5 equiv) dropwise at 0° C. The reaction was warmed up to room temperature, and then stirred at 40° C. for 1 h. The reaction mixture was concentrated under vacuum. The residue was directly purified on a silica gel column to afford 3-bromo-2,6-difluoro-4-hydroxy-N-methoxy-N-methylbenzamide (4.0 g, yield 61%) as white solid.

To a solution of 3-bromo-2,6-difluoro-4-hydroxy-N-methoxy-N-methylbenzamide (4.0 g, 1 equiv) in 1,4-dioxane (60 mL) and water (20 mL) was added 4,4,5,5-tetramethyl-2-vinyl-1,3,2-dioxaborolane (4.1 g, 2.0 equiv), potassium carbonate (4.7 g, 2.5 equiv), and $Pd(PPh_3)_4$ (0.8 g, 0.05 equiv). The mixture bubbled with $N_2$ for 10 min, and then stirred at 90° C. overnight (20h). Upon cooling to room temperature, 1N HCl (150 mL) was added, and the mixture was extracted with DCM (2×200 mL). The organic phase was dried over $MgSO_4$, concentrated, and purified with column to afford 2,6-difluoro-4-hydroxy-N-methoxy-N-methyl-3-vinylbenzamide (1.05 g, 32% yield) as a white solid.

To a solution of 2,6-difluoro-4-hydroxy-N-methoxy-N-methyl-3-vinylbenzamide (1.0 g, 1.0 equiv) in MeOH (30 mL) was added Pd/C (10% wt., 200 mg). The reaction was hydrogenated under $H_2$ (50 psi) for 18h. The mixture was filtered through celite pad to remove catalyst and concentrated. The crude mixture was purified by silica gel column to afford 3-ethyl-2,6-difluoro-4-hydroxy-N-methoxy-N-methylbenzamide (0.65 g, ~65% yield) as an oil.

To a solution of 3-ethyl-2,6-difluoro-4-hydroxy-N-methoxy-N-methylbenzamide (0.64 g, 1 equiv) and pyridine (0.7 mL, 3.0 equiv) in DCM (20 mL) was added trifluoromethanesulfonic anhydride (1.1 g, 1.5 equiv) dropwise at 0° C. The mixture was stirred at 0° C. for 30 min and washed with saturated $NaHCO_3$ solution, 1N HCl, and water. The organic phase was dried over $MgSO_4$, concentrated, and purified by silica gel column to afford 2-ethyl-3,5-difluoro-4-(methoxy(methyl)carbamoyl)phenyl trifluoromethanesulfonate (0.93 g, 95% yield) as a pale yellow oil.

To a solution of 2-ethyl-3,5-difluoro-4-(methoxy(methyl)carbamoyl)phenyl trifluoromethanesulfonate (0.9 g, 1 equiv) in 1,4-dioxane (40 mL) and water (10 mL) was added 2-(3-chloro-4-(4,4,5,5-tetramethyl-1,3,2-dioxaborolan-2-yl)phenyl)-1,1,1,3,3,3-hexafluoropropan-2-ol (Intermediate 2D) (1.25 g, 1.3 equiv), potassium carbonate (0.66 g, 2 equiv), and $Pd(PPh_3)_4$ (0.28 g, 0.1 equiv). The mixture was degassed and then bubbled with $N_2$ for 10 min, and then stirred at 85° C. for 5h. Upon cooling to room temperature, the reaction was diluted with DCM (150 mL) and washed with 1N HCl (50 mL) and water. The organic phase was dried over $MgSO_4$, concentrated, and purified with silica gel column to afford 2'-chloro-2-ethyl-3,5-difluoro-4'-(1,1,1,3,3,3-hexafluoro-2-hydroxypropan-2-yl)-N-methoxy-N-methyl-[1,1'-biphenyl]-4-carboxamide (0.94 g, 78% yield) as a white solid.

To a solution of 2'-chloro-2-ethyl-3,5-difluoro-4'-(1,1,1,3,3,3-hexafluoro-2-hydroxypropan-2-yl)-N-methoxy-N-methyl-[1,1'-biphenyl]-4-carboxamide (0.9 g, 1 equiv) in anhydrous THF (20 mL) was added 1.0 M LAH solution in THF (1.9 mL, 1.1 equiv) at −78° C. The reaction was stirred at −78° C. for 1h and quenched by adding EtOAc (2 mL) before being warmed to room temperature. The mixture was poured into $NH_4Cl$ solution and extracted with DCM (2×50 mL). The organic phase was dried over $MgSO_4$, concentrated, and purified with silica gel column to afford 2'-chloro-2-ethyl-3,5-difluoro-4'-(1,1,1,3,3,3-hexafluoro-2-hydroxypropan-2-yl)-[1,1'-biphenyl]-4-carbaldehyde (0.71 g, 90% yield) as a white solid.

Amine Intermediate 2A (0.48 g, 1.5 equiv) and 2'-chloro-2-ethyl-3,5-difluoro-4'-(1,1,1,3,3,3-hexafluoro-2-hydroxypropan-2-yl)-[1,1'-biphenyl]-4-carbaldehyde (0.7 g, 1.0 equiv) were dissolved in 40 mL 1,2-DCE. To the mixture was added AcOH (0.2 mL). The resulting mixture was stirred at rt for 4h. Sodium triacetoxyborohydride (1.06 g, 3 equiv) was added portion-wise over 3h. The mixture was stirred at room temperature overnight. The mixture was quenched with MeOH (10 mL), and then poured the reaction mixture into saturated $NaHCO_3$ solution, extracted with DCM (2×60 mL). The organic phase was dried over $MgSO_4$, concentrated, and purified with silica gel column to afford the title compound (0.63 g, 65% yield) as a white solid. LC-MS (ESI) m/z $(M+H)^+$. 621.4.

Example 11: Synthesis of 2-(2-chloro-2'-ethyl-3',6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol

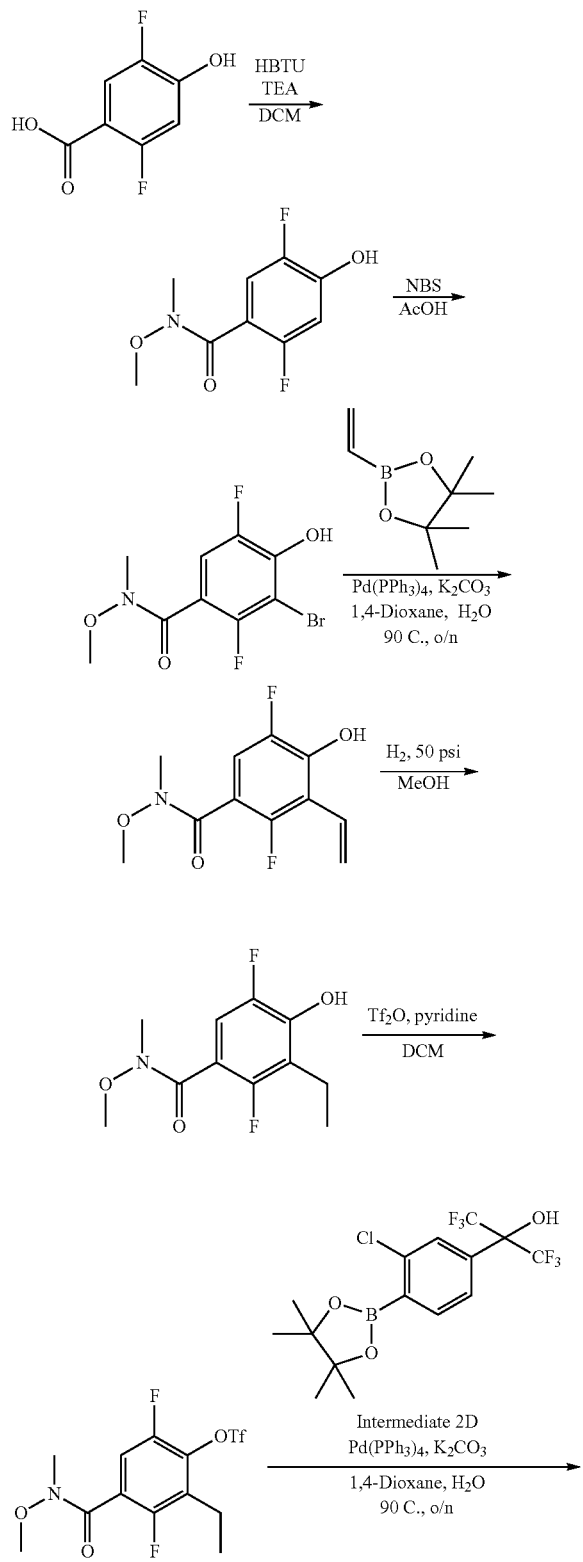

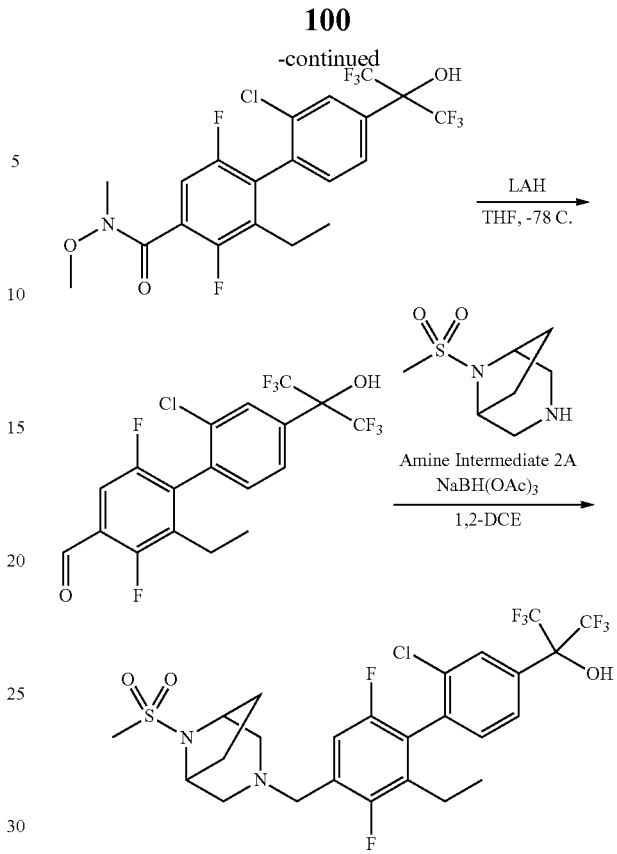

To a stirred solution of 2,5-difluoro-4-hydroxybenzoic acid (6.0 g, 1.0 equiv) in acetic acid (200 mL) was added $Br_2$ (5.5 g, 2.0 equiv) dropwise at 0° C. The reaction was warmed up to room temperature and then stirred at 60° C. for 4h. The reaction mixture was concentrated under vacuum to afford 3-bromo-2,5-difluoro-4-hydroxybenzoic acid (8.2 g, 95% yield) as a pale yellow solid, which was directly used in next step without purification.

To a mixture of 3-bromo-2,5-difluoro-4-hydroxybenzoic acid (8.1 g, 1.0 equiv), triethylamine (14 mL, 3.0 equiv) and N,O-dimethylhydroxylamine hydrochloride (4.8 g, 1.5 equiv) in DMA (120 mL) was added HBTU (13.5 g, 1.1 equiv). The mixture was stirred at room temperature for 4h. Additional HBTU (4.9 g, 0.4 equiv) was added. The reaction was diluted with EtOAc-Hexane (v/v 80/20, 300 mL) and washed with 1N HCl (2×150 mL). The organic phase was dried over $MgSO_4$, concentrated, and purified with column chromatography to afford 3-bromo-2,5-difluoro-4-hydroxy-N-methoxy-N-methylbenzamide (8.9 g, 94% yield) as a white solid.

To a solution of 3-bromo-2,5-difluoro-4-hydroxy-N-methoxy-N-methylbenzamide (5.1 g, 1 equiv) in 1,4-dioxane (100 mL) and water (10 mL) was added 4,4,5,5-tetramethyl-2-vinyl-1,3,2-dioxaborolane (4.3 g, 1.6 equiv), potassium carbonate (6.0 g, 2.5 equiv), and $Pd(PPh_3)_4$ (1.0 g, 0.05 equiv). The mixture was bubbled with $N_2$ for 10 min, and then stirred at 90° C. overnight (20h). Upon cooling to room temperature, 1N HCl (150 mL) was added and the mixture was extracted with DCM (3×200 mL). The organic phase was dried over $MgSO_4$, concentrated, and purified with column chromatography to afford 2,5-difluoro-4-hydroxy-N-methoxy-N-methyl-3-vinylbenzamide (1.3 g, 30% yield) as a white solid.

To a solution of 2,5-difluoro-4-hydroxy-N-methoxy-N-methyl-3-vinylbenzamide (2.5 g, 1.0 equiv) in MeOH (30 mL) was added Pd/C (10% wt., 500 mg). The mixture was hydrogenated under $H_2$ (50 psi) for 4h. The mixture was filtered through celite pad to remove the catalyst and concentrated. The crude mixture was purified by silica gel column to afford 3-ethyl-2,5-difluoro-4-hydroxy-N-methoxy-N-methylbenzamide (2.5 g, 100%) as an oil.

To a solution of 3-ethyl-2,5-difluoro-4-hydroxy-N-methoxy-N-methylbenzamide (2.5 g, 9.7 mmol, 1 equiv) and pyridine (2 ml, 2.5 equiv) in DCM (50 ml) was added trifluoromethanesulfonic anhydride (1.8 g, 1.5 equiv) dropwise at 0° C. The mixture was stirred at 0° C. for 30 min, and then washed with saturated $NaHCO_3$ solution, 1N HCl, and water. The organic phase was dried over $MgSO_4$, concentrated, and purified with column chromatography to afford 2-ethyl-3,6-difluoro-4-(methoxy(methyl)carbamoyl)phenyl trifluoromethanesulfonate (3.6 g, 95% yield) as a pale yellow oil.

To a solution of 2-ethyl-3,6-difluoro-4-(methoxy(methyl)carbamoyl)phenyl trifluoromethanesulfonate (1.9 g, 1.0 equiv) in 1,4-dioxane (50 mL) and water (5 mL) was added 2-(3-chloro-4-(4,4,5,5-tetramethyl-1,3,2-dioxaborolan-2-yl)phenyl)-1,1,1,3,3,3-hexafluoropropan-2-ol intermediate from Example 10 (2.6 g, 1.3 equiv), potassium carbonate (1.4 g, 2.0 equiv), and $Pd(PPh_3)_4$ (0.56 g, 0.49 mmol, 0.1 equiv). The mixture bubbled with $N_2$ for 10 min, and then stirred at 85° C. for 5h. Upon cooling to room temperature, the reaction was diluted with DCM (200 mL) and washed with 1N HCl (50 mL) and water. The organic phase was dried over $MgSO_4$, concentrated, and purified with column chromatography to afford 2'-chloro-2-ethyl-3,6-difluoro-4'-(1,1,1,3,3,3-hexafluoro-2-hydroxypropan-2-yl)-N-methoxy-N-methyl-[1,1'-biphenyl]-4-carboxamide (1.78 g, 72% yield) as a white solid.

To a solution of 2'-chloro-2-ethyl-3,6-difluoro-4'-(1,1,1,3,3,3-hexafluoro-2-hydroxypropan-2-yl)-N-methoxy-N-methyl-[1,1'-biphenyl]-4-carboxamide (1.75 g, 1 equiv) in anhydrous THF (30 mL) was added 1.0 M LAH solution in THF (3.7 mL, 1.1 equiv) at −78° C. The reaction was stirred at −78° C. for 1h and quenched by adding EtOAc (2 mL) before being warmed to room temperature. The mixture was poured into $NH_4Cl$ solution and extracted with DCM (2×50 mL). The organic phase was dried over $MgSO_4$, concentrated, and purified with column chromatography to afford 2-ethyl-3,6-difluoro-4'-(1,1,1,3,3,3-hexafluoro-2-hydroxypropan-2-yl)-[1,1'-biphenyl]-4-carbaldehyde (1.4 g, 93% yield) as a white solid.

Amine Intermediate 2A (0.58 g, 1.5 equiv) and 2-ethyl-3,6-difluoro-4'-(1,1,1,3,3,3-hexafluoro-2-hydroxypropan-2-yl)-[1,1'-biphenyl]-4-carbaldehyde (0.92 g, 1.0 equiv) were dissolved in 1,2-DCE (40 mL). To the mixture was added AcOH (0.3 mL, ~0.3 equiv). The resulting mixture was stirred at rt for 4h. Sodium triacetoxyborohydride (1.7 g, 4.0 equiv) was added portion-wise over 3h. The mixture was stirred at rt overnight. The mixture was quenched with MeOH (10 mL). The mixture was poured into saturated $NaHCO_3$ solution and extracted with DCM (3×60 mL). The organic phase was dried over $MgSO_4$, concentrated, and purified with column chromatography to afford the title compound (1.0 g, 80% yield) as a white solid. LC-MS (ESI) m/z $(M+H)^+$: 621.4.

Examples 12-78

The following compounds in Table 1 were synthesized using the procedures described in the preceding examples wherein an aldehyde intermediate (Aldehyde Int.) (1.0 equiv) and an amine intermediate (Amine Int.) (1.2 equiv) were combined to afford the title compounds.

TABLE 1

| Ex. No. | Structure | Chemical Name | Intermediates used | LC-MS (ESI) m/z $(M + H)^+$ |
|---|---|---|---|---|
| 12 | 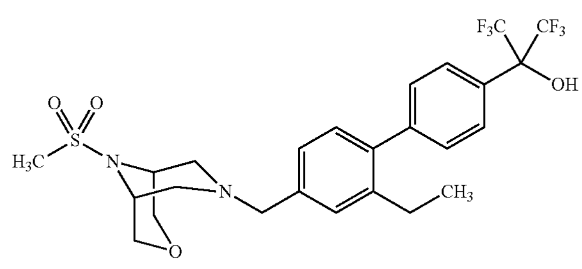 [SMILES: CCc1cc(CN2CC3COCC(C2)N3S(C)(=O)=O)ccc1-c1ccc(C(O)(C(F)(F)F)C(F)(F)F)cc1] | 2-(2'-ethyl-4'-((9-(methylsulfonyl)-3-oxa-7,9-diazabicyclo[3.3.1]nonan-7-yl)methyl)-[1,1'-biphenyl]-4-yl)-1,1,1,3,3,3-hexafluoropropan-2-ol | Aldehyde Int. 2 Amine Int. 8 | 567.4 |
| 13 | 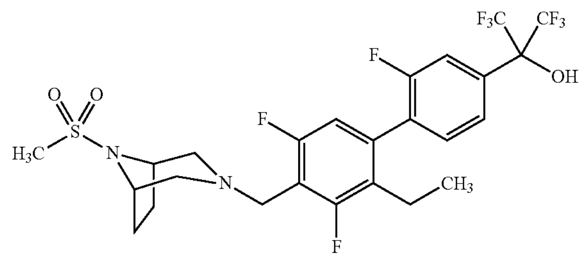 [SMILES: CCc1c(-c2ccc(C(O)(C(F)(F)F)C(F)(F)F)cc2F)cc(F)c(CN2CC3CCC(C2)N3S(C)(=O)=O)c1F] | 2-(2'-ethyl-2,3',5'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 11C Amine Int. 2A | 605.4 |

TABLE 1-continued

| Ex. No. | Structure | Chemical Name | Intermediates used | LC-MS (ESI) m/z (M + H)+ |
|---|---|---|---|---|
| 14 | 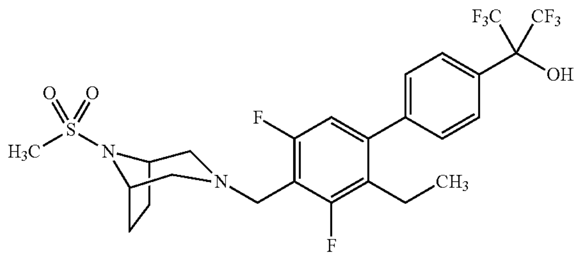 [SMILES: CCc1c(-c2ccc(C(O)(C(F)(F)F)C(F)(F)F)cc2)cc(F)c(CN2CC3CCC(C2)N3S(C)(=O)=O)c1F] | 2-(2'-ethyl-2,3',5'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 11C Amine Int. 2A | 587.1 |
| 15 | 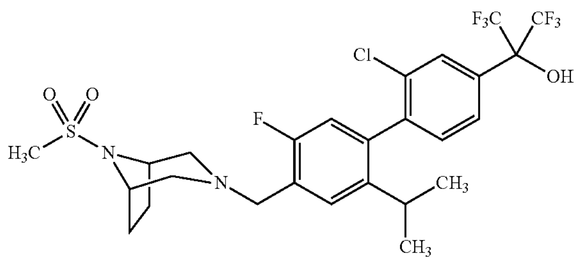 [SMILES: CC(C)c1cc(CN2CC3CCC(C2)N3S(C)(=O)=O)c(F)cc1-c1ccc(C(O)(C(F)(F)F)C(F)(F)F)cc1Cl] | 2-(2-chloro-5'-fluoro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 12D Amine Int. 2A | 617.5 |
| 16 | 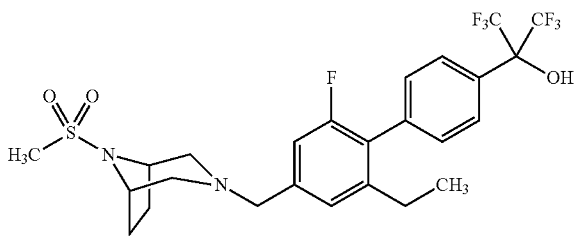 [SMILES: CCc1cc(CN2CC3CCC(C2)N3S(C)(=O)=O)cc(F)c1-c1ccc(C(O)(C(F)(F)F)C(F)(F)F)cc1] | 2-(2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 13 Amine Int. 2A | 569.3 |
| 17 | 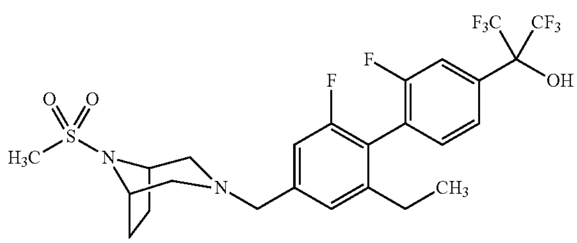 [SMILES: CCc1cc(CN2CC3CCC(C2)N3S(C)(=O)=O)cc(F)c1-c1ccc(C(O)(C(F)(F)F)C(F)(F)F)cc1F] | 2-(2'-ethyl-2,6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 13C Amine Int. 2A | 587.3 |
| 18 | 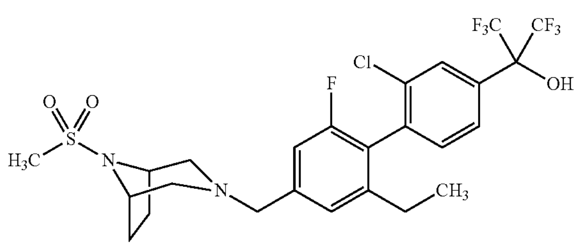 [SMILES: CCc1cc(CN2CC3CCC(C2)N3S(C)(=O)=O)cc(F)c1-c1ccc(C(O)(C(F)(F)F)C(F)(F)F)cc1Cl] | 2-(2-chloro-2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 13D Amine Int. 2A | 603.4 |
| 19 | 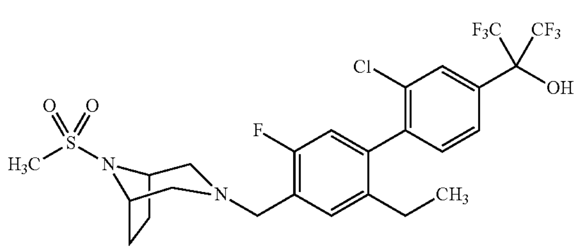 [SMILES: CCc1cc(CN2CC3CCC(C2)N3S(C)(=O)=O)c(F)cc1-c1ccc(C(O)(C(F)(F)F)C(F)(F)F)cc1Cl] | 2-(2-chloro-2'-ethyl-5'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 14 Amine Int. 2A | 603.5 |

TABLE 1-continued

| Ex. No. | Structure | Chemical Name | Intermediates used | LC-MS (ESI) m/z (M + H)+ |
|---|---|---|---|---|
| 20 | 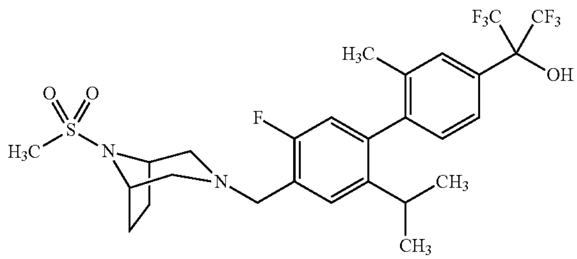 [SMILES: Cc1cc(C(O)(C(F)(F)F)C(F)(F)F)ccc1-c1cc(F)c(CN2CC3CCC(C2)N3S(C)(=O)=O)cc1C(C)C] | 1,1,1,3,3,3-hexafluoro-2-(5'-fluoro-2'-isopropyl-2-methyl-4'-((8-(methylsulfonyl)-3,8-diazabicyclo[3.2.1]octan-3-yl)methyl)-[1,1'-biphenyl]-4-yl)propan-2-ol | Aldehyde Int. 12A Amine Int. 2A | 597.5 |
| 21 | 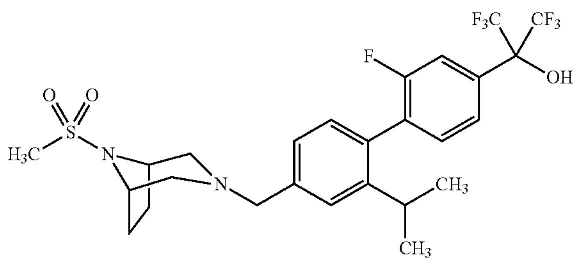 [SMILES: CC(C)c1cc(CN2CC3CCC(C2)N3S(C)(=O)=O)ccc1-c1ccc(C(O)(C(F)(F)F)C(F)(F)F)cc1F] | 2-(2-chloro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 3C Amine Int. 2A | 583.4 |
| 22 | 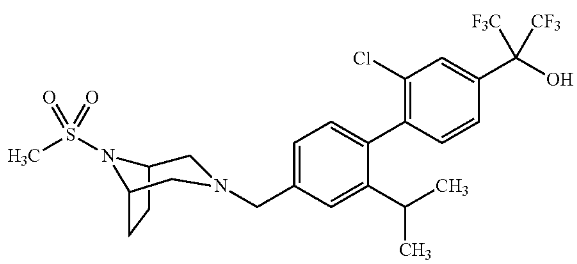 [SMILES: CC(C)c1cc(CN2CC3CCC(C2)N3S(C)(=O)=O)ccc1-c1ccc(C(O)(C(F)(F)F)C(F)(F)F)cc1Cl] | 2-(2-chloro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 3D Amine Int. 2A | 599.4 |
| 23 | 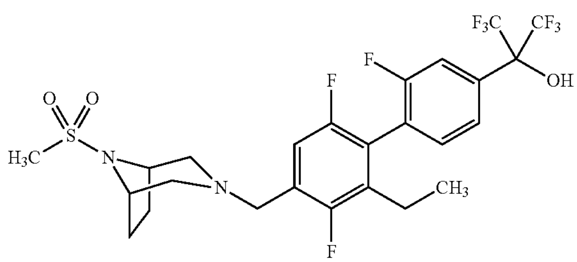 [SMILES: CCc1c(F)c(CN2CC3CCC(C2)N3S(C)(=O)=O)cc(F)c1-c1ccc(C(O)(C(F)(F)F)C(F)(F)F)cc1F] | 2-(2'-ethyl-2,3',6'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 7C Amine Int. 2A | 605.6 |
| 24 | 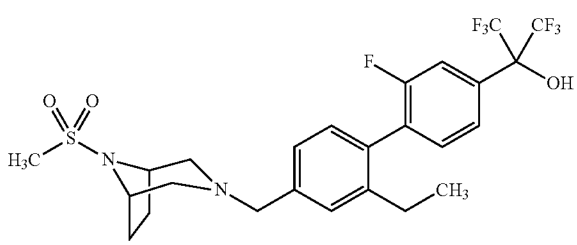 [SMILES: CCc1cc(CN2CC3CCC(C2)N3S(C)(=O)=O)ccc1-c1ccc(C(O)(C(F)(F)F)C(F)(F)F)cc1F] | 2-(2'-ethyl-2-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2C Amine Int. 2A | 569.3 |
| 25 | 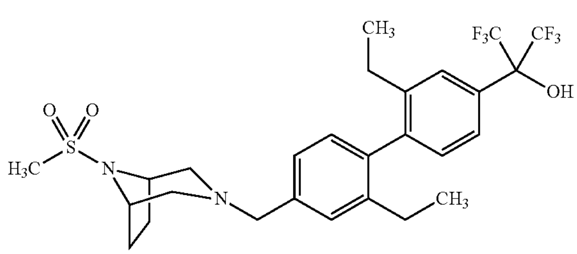 [SMILES: CCc1cc(CN2CC3CCC(C2)N3S(C)(=O)=O)ccc1-c1ccc(C(O)(C(F)(F)F)C(F)(F)F)cc1CC] | 2-(2,2'-diethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2B Amine Int. 2A | 579.4 |

TABLE 1-continued

| Ex. No. | Structure | Chemical Name | Intermediates used | LC-MS (ESI) m/z (M + H)+ |
|---|---|---|---|---|
| 26 | 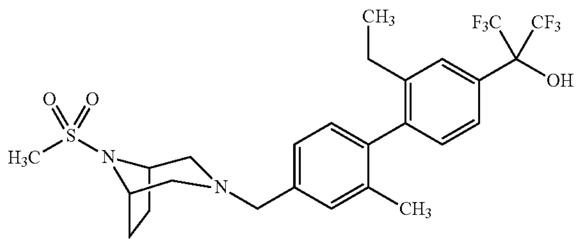 [SMILES: CCc1cc(C(O)(C(F)(F)F)C(F)(F)F)ccc1-c1ccc(CN2CC3CCC(C2)N3S(C)(=O)=O)cc1C] | 2-(2-ethyl-2'-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 11 Amine Int. 2A | 565.6 |
| 27 | 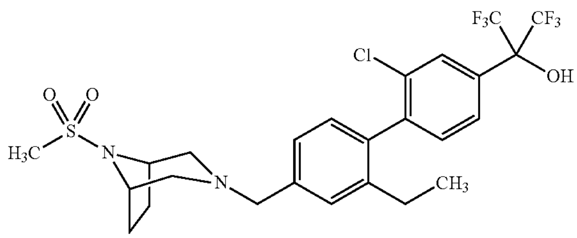 [SMILES: CCc1cc(CN2CC3CCC(C2)N3S(C)(=O)=O)ccc1-c1ccc(C(O)(C(F)(F)F)C(F)(F)F)cc1Cl] | 2-(2-chloro-2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2D Amine Int. 2A | 585.4 |
| 28 | 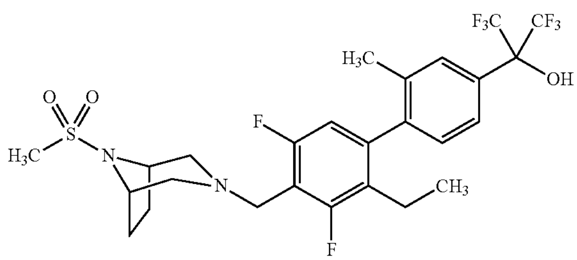 [SMILES: CCc1c(-c2ccc(C(O)(C(F)(F)F)C(F)(F)F)cc2C)cc(F)c(CN2CC3CCC(C2)N3S(C)(=O)=O)c1F] | 2-(2'-ethyl-3',5'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 10A Amine Int. 2A | 601.4 |
| 29 | 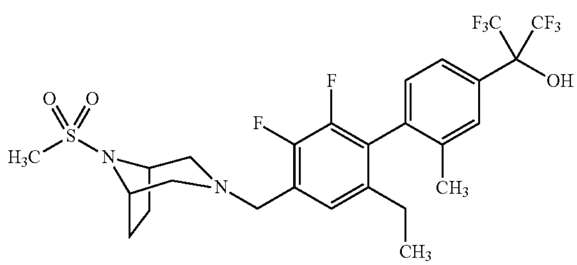 [SMILES: CCc1cc(CN2CC3CCC(C2)N3S(C)(=O)=O)c(F)c(F)c1-c1ccc(C(O)(C(F)(F)F)C(F)(F)F)cc1C] | 2-(6'-ethyl-2',3'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 8 Amine Int. 2A | 601.2 |
| 30 | 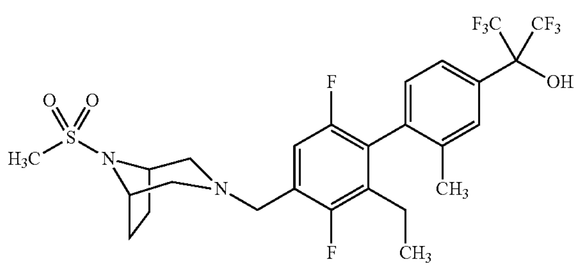 [SMILES: CCc1c(F)c(CN2CC3CCC(C2)N3S(C)(=O)=O)cc(F)c1-c1ccc(C(O)(C(F)(F)F)C(F)(F)F)cc1C] | 2-(2'-ethyl-3',6'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 7A Amine Int. 2A | 601.3 |
| 31 | 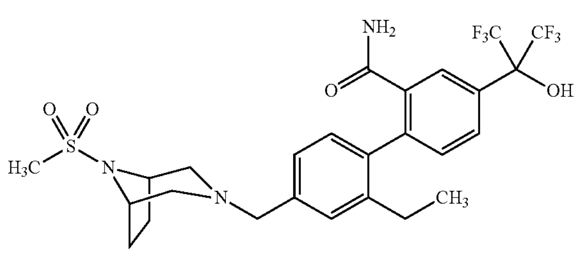 [SMILES: CCc1cc(CN2CC3CCC(C2)N3S(C)(=O)=O)ccc1-c1ccc(C(O)(C(F)(F)F)C(F)(F)F)cc1C(N)=O] | 2'-ethyl-4-(1,1,1,3,3,3-hexafluoro-2-hydroxypropan-2-yl)-4'-((8-(methylsulfonyl)-3,8-diazabicyclo[3.2.1]octan-3-yl)methyl)-[1,1'-biphenyl]-2-carboxamide | Aldehyde Int. 6A Amine Int. 2A | 594.6 |

TABLE 1-continued

| Ex. No. | Structure | Chemical Name | Intermediates used | LC-MS (ESI) m/z (M + H)+ |
|---|---|---|---|---|
| 32 | 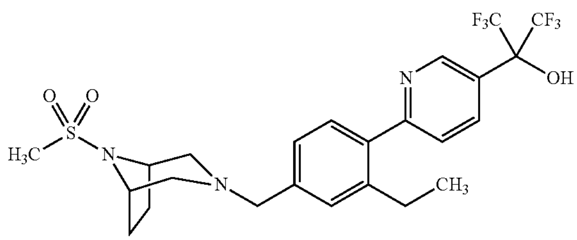 [SMILES: CCc1cc(CN2CC3CCC(C2)N3S(C)(=O)=O)ccc1-c1ccc(C(O)(C(F)(F)F)C(F)(F)F)cn1] | 2-(6-(2-ethyl-4-((8-(methylsulfonyl)-3,8-diazabicyclo[3.2.1]octan-3-yl)methyl)phenyl)pyridin-3-yl)-1,1,1,3,3,3-hexafluoropropan-2-ol | Aldehyde Int. 5 Amine Int. 2A | 552.3 |
| 33 | 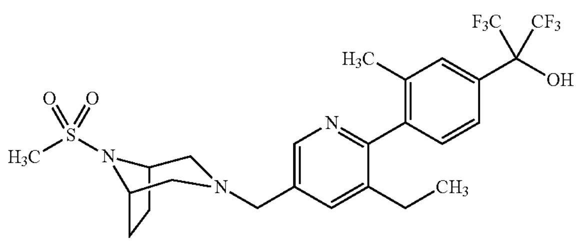 [SMILES: CCc1cc(CN2CC3CCC(C2)N3S(C)(=O)=O)cnc1-c1ccc(C(O)(C(F)(F)F)C(F)(F)F)cc1C] | 2-(4-(3-ethyl-5-((8-(methylsulfonyl)-3,8-diazabicyclo[3.2.1]octan-3-yl)methyl)pyridin-2-yl)-3-methylphenyl)-1,1,1,3,3,3-hexafluoropropan-2-ol | Aldehyde Int. 4 Amine Int. 2A | 566.5 |
| 34 | 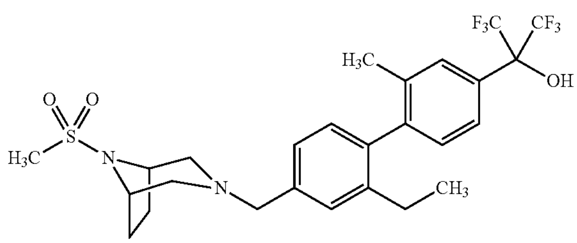 [SMILES: CCc1cc(CN2CC3CCC(C2)N3S(C)(=O)=O)ccc1-c1ccc(C(O)(C(F)(F)F)C(F)(F)F)cc1C] | 2-(2'-ethyl-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2A Amine Int. 2A | 565.4 |
| 35 | 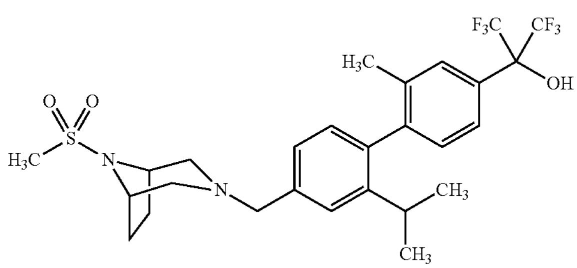 [SMILES: Cc1cc(C(O)(C(F)(F)F)C(F)(F)F)ccc1-c1ccc(CN2CC3CCC(C2)N3S(C)(=O)=O)cc1C(C)C] | 1,1,1,3,3,3-hexafluoro-2-(2'-isopropyl-2-methyl-4'-((8-(methylsulfonyl)-3,8-diazabicyclo[3.2.1]octan-3-yl)methyl)-[1,1'-biphenyl]-4-yl)propan-2-ol | Aldehyde Int. 3A Amine Int. 2A | 579.6 |
| 36 | 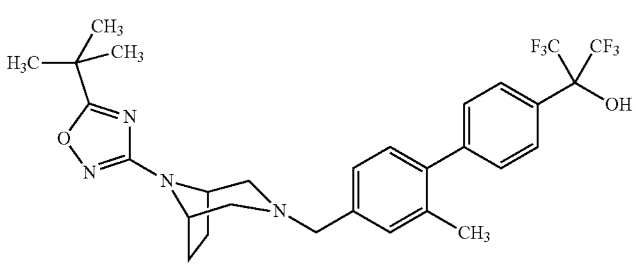 [SMILES: Cc1cc(CN2CC3CCC(C2)N3c2noc(C(C)(C)C)n2)ccc1-c1ccc(C(O)(C(F)(F)F)C(F)(F)F)cc1] | 2-(4'-((8-(5-(tert-butyl)-1,2,4-oxadiazol-3-yl)-3,8-diazabicyclo[3.2.1]octan-3-yl)methyl)-2'-methyl-[1,1'-biphenyl]-4-yl)-1,1,1,3,3,3-hexafluoropropan-2-ol | Aldehyde Int. 1A Amine Int. 4 | 583.2 |
| 37 | 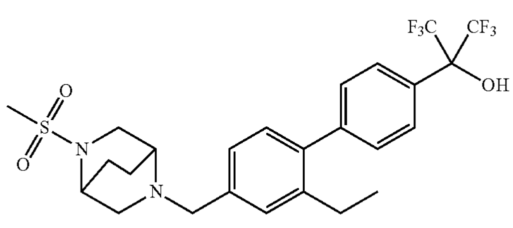 [SMILES: CCc1cc(CN2CC3CCC2CN3S(C)(=O)=O)ccc1-c1ccc(C(O)(C(F)(F)F)C(F)(F)F)cc1] | 2-(2'-ethyl-4'-((5-(methylsulfonyl)-2,5-diazabicyclo[2.2.2]octan-2-yl)methyl)-[1,1'-biphenyl]-4-yl)-1,1,1,3,3,3-hexafluoropropan-2-ol | Aldehyde Int. 2 Amine Int. 2A | 551.3 |

TABLE 1-continued

| Ex. No. | Structure | Chemical Name | Intermediates used | LC-MS (ESI) m/z (M + H)+ |
|---|---|---|---|---|
| 38 | 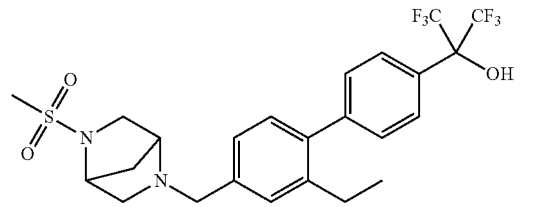 [SMILES: CCc1cc(CN2CC3CC2CN3S(C)(=O)=O)ccc1-c1ccc(C(O)(C(F)(F)F)C(F)(F)F)cc1] | 2-(2'-ethyl-4'-((5-(methylsulfonyl)-2,5-diazabicyclo[2.2.1]heptan-2-yl)methyl)-[1,1'-biphenyl]-4-yl)-1,1,1,3,3,3-hexafluoropropan-2-ol | Aldehyde Int. 2 Amine Int. 5 | 537.5 |
| 39 | 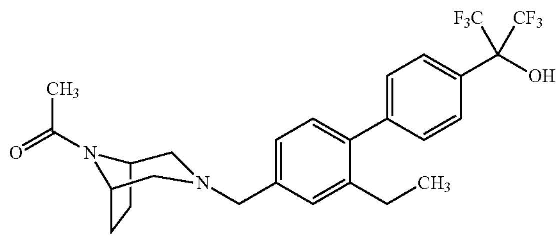 [SMILES: CCc1cc(CN2CC3CCC(C2)N3C(C)=O)ccc1-c1ccc(C(O)(C(F)(F)F)C(F)(F)F)cc1] | 1-(3-((2-ethyl-4'-(1,1,1,3,3,3-hexafluoro-2-hydroxypropan-2-yl)-[1,1'-biphenyl]-4-yl)methyl)-3,8-diazabicyclo[3.2.1]octan-8-yl)ethan-1-one | Aldehyde Int. 2 Amine Int. 3A | 515.5 |
| 40 | 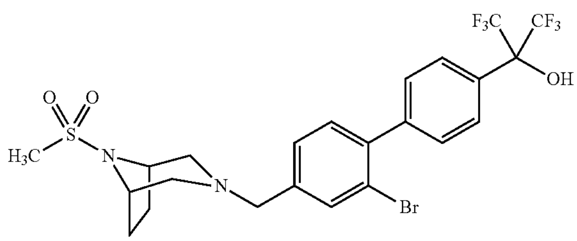 [SMILES: CS(=O)(=O)N1C2CCC1CN(Cc1ccc(-c3ccc(C(O)(C(F)(F)F)C(F)(F)F)cc3)c(Br)c1)C2] | 2-(2'-bromo-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 1E Amine Int. 2A | 610, 603 |
| 41 | 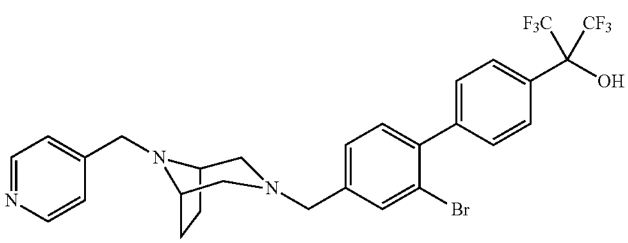 | 2-(2'-bromo-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 1E Amine Int. 1A | 614, 616 |
| 42 | 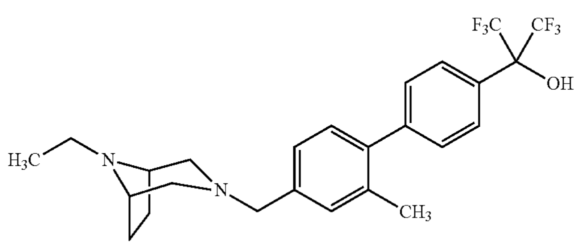 [SMILES: CCN1C2CCC1CN(Cc1ccc(-c3ccc(C(O)(C(F)(F)F)C(F)(F)F)cc3)c(C)c1)C2] | 2-(4'-((8-ethyl-3,8-diazabicyclo[3.2.1]octan-3-yl)methyl)-2'-methyl-[1,1'-biphenyl]-4-yl)-1,1,1,3,3,3-hexafluoropropan-2-ol | Aldehyde Int. 1A Amine Int. 1H | 487.3 |
| 43 | 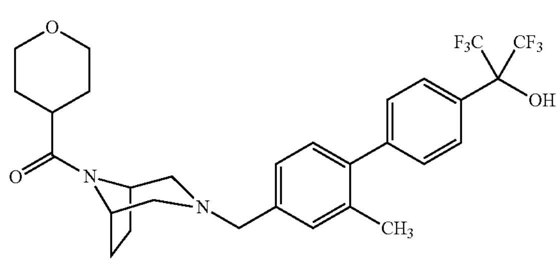 [SMILES: Cc1cc(CN2CC3CCC(C2)N3C(=O)C2CCOCC2)ccc1-c1ccc(C(O)(C(F)(F)F)C(F)(F)F)cc1] | (3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(tetrahydro-2H-pyran-4-yl)methanone | Aldehyde Int. 1A Amine Int. 3D | 571.5 |

TABLE 1-continued

| Ex. No. | Structure | Chemical Name | Intermediates used | LC-MS (ESI) m/z (M + H)+ |
|---|---|---|---|---|
| 44 | 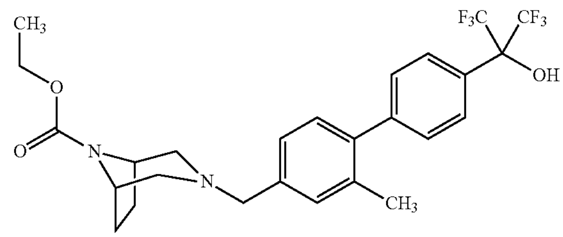 [SMILES: CCOC(=O)N1C2CCC1CN(Cc1ccc(-c3ccc(C(O)(C(F)(F)F)C(F)(F)F)cc3)c(C)c1)C2] | ethyl 3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octane-8-carboxylate | Aldehyde Int. 1A Amine Int. 3E | 531.3 |
| 45 | 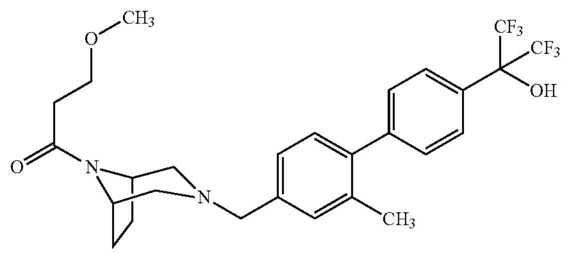 [SMILES: COCCC(=O)N1C2CCC1CN(Cc1ccc(-c3ccc(C(O)(C(F)(F)F)C(F)(F)F)cc3)c(C)c1)C2] | 1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-3-methoxypropan-1-one | Aldehyde Int. 1A Amine Int. 3C | 545.3 |
| 46 | 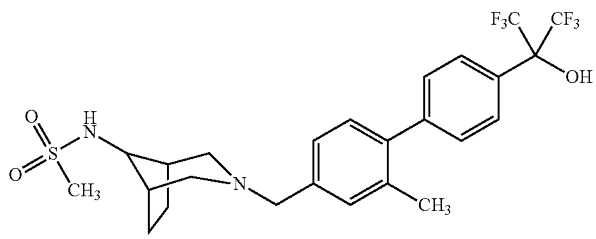 [SMILES: Cc1cc(CN2CC3CCC(C2)C3NS(C)(=O)=O)ccc1-c1ccc(C(O)(C(F)(F)F)C(F)(F)F)cc1] | N-(3-((4'-(1,1,1,3,3,3-hexafluoro-2-hydroxypropan-2-yl)-2-methyl-[1,1'-biphenyl]-4-yl)methyl)-3-azabicyclo[3.2.1]octan-8-yl)methanesulfonamide | Aldehyde Int. 1A Amine Int. 7 | 551.5 |
| 47 | 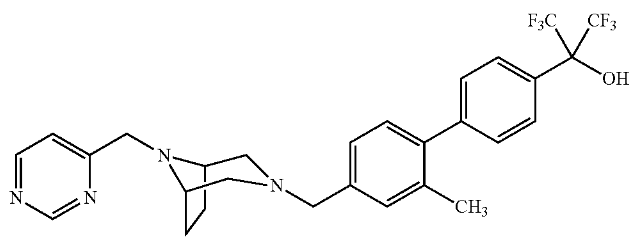 [SMILES: Cc1cc(CN2CC3CCC(C2)N3Cc2ccncn2)ccc1-c1ccc(C(O)(C(F)(F)F)C(F)(F)F)cc1] | 1,1,1,3,3,3-hexafluoro-2-(2'-methyl-4'-((8-(pyrimidin-4-ylmethyl)-3,8-diazabicyclo[3.2.1]octan-3-yl)methyl)-[1,1'-biphenyl]-4-yl)propan-2-ol | Aldehyde Int. 1A Amine Int. 3G | 551.6 |
| 48 | 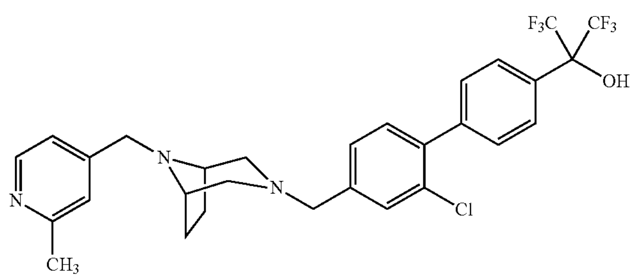 [SMILES: Cc1cc(CN2C3CCC2CN(Cc2ccc(-c4ccc(C(O)(C(F)(F)F)C(F)(F)F)cc4)c(Cl)c2)C3)ccn1] | 2-(2'-chloro-4'-((8-((2-methylpyridin-4-yl)methyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 1D Amine Int. 1D | 584.3 |
| 49 | 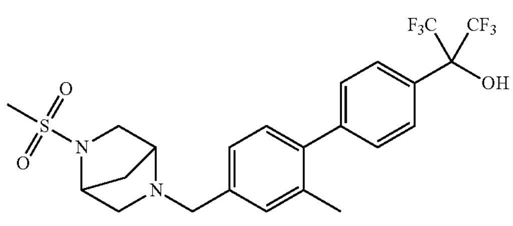 [SMILES: Cc1cc(CN2CC3CC2CN3S(C)(=O)=O)ccc1-c1ccc(C(O)(C(F)(F)F)C(F)(F)F)cc1] | 1,1,1,3,3,3-hexafluoro-2-(2'-methyl-4'-((5-(methylsulfonyl)-2,5-diazabicyclo[2.2.1]heptan-2-yl)methyl)-[1,1'-biphenyl]-4-yl)propan-2-ol | Aldehyde Int. 1A Amine Int. 5 | 523.4 |

TABLE 1-continued

| Ex. No. | Structure | Chemical Name | Intermediates used | LC-MS (ESI) m/z (M + H)+ |
|---|---|---|---|---|
| 50 | 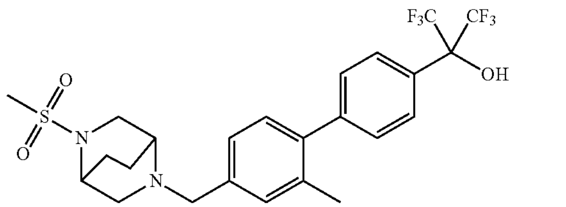 [SMILES: Cc1cc(CN2CC3CCC2CN3S(C)(=O)=O)ccc1-c1ccc(C(O)(C(F)(F)F)C(F)(F)F)cc1] | 1,1,1,3,3,3-hexafluoro-2-(2'-methyl-4'-((5-(methylsulfonyl)-2,5-diazabicyclo[2.2.2]octan-2-yl)methyl)-[1,1'-biphenyl]-4-yl)propan-2-ol | Aldehyde Int. 1A Amine Int. 5 | 537.3 |
| 51 | 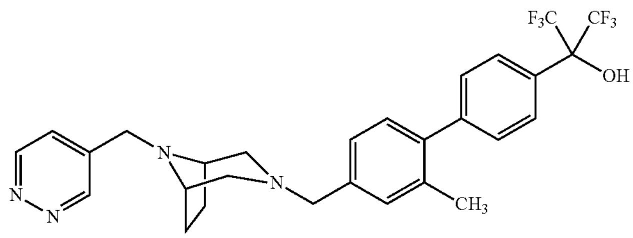 [SMILES: Cc1cc(CN2CC3CCC(C2)N3Cc2ccnnc2)ccc1-c1ccc(C(O)(C(F)(F)F)C(F)(F)F)cc1] | 1,1,1,3,3,3-hexafluoro-2-(2'-methyl-4'-((8-(pyridazin-4-ylmethyl)-3,8-diazabicyclo[3.2.1]octan-3-yl)methyl)-[1,1'-biphenyl]-4-yl)propan-2-ol | Aldehyde Int. 1A Amine Int. 1F | 551.6 |
| 52 | 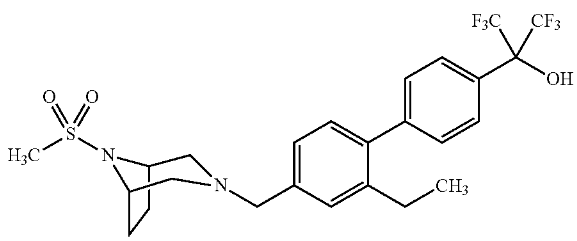 | 2-(2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2 Amine Int. 2A | 551.4 |
| 53 | 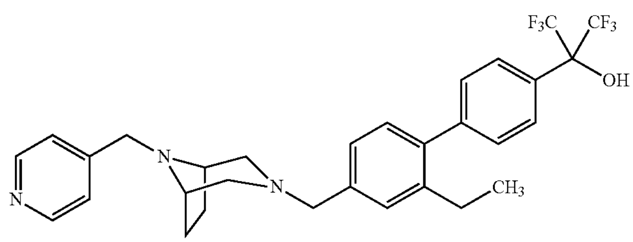 [SMILES: CCc1cc(CN2CC3CCC(C2)N3Cc2ccncc2)ccc1-c1ccc(C(O)(C(F)(F)F)C(F)(F)F)cc1] | 2-(2'-ethyl-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 2 Amine Int. 1A | 564.5 |
| 54 | 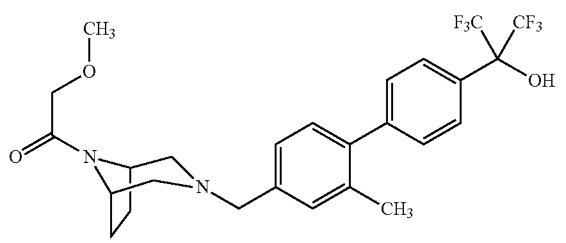 [SMILES: COCC(=O)N1C2CCC1CN(Cc1ccc(-c3ccc(C(O)(C(F)(F)F)C(F)(F)F)cc3)c(C)c1)C2] | 1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-2-methoxyethan-1-one | Aldehyde Int. 1A Amine Int. 3B | 531.3 |
| 55 | 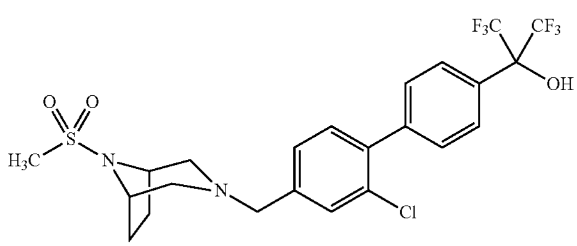 | 2-(2'-chloro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 1D Amine Int. 2A | 557.3 |

TABLE 1-continued

| Ex. No. | Structure | Chemical Name | Intermediates used | LC-MS (ESI) m/z (M + H)+ |
|---|---|---|---|---|
| 56 | 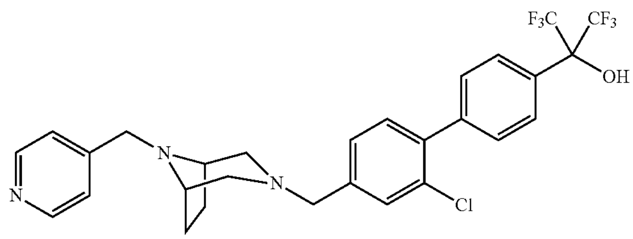 | 2-(2'-chloro-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol | Aldehyde Int. 1D Amine Int. 1A | 570.3 |
| 57 | 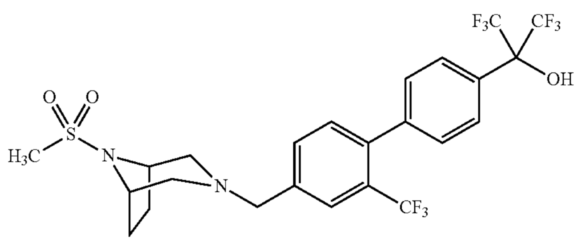 | 1,1,1,3,3,3-hexafluoro-2-(4'-((8-(methylsulfonyl)-3,8-diazabicyclo[3.2.1]octan-3-yl)methyl)-2'-(trifluoromethyl)-[1,1'-biphenyl]-4-yl)propan-2-ol | Aldehyde Int. 1B Amine Int. 2A | 591 |
| 58 | 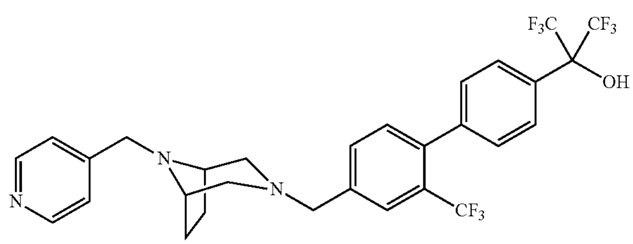 [SMILES: OC(c1ccc(-c2ccc(CN3CC4CCC(C3)N4Cc3ccncc3)cc2Cl)cc1)(C(F)(F)F)C(F)(F)F] | 1,1,1,3,3,3-hexafluoro-2-(4'-((8-(pyridin-4-ylmethyl)-3,8-diazabicyclo[3.2.1]octan-3-yl)methyl)-2'-(trifluoromethyl)-[1,1'-biphenyl]-4-yl)propan-2-ol | Aldehyde Int. 1B Amine Int. 1A | 604.4 |
| 59 | 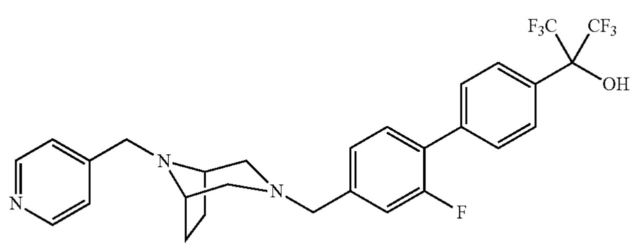 [SMILES: OC(c1ccc(-c2ccc(CN3CC4CCC(C3)N4Cc3ccncc3)cc2F)cc1)(C(F)(F)F)C(F)(F)F] | 1,1,1,3,3,3-hexafluoro-2-(2'-fluoro-4'-((8-(pyridin-4-ylmethyl)-3,8-diazabicyclo[3.2.1]octan-3-yl)methyl)-[1,1'-biphenyl]-4-yl)propan-2-ol | Aldehyde Int. 1C Amine Int. 1A | 554.2 |
| 60 | 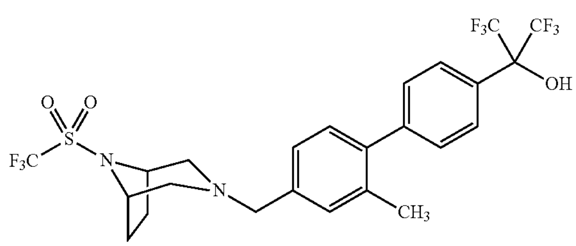 [SMILES: Cc1cc(CN2CC3CCC(C2)N3S(=O)(=O)C(F)(F)F)ccc1-c1ccc(C(O)(C(F)(F)F)C(F)(F)F)cc1] | 1,1,1,3,3,3-hexafluoro-2-(2'-methyl-4'-((8-((trifluoromethyl)sulfonyl)-3,8-diazabicyclo[3.2.1]octan-3-yl)methyl)-[1,1'-biphenyl]-4-yl)propan-2-ol | Aldehyde Int. 1A Amine Int. 2E | 591.4 |
| 61 | 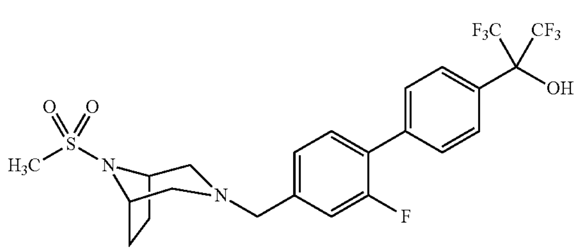 | 1,1,1,3,3,3-hexafluoro-2-(2'-fluoro-4'-((8-(methylsulfonyl)-3,8-diazabicyclo[3.2.1]octan-3-yl)methyl)-[1,1'-biphenyl]-4-yl)propan-2-ol | Aldehyde Int. 1C Amine Int. 2A | 541.3 |

TABLE 1-continued

| Ex. No. | Structure | Chemical Name | Intermediates used | LC-MS (ESI) m/z (M + H)+ |
|---|---|---|---|---|
| 62 | 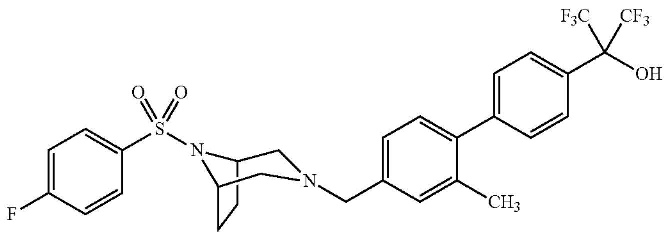 [SMILES: Cc1cc(CN2CC3CCC(C2)N3S(=O)(=O)c2ccc(F)cc2)ccc1-c1ccc(C(O)(C(F)(F)F)C(F)(F)F)cc1] | 1,1,1,3,3,3-hexafluoro-2-(4'-((8-((4-fluorophenyl)sulfonyl)-3,8-diazabicyclo[3.2.1]octan-3-yl)methyl)-2'-methyl-[1,1'-biphenyl]-4-yl)propan-2-ol | Aldehyde Int. 1A Amine Int. 2G | 617.5 |
| 63 | 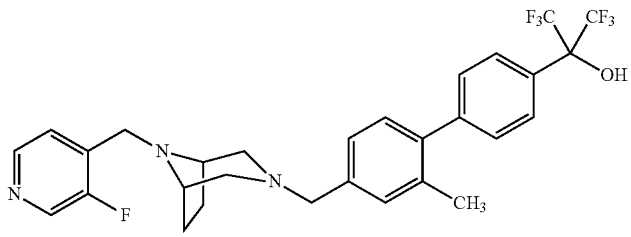 | 1,1,1,3,3,3-hexafluoro-2-(4'-((8-((3-fluoropyridin-4-yl)methyl)-3,8-diazabicyclo[3.2.1]octan-3-yl)methyl)-2'-methyl-[1,1'-biphenyl]-4-yl)propan-2-ol | Aldehyde Int. 1A Amine Int. 1E | 568.3 |
| 64 | 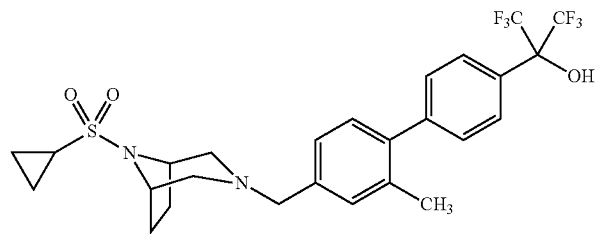 [SMILES: Cc1cc(CN2CC3CCC(C2)N3S(=O)(=O)C2CC2)ccc1-c1ccc(C(O)(C(F)(F)F)C(F)(F)F)cc1] | 2-(4'-((8-(cyclopropylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol | Aldehyde Int. 1A Amine Int. 2D | 563.4 |
| 65 | 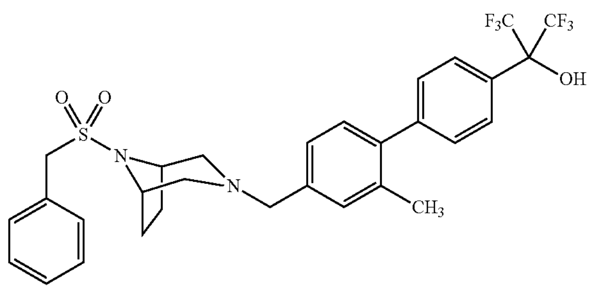 [SMILES: Cc1cc(CN2CC3CCC(C2)N3S(=O)(=O)Cc2ccccc2)ccc1-c1ccc(C(O)(C(F)(F)F)C(F)(F)F)cc1] | 2-(4'-((8-(benzylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol | Aldehyde Int. 1A Amine Int. 2H | 613.4 |
| 66 | 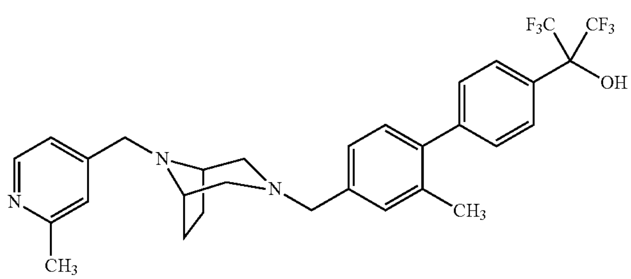 | 1,1,1,3,3,3-hexafluoro-2-(2'-methyl-4'-((8-((2-methylpyridin-4-yl)methyl)-3,8-diazabicyclo[3.2.1]octan-3-yl)methyl)-[1,1'-biphenyl]-4-yl)propan-2-ol | Aldehyde Int. 1A Amine Int. 1D | 564.6 |
| 67 | 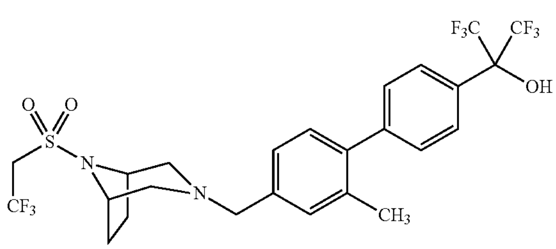 | 1,1,1,3,3,3-hexafluoro-2-(2'-methyl-4'-((8-((2,2,2-trifluoroethyl)sulfonyl)-3,8-diazabicyclo[3.2.1]octan-3-yl)methyl)-[1,1'-biphenyl]-4-yl)propan-2-ol | Aldehyde Int. 1A Amine Int. 2F | 605.4 |

TABLE 1-continued

| Ex. No. | Structure | Chemical Name | Intermediates used | LC-MS (ESI) m/z (M + H)+ |
|---|---|---|---|---|
| 68 | 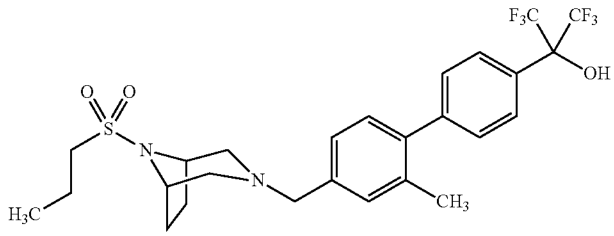 [SMILES: CCCS(=O)(=O)N1C2CCC1CN(Cc1ccc(-c3ccc(C(O)(C(F)(F)F)C(F)(F)F)cc3)c(C)c1)C2] | 1,1,1,3,3,3-hexafluoro-2-(2'-methyl-4'-((8-(propylsulfonyl)-3,8-diazabicyclo[3.2.1]octan-3-yl)methyl)-[1,1'-biphenyl]-4-yl)propan-2-ol | Aldehyde Int. 1A Amine Int. 2C | 565.4 |
| 69 | 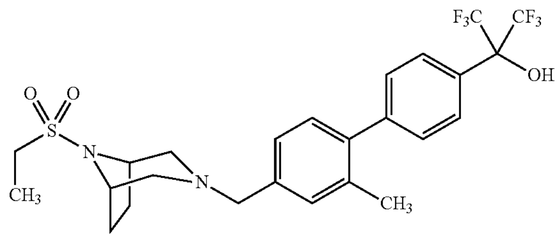 [SMILES: CCS(=O)(=O)N1C2CCC1CN(Cc1ccc(-c3ccc(C(O)(C(F)(F)F)C(F)(F)F)cc3)c(C)c1)C2] | 2-(4'-((8-(ethylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol | Aldehyde Int. 1A Amine Int. 2B | 551.5 |
| 70 | 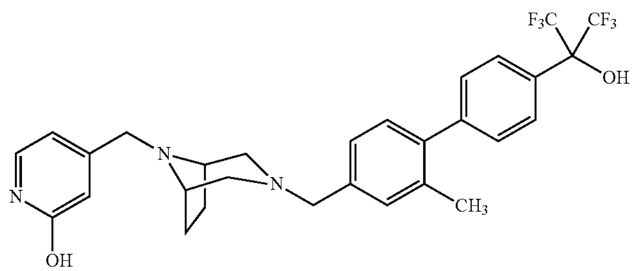 [SMILES: Cc1cc(CN2CC3CCC(C2)N3Cc2ccnc(O)c2)ccc1-c1ccc(C(O)(C(F)(F)F)C(F)(F)F)cc1] | 4-((3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)methyl)pyridin-2-ol | Aldehyde Int. 1A Amine Int. 1C | 566.6 |
| 71 | 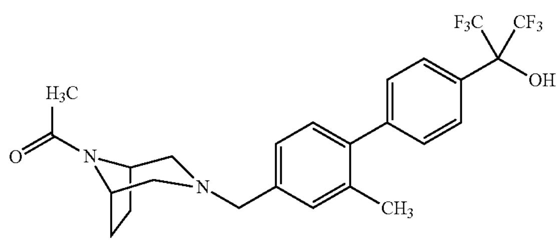 [SMILES: CC(=O)N1C2CCC1CN(Cc1ccc(-c3ccc(C(O)(C(F)(F)F)C(F)(F)F)cc3)c(C)c1)C2] | 1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one | Aldehyde Int. 1A Amine Int. 3A | 501.2 |
| 72 | 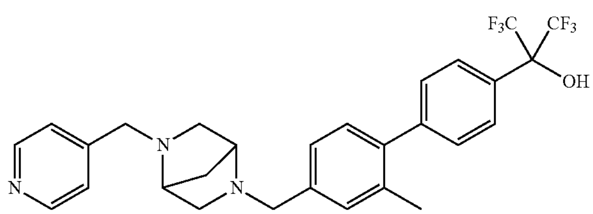 [SMILES: Cc1cc(CN2CC3CC2CN3Cc2ccncc2)ccc1-c1ccc(C(O)(C(F)(F)F)C(F)(F)F)cc1] | 1,1,1,3,3,3-hexafluoro-2-(2'-methyl-4'-((5-(pyridin-4-ylmethyl)-2,5-diazabicyclo[2.2.1]heptan-2-yl)methyl)-[1,1'-biphenyl]-4-yl)propan-2-ol | Aldehyde Int. 1A Amine Int. 9 | 536.6 |
| 73 | 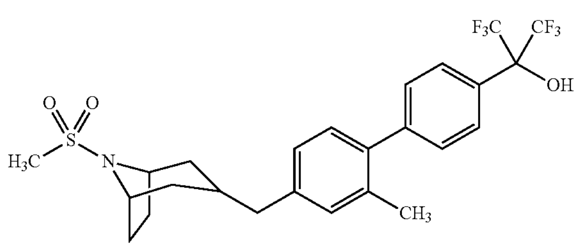 | 1,1,1,3,3,3-hexafluoro-2-(2'-methyl-4'-((8-(methylsulfonyl)-3,8-diazabicyclo[3.2.1]octan-3-yl)methyl)-[1,1'-biphenyl]-4-yl)propan-2-ol | Aldehyde Int. 1A Amine Int. 2A | 537.4 |

TABLE 1-continued

| Ex. No. | Structure | Chemical Name | Intermediates used | LC-MS (ESI) m/z (M + H)+ |
|---|---|---|---|---|
| 74 | 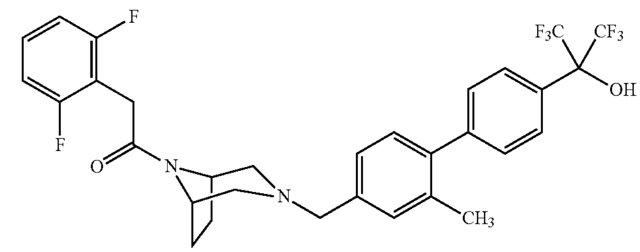 [SMILES: Cc1cc(CN2CC3CCC(C2)N3C(=O)Cc2c(F)cccc2F)ccc1-c1ccc(C(O)(C(F)(F)F)C(F)(F)F)cc1] | 2-(2,6-difluorophenyl)-1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one | Aldehyde Int. 1A Amine Int. 3G | 613.4 |
| 75 | 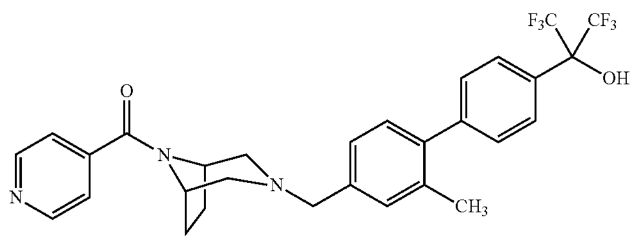 [SMILES: Cc1cc(CN2CC3CCC(C2)N3C(=O)c2ccncc2)ccc1-c1ccc(C(O)(C(F)(F)F)C(F)(F)F)cc1] | (3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(pyridin-4-yl)methanone | Aldehyde Int. 1A Amine Int. 3F | 564.5 |
| 76 | 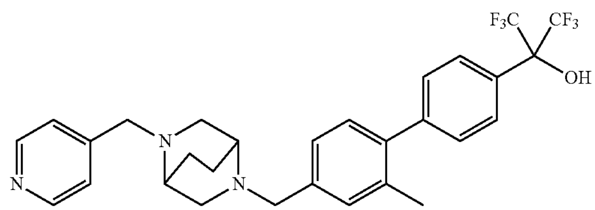 [SMILES: Cc1cc(CN2CC3CCC2CN3Cc2ccncc2)ccc1-c1ccc(C(O)(C(F)(F)F)C(F)(F)F)cc1] | 1,1,1,3,3,3-hexafluoro-2-(2'-methyl-4'-((5-(pyridin-4-ylmethyl)-2,5-diazabicyclo[2.2.2]octan-2-yl)methyl)-[1,1'-biphenyl]-4-yl)propan-2-ol | Aldehyde Int. 1A Amine Int. 10 | 550.6 |
| 77 | 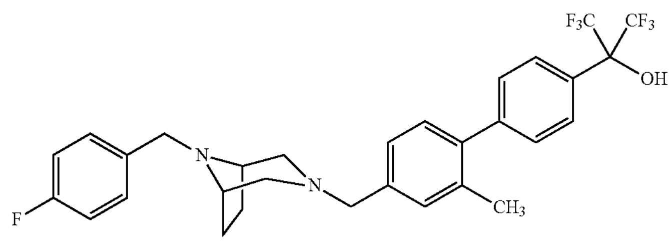 [SMILES: Cc1cc(CN2CC3CCC(C2)N3Cc2ccc(F)cc2)ccc1-c1ccc(C(O)(C(F)(F)F)C(F)(F)F)cc1] | 1,1,1,3,3,3-hexafluoro-2-(4'-((8-(4-fluorobenzyl)-3,8-diazabicyclo[3.2.1]octan-3-yl)methyl)-2'-methyl-[1,1'-biphenyl]-4-yl)propan-2-ol | Aldehyde Int. 1A Amine Int. 1B | 567.3 |
| 78 | 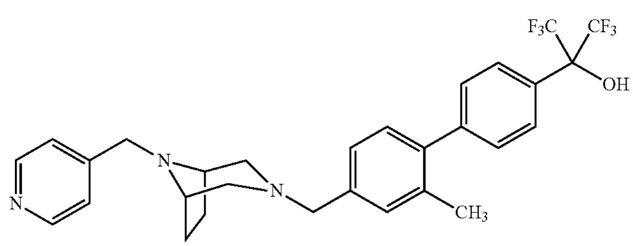 | 1,1,1,3,3,3-hexafluoro-2-(2'-methyl-4'-((8-(pyridin-4-ylmethyl)-3,8-diazabicyclo[3.2.1]octan-3-yl)methyl)-[1,1'-biphenyl]-4-yl)propan-2-ol | Aldehyde Int. 1A Amine Int. 1A | 550.5 |

Example 79: Gal4 Ligand Binding Assay

Compounds of the present invention were tested in a human RORγ ligand binding assay using a commercially available cell based ligand binding reporter assay in 96-well format (Cat #IB04001, INDIGO Biosciences, State College, Pa.). The N-terminal DNA binding domains (DBD) of the native RORγ and RORγt receptors have been substituted with that of the yeast GAL4-DBD and stably transfected in BEK293T cells that also stably express luciferase under the regulation by upstream activation sequence of yeast Gal4. These cells constitutively express high level RORγ activity due to binding of endogenous co-factors. Both agonist and inverse agonist activity can be detected. The assay was performed according to kit manufacturer's instructions as follows. 10 mM compound stocks were diluted serially 1:3 with DMSO and further diluted with provided media to generate 10 titration points from 60 μM to 3 nM. These treatment conditions were added to the plates as 2× media in 100 μL volume. Each plate includes a positive control with 10 titration points as well as 6negative control wells with vehicle only, with final DMSO concentration of 0.2%. RORγ reporter cells were rapidly thawed and added to the plates in 100 μL volume. The plates were incubated for 24h in a 37° C. humidified 5% $CO_2$ incubator. Media was removed before the addition of room temperature luciferous detection substrate. After 5 minute incubation, relative light units (RLUs) were quantified using a plate reading luminometer. Data was normalized to positive control wells with only 0.200DMSO. Before establishing internal controls, ursolic acid was used as control.

TABLE 2

$IC_{50}$ values for RORγt inverse agonists in RORγt Gal fusion assay.

| Example No. | RORγt ($IC_{50}$) | Example No. | RORγt ($IC_{50}$) | Example No. | RORγt ($IC_{50}$) | Example No. | RORγt ($IC_{50}$) |
|---|---|---|---|---|---|---|---|
| 1  | B | 2  | C | 3  | B | 4  | B |
| 5  | C | 6  | B | 7  | A | 8  | B |
| 9  | C | 10 | A | 11 | A | 12 | B |
| 13 | A | 14 | A | 15 | A | 16 | A |
| 17 | A | 18 | A | 19 | A | 20 | B |
| 21 | B | 22 | B | 23 | A | 24 | A |
| 25 | A | 26 | A | 27 | A | 28 | A |
| 29 | A | 30 | A | 31 | C | 32 | B |
| 33 | C | 34 | A | 35 | B | 36 | C |
| 37 | B | 38 | A | 39 | A | 40 | B |
| 41 | A | 42 | C | 43 | B | 44 | C |
| 45 | C | 46 | C | 47 | A | 48 | B |
| 49 | C | 50 | C | 51 | A | 52 | A |
| 53 | A | 54 | B | 55 | B | 56 | A |
| 57 | B | 58 | A | 59 | C | 60 | C |
| 61 | C | 62 | C | 63 | B | 64 | B |
| 65 | C | 66 | C | 67 | C | 68 | C |
| 69 | C | 70 | C | 71 | B | 72 | C |
| 73 | B | 74 | C | 75 | B | 76 | B |
| 77 | C | 78 | A |    |   |    |   |

A: $IC_{50}$ < 50 nM;
B: $IC_{50}$ = 50 nM – 250 nM;
C: $IC_{50}$ > 250 nM

Example 80: Human PBMC $T_H17$ Differentiation Assay

This assay tests compounds for their modulatory effect on RORγt as measured by IL-17 production by CD4+ T cells under conditions which favor $T_H17$ differentiation. Fresh healthy donor peripheral blood mononuclear cells (PBMC) were isolated using a Ficoll gradient. CD4+ T cells were purified using a negative selection kit and magnetic separation from Stemcell Technologies according to manufacturer's instruction (Cat #17952, Vancouver, Canada). 2.5× $10^4$ CD4+ T cells were incubated per well in a 96-well plate with 1:1 ratio of anti-CD3/CD28 stimulation beads (Cat #11131D, Gibco DYNAL, Waltham, Mass.) in the presence of rhIL-6 (50 ng/mL), rhIL-1b (10 ng/mL), rhTGF-b1 (1 ng/mL), rhIL-23 (5 ng/mL), anti-IL-4 (10 ug/mL) and anti-IFNg (10 ug/mL). Compounds were added 1 h before the start of the differentiation at various concentrations, with a final concentration of 0.1% DMSO. Cells were incubated at 37° C. 5% $CO_2$ for 3 days before harvesting of the supernatant for U-plex human IL-17A ELISA (Cat #K151ATA-4, Meso Scale Discovery, Rockville, Md.). Data was normalized to DMSO control wells. Cell viability was also measured after the supernatant removal, using MTT assay kit (CAT #11465007001, Sigma-Aldrich, St. Louis, Mo.).

In one embodiment, the compounds provided herein were found to have $IC_{50}$s of less than about 500 nM. In another embodiment, the compounds provided herein were found to have $IC_{50}$s of less than about 250 nM. In another embodiment, the compounds provided herein were found to have $IC_{50}$s of less than about 200 nM. In another embodiment, the compounds provided herein were found to have $IC_{50}$s of less than about 150 nM. In another embodiment, the compounds provided herein were found to have $IC_{50}$s of less than about 100 nM.

Example 81: Patient PBMC IL-17A Inhibition Assay

This assay is designed to screen compounds for their inhibitory effect on the release of IL-17 from isolated human $T_H17$ cells. Peripheral blood mononuclear cells (PBMC) from psoriasis, systemic lupus erythematosus, Crohn's disease and rheumatoid arthritis patients were purchased from Precision For Medicine (Frederick, Md.). 4×$10^5$ cells were incubated per well in a 96-well plate with Cytostim, human (Cat #130-092-172, Miltenyi Biotec, Bergisch Gladbach, Germany) according to manufacturer's instructions. Cells were incubated in the presence or absence of various concentrations of compounds, with a final concentration of 0.1% DMSO and starting at the time of stimulation. After 48 hours of incubation at 37° C. and 5% $CO_2$, supernatant was removed to measure IL-17A by ELISA (Cat #BMS2017, ThermoFisher Scientific, Waltham, Mass.). Data was normalized to DMSO control wells. Cell viability was also measured after the supernatant removal, using CellTiter-Glo Luminescent Cell Viability Assay Kit (Cat #G7570, Promega, Madison, Wis.).

In one embodiment, the compounds provided herein were found to have $IC_{50}$s of less than about 5 μM. In one embodiment, the compounds provided herein were found to have $IC_{50}$s of less than about 2.5 μM. In one embodiment, the compounds provided herein were found to have $IC_{50}$s of less than about 2 μM. In one embodiment, the compounds provided herein were found to have $IC_{50}$s of less than about 1 μM. In another embodiment, the compounds provided herein were found to have $IC_{50}$s of less than about 1500 nM. In another embodiment, the compounds provided herein were found to have $IC_{50}$s of less than about 500 nM. In another embodiment, the compounds provided herein were found to have IC$_{50}$s of less than about 250 nM. In another embodiment, the compounds provided herein were found to have IC$_{50}$s of less than about 300 nM. In another embodiment, the compounds provided herein were found to have IC$_{50}$s of less than about 200 nM. In another embodiment, the compounds provided herein were found to have IC$_{50}$s of less than about 150 nM. In another embodiment, the compounds provided herein were found to have IC$_{50}$s of less than about 100 nM. In another embodiment, the compounds provided herein were found to have IC$_{50}$s of less than about 50 nM.

The examples and embodiments described herein are for illustrative purposes only and in some embodiments, various modifications or changes are to be included within the purview of disclosure and scope of the appended claims.

What is claimed is:
1. A compound of Formula I, or a pharmaceutically acceptable salt, solvate, or stereoisomer thereof:

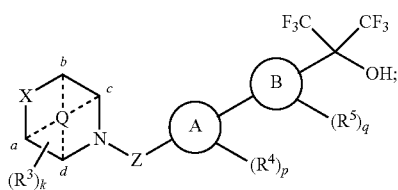

Formula (I)

wherein:

is phenyl, or a 5-membered or 6-membered heteroaryl ring;

is phenyl, or a 5-membered or 6-membered heteroaryl ring;
Q is —(CH$_2$)$_n$—, —CH$_2$YCH$_2$—, or —(CH$_2$)$_m$Y—, wherein —(CH$_2$)$_n$—, —CH$_2$YCH$_2$—, or —(CH$_2$)$_m$Y— is attached to the ring carbon atoms at a and b, c and d, a and c, or b and d;
X is —N(R$^{3a}$)—, —C(R$^{3b}$)(R$^{3c}$)—, or —O—;
Y is —O—, —S—, or —N(R$^{3d}$)—;
Z is —(C(R$^1$)(R$^2$))$_t$—;
each R$^1$ and each R$^2$ are each independently hydrogen, halo, or C$_1$-C$_6$alkyl;
each R$^3$ is independently selected from halo and C$_1$-C$_6$alkyl;
R$^{3a}$ is hydrogen, C$_1$-C$_6$alkyl, C$_1$-C$_6$haloalkyl, C$_2$-C$_9$heteroaryl, (C$_2$-C$_9$heteroaryl)-C$_1$-C$_6$alkylene-, —S(O)$_2$R$^{10}$, —C(O)R$^{10}$, —C(O)OR$^{11}$, or —C(O)N(R$^{11}$)$_2$, wherein C$_2$-C$_9$heteroaryl and (C$_2$-C$_9$heteroaryl)-C$_1$-C$_6$alkylene- are optionally substituted with 1 to 3 groups independently selected from halo, C$_1$-C$_6$alkyl, C$_1$-C$_6$haloalkyl, and hydroxyl;
R$^{3b}$ is hydrogen, halo, C$_1$-C$_6$alkyl, C$_1$-C$_6$haloalkyl, —N(R$^{11}$)S(O)$_2$R$^{10}$, —S(O)$_2$R$^{10}$, —C(O)R$^{10}$, —C(O)OR$^{11}$, or —C(O)N(R$^{11}$)$_2$;
R$^{3c}$ is hydrogen, halo, C$_1$-C$_6$alkyl, or C$_1$-C$_6$haloalkyl;

R$^{3d}$ is selected from hydrogen, C$_1$-C$_6$alkyl, C$_1$-C$_6$haloalkyl, —S(O)$_2$R$^8$, —C(O)R$^8$, —C(O)OR$^9$, and —C(O)N(R$^9$)$_2$;
each R$^4$ and each R$^5$ are each independently selected from halo, cyano, C$_1$-C$_6$alkyl, C$_1$-C$_6$haloalkyl, C$_1$-C$_6$alkoxy, —N(R$^7$)$_2$, —C(O)R$^6$, —C(O)OR$^7$, —C(O)N(R$^7$)$_2$, —N(R$^7$)C(O)R$^6$, —N(R$^7$)SO$_2$R$^6$, —SO$_2$R$^6$, and —SO$_2$N(R$^7$)$_2$;
each R$^6$ is independently C$_1$-C$_6$alkyl or C$_1$-C$_6$haloalkyl;
each R$^7$ is independently hydrogen, C$_1$-C$_6$alkyl, or C$_1$-C$_6$haloalkyl;
R$^8$ is C$_1$-C$_6$alkyl or C$_1$-C$_6$haloalkyl;
each R$^9$ is independently hydrogen, C$_1$-C$_6$alkyl, or C$_1$-C$_6$haloalkyl;
R$^{10}$ is C$_1$-C$_6$alkyl, C$_1$-C$_6$haloalkyl, C$_1$-C$_6$alkyl-O—C$_1$-C$_6$alkyl-, C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene-, wherein the C$_3$-C$_8$cycloalkyl, C$_2$-C$_9$heterocyclyl, phenyl, (phenyl)-C$_1$-C$_6$alkylene-, C$_2$-C$_9$heteroaryl, or (C$_2$-C$_9$heteroaryl)-C$_1$-C$_6$alkylene- is optionally substituted with 1 to 3 groups selected from halo, C$_1$-C$_6$alkyl, C$_1$-C$_6$haloalkyl, and hydroxyl;
each R$^{11}$ is independently hydrogen, C$_1$-C$_6$alkyl, or C$_1$-C$_6$haloalkyl;
k is 0, 1, 2, 3, or 4;
m is 1 or 2;
n is 1, 2, 3, or 4;
p is 0, 1, 2, 3, or 4;
q is 0, 1, 2, 3, or 4; and
t is 0, 1, 2, or 3.

2. The compound of claim 1 having the Formula (II):

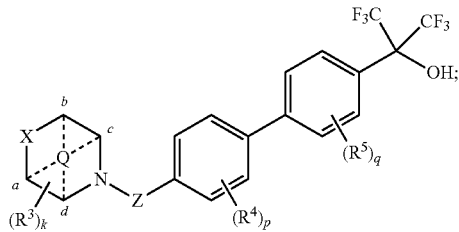

Formula (II)

or a pharmaceutically acceptable salt, solvate, or stereoisomer thereof.

3. The compound of claim 2, or a pharmaceutically acceptable salt, solvate, or stereoisomer thereof, wherein X is —NR$^{3a}$— or —C(R$^{3b}$)(R$^{3c}$)—.

4. The compound of claim 2 having the Formula (IIa):

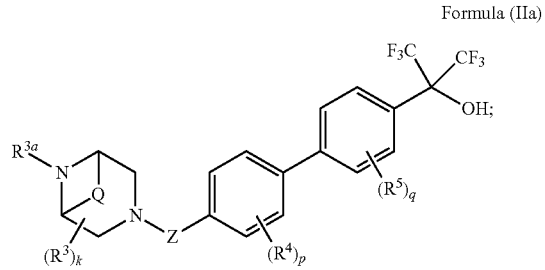

Formula (IIa)

129 or a pharmaceutically acceptable salt, solvate, or stereoisomer thereof.

5. The compound of claim 4, or a pharmaceutically acceptable salt, solvate, or stereoisomer thereof, wherein each $R^1$ and each $R^2$ are hydrogen.

6. The compound of claim 5, or a pharmaceutically acceptable salt, solvate, or stereoisomer thereof, wherein t is 1.

7. The compound of claim 6, or a pharmaceutically acceptable salt, solvate, or stereoisomer thereof, wherein $R^{3a}$ is $C_1$-$C_6$alkyl, ($C_2$-$C_9$heteroaryl)-$C_1$-$C_6$alkylene-, —S(O)$_2$R$^{10}$, or —C(O)R$^{10}$, wherein ($C_2$-$C_9$heteroaryl)-$C_1$-$C_6$alkylene- is optionally substituted with 1 or 2 groups each independently selected from halo, $C_1$-$C_6$alkyl, $C_1$-$C_6$haloalkyl, and hydroxyl.

8. The compound of claim 7, or a pharmaceutically acceptable salt, solvate, or stereoisomer thereof, wherein $R^{3a}$ is —S(O)$_2$R$^{10}$.

9. The compound of claim 8, or a pharmaceutically acceptable salt, solvate, or stereoisomer thereof, wherein $R^{10}$ is $C_1$-$C_6$alkyl.

10. The compound of claim 7, or a pharmaceutically acceptable salt, solvate, or stereoisomer thereof, wherein Q is —(CH$_2$)$_n$—.

11. The compound of claim 10, or a pharmaceutically acceptable salt, solvate, or stereoisomer thereof, wherein n is 2.

12. The compound of claim 11, or a pharmaceutically acceptable salt, solvate, or stereoisomer thereof, wherein p is 1, 2, or 3.

13. The compound of claim 12, or a pharmaceutically acceptable salt, solvate, or stereoisomer thereof, wherein each $R^4$ is independently halo, $C_1$-$C_6$alkyl, or $C_1$-$C_6$haloalkyl.

14. The compound of claim 11, or a pharmaceutically acceptable salt, solvate, or stereoisomer thereof, wherein q is 0, 1, or 2.

15. The compound of claim 14, or a pharmaceutically acceptable salt, solvate, or stereoisomer thereof, wherein each $R^5$ is independently halo, $C_1$-$C_6$alkyl, or $C_1$-$C_6$haloalkyl.

16. The compound of claim 11, or a pharmaceutically acceptable salt, solvate, or stereoisomer thereof, wherein k is 0.

17. The compound of claim 1 selected from:
2-(2'-ethyl-4'-(((1R,5S)-7-(methylsulfonyl)-3-oxa-7,9-diazabicyclo[3.3.1]nonan-9-yl)methyl)-[1,1'-biphenyl]-4-yl)-1,1,1,3,3,3-hexafluoropropan-2-ol;
2-(2'-ethyl-4'-(((1R,5S)-9-(methylsulfonyl)-3-oxa-7,9-diazabicyclo[3.3.1]nonan-7-yl)methyl)-[1,1'-biphenyl]-4-yl)-1,1,1,3,3,3-hexafluoropropan-2-ol;
2-(2-chloro-2'-ethyl-3',5'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-2,3',5'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-3',5'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(3-chloro-4-(4-ethyl-6-((8-(methylsulfonyl)-3,8-diazabicyclo[3.2.1]octan-3-yl)methyl)pyridin-3-yl)phenyl)-1,1,1,3,3,3-hexafluoropropan-2-ol;
2-(2-chloro-2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol;

130

2-(2-chloro-5'-fluoro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-2,6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-chloro-2'-ethyl-6'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-chloro-2'-ethyl-5'-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-4'-((3-(methylsulfonyl)-3,8-diazabicyclo[3.2.1]octan-8-yl)methyl)-[1,1'-biphenyl]-4-yl)-1,1,1,3,3,3-hexafluoropropan-2-ol;
1,1,1,3,3,3-hexafluoro-2-(5'-fluoro-2'-isopropyl-2-methyl-4'-((8-(methylsulfonyl)-3,8-diazabicyclo[3.2.1]octan-3-yl)methyl)-[1,1'-biphenyl]-4-yl)propan-2-ol;
2-(2-chloro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-chloro-2'-isopropyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-2,3',6'-trifluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-chloro-2'-ethyl-3',6'-difluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-2-fluoro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2,2'-diethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-ethyl-2'-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2-chloro-2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-3',5'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(6'-ethyl-2',3'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(2'-ethyl-3',6'-difluoro-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;
2-(4-(2-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol;
2-(4-(4-ethyl-6-((8-(methylsulfonyl)-3,8-diazabicyclo[3.2.1]octan-3-yl)methyl)pyridin-3-yl)-3-methylphenyl)-1,1,1,3,3,3-hexafluoropropan-2-ol;
2'-ethyl-4-(1,1,1,3,3,3-hexafluoro-2-hydroxypropan-2-yl)-4'-((8-(methylsulfonyl)-3,8-diazabicyclo[3.2.1]octan-3-yl)methyl)-[1,1'-biphenyl]-2-carboxamide;
2-(6-(2-ethyl-4-((8-(methylsulfonyl)-3,8-diazabicyclo[3.2.1]octan-3-yl)methyl)phenyl)pyridin-3-yl)-1,1,1,3,3,3-hexafluoropropan-2-ol;

2-(4-(3-ethyl-5-((8-(methylsulfonyl)-3,8-diazabicyclo[3.2.1]octan-3-yl)methyl)pyridin-2-yl)-3-methylphenyl)-1,1,1,3,3,3-hexafluoropropan-2-ol;

1,1,1,3,3,3-hexafluoro-2-(3'-(8-(methylsulfonyl)-3,8-diazabicyclo[3.2.1]octan-3-yl)-[1,1'-biphenyl]-4-yl)propan-2-ol;

2-(2'-ethyl-2-methyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(2'-isopropyl-2-methyl-4'-((8-(methylsulfonyl)-3,8-diazabicyclo[3.2.1]octan-3-yl)methyl)-[1,1'-biphenyl]-4-yl)propan-2-ol;

2-(4'-((8-(5-(tert-butyl)-1,2,4-oxadiazol-3-yl)-3,8-diazabicyclo[3.2.1]octan-3-yl)methyl)-2'-methyl-[1,1'-biphenyl]-4-yl)-1,1,1,3,3,3-hexafluoropropan-2-ol;

2-(2'-ethyl-4'-((5-(methylsulfonyl)-2,5-diazabicyclo[2.2.2]octan-2-yl)methyl)-[1,1'-biphenyl]-4-yl)-1,1,1,3,3,3-hexafluoropropan-2-ol;

2-(2'-ethyl-4'-((5-(methylsulfonyl)-2,5-diazabicyclo[2.2.1]heptan-2-yl)methyl)-[1,1'-biphenyl]-4-yl)-1,1,1,3,3,3-hexafluoropropan-2-ol;

1-(3-((2-ethyl-4'-(1,1,1,3,3,3-hexafluoro-2-hydroxypropan-2-yl)-[1,1'-biphenyl]-4-yl)methyl)-3,8-diazabicyclo[3.2.1]octan-8-yl)ethan-1-one;

2-(2'-bromo-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-bromo-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

2-(4'-((8-ethyl-3,8-diazabicyclo[3.2.1]octan-3-yl)methyl)-2'-methyl-[1,1'-biphenyl]-4-yl)-1,1,1,3,3,3-hexafluoropropan-2-ol;

(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(tetrahydro-2H-pyran-4-yl)methanone;

ethyl 3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octane-8-carboxylate;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-3-methoxypropan-1-one;

N-(3-((4'-(1,1,1,3,3,3-hexafluoro-2-hydroxypropan-2-yl)-2-methyl-[1,1'-biphenyl]-4-yl)methyl)-3-azabicyclo[3.2.1]octan-8-yl)methanesulfonamide;

1,1,1,3,3,3-hexafluoro-2-(2'-methyl-4'-((8-(pyrimidin-4-ylmethyl)-3,8-diazabicyclo[3.2.1]octan-3-yl)methyl)-[1,1'-biphenyl]-4-yl)propan-2-ol;

2-(2'-chloro-4'-((8-((2-methylpyridin-4-yl)methyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(2'-methyl-4'-((5-(methylsulfonyl)-2,5-diazabicyclo[2.2.1]heptan-2-yl)methyl)-[1,1'-biphenyl]-4-yl)propan-2-ol;

1,1,1,3,3,3-hexafluoro-2-(2'-methyl-4'-((5-(methylsulfonyl)-2,5-diazabicyclo[2.2.2]octan-2-yl)methyl)-[1,1'-biphenyl]-4-yl)propan-2-ol;

1,1,1,3,3,3-hexafluoro-2-(2'-methyl-4'-((8-(pyridazin-4-ylmethyl)-3,8-diazabicyclo[3.2.1]octan-3-yl)methyl)-[1,1'-biphenyl]-4-yl)propan-2-ol;

2-(2'-ethyl-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-ethyl-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)-2-methoxyethan-1-one;

2-(2'-chloro-4'-((8-(methylsulfonyl)-3,8-diazabicyclo[3.2.1]octan-3-yl)methyl)-[1,1'-biphenyl]-4-yl)-1,1,1,3,3,3-hexafluoropropan-2-ol;

2-(2'-chloro-4'-((8-(pyridin-4-ylmethyl)-3,8-diazabicyclo[3.2.1]octan-3-yl)methyl)-[1,1'-biphenyl]-4-yl)-1,1,1,3,3,3-hexafluoropropan-2-ol;

1,1,1,3,3,3-hexafluoro-2-(4'-((8-(methylsulfonyl)-3,8-diazabicyclo[3.2.1]octan-3-yl)methyl)-2'-(trifluoromethyl)-[1,1'-biphenyl]-4-yl)propan-2-ol;

1,1,1,3,3,3-hexafluoro-2-(4'-((8-(pyridin-4-ylmethyl)-3,8-diazabicyclo[3.2.1]octan-3-yl)methyl)-2'-(trifluoromethyl)-[1,1'-biphenyl]-4-yl)propan-2-ol;

1,1,1,3,3,3-hexafluoro-2-(2'-fluoro-4'-((8-(pyridin-4-ylmethyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-((trifluoromethyl)sulfonyl)-3,8-diazabicyclo[3.2.1]octan-3-yl)methyl)-[1,1'-biphenyl]-4-yl)propan-2-ol;

1,1,1,3,3,3-hexafluoro-2-(2'-fluoro-4'-((8-(methylsulfonyl)-3,8-diazabicyclo[3.2.1]octan-3-yl)methyl)-[1,1'-biphenyl]-4-yl)propan-2-ol;

1,1,1,3,3,3-hexafluoro-2-(4'-((8-((4-fluorophenyl)sulfonyl)-3,8-diazabicyclo[3.2.1]octan-3-yl)methyl)-2'-methyl-[1,1'-biphenyl]-4-yl)propan-2-ol;

1,1,1,3,3,3-hexafluoro-2-(4'-((8-((3-fluoropyridin-4-yl)methyl)-3,8-diazabicyclo[3.2.1]octan-3-yl)methyl)-2'-methyl-[1,1'-biphenyl]-4-yl)propan-2-ol;

2-(4'-((8-(cyclopropylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

2-(4'-((8-(benzylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

1,1,1,3,3,3-hexafluoro-2-(2'-methyl-4'-((8-((2-methylpyridin-4-yl)methyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-((2,2,2-trifluoroethyl)sulfonyl)-3,8-diazabicyclo[3.2.1]octan-3-yl)methyl)-[1,1'-biphenyl]-4-yl)propan-2-ol;

1,1,1,3,3,3-hexafluoro-2-(2'-methyl-4'-((8-(propylsulfonyl)-3,8-diazabicyclo[3.2.1]octan-3-yl)methyl)-[1,1'-biphenyl]-4-yl)propan-2-ol;

2-(4'-((8-(ethylsulfonyl)-3,8-diazabicyclo[3.2.1]octan-3-yl)methyl)-2'-methyl-[1,1'-biphenyl]-4-yl)-1,1,1,3,3,3-hexafluoropropan-2-ol;

4-((3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)methyl)pyridin-2-ol;

1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one;

1,1,1,3,3,3-hexafluoro-2-(2'-methyl-4'-((5-(pyridin-4-ylmethyl)-2,5-diazabicyclo[2.2.1]heptan-2-yl)methyl)-[1,1'-biphenyl]-4-yl)propan-2-ol;

1,1,1,3,3,3-hexafluoro-2-(2'-methyl-4'-((8-(methylsulfonyl)-3,8-diazabicyclo[3.2.1]octan-3-yl)methyl)-[1,1'-biphenyl]-4-yl)propan-2-ol;

2-(2,6-difluorophenyl)-1-(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)ethan-1-one;

(3-((4'-(1,1,1,3,3,3-hexafluoro-2-hydroxypropan-2-yl)-2-methyl-[1,1'-biphenyl]-4-yl)methyl)-3,8-diazabicyclo[3.2.1]octan-8-yl)(pyridin-4-yl)methanone;

1,1,1,3,3,3-hexafluoro-2-(2'-methyl-4'-((5-(pyridin-4-yl-methyl)-2,5-diazabicyclo[2.2.2]octan-2-yl)methyl)-[1,1'-biphenyl]-4-yl)propan-2-ol;

1,1,1,3,3,3-hexafluoro-2-(4'-((8-(4-fluorobenzyl)-3,8-diazabicyclo[3.2.1]octan-3-yl)methyl)-2'-methyl-[1,1'-biphenyl]-4-yl)propan-2-ol;

1,1,1,3,3,3-hexafluoro-2-(2'-methyl-4'-((8-(pyridin-4-yl-methyl)-3,8-diazabicyclo[3.2.1]octan-3-yl)methyl)-[1,1'-biphenyl]-4-yl)propan-2-ol;

1,1,1,3,3,3-hexafluoro-2-(4'-((3-(pyridin-4-ylmethyl)-3,8-diazabicyclo[3.2.1]octan-8-yl)methyl)-[1,1'-biphenyl]-4-yl)propan-2-ol; and 1,1,1,3,3,3-hexafluoro-2-(4'-((8-(pyridin-4-ylmethyl)-3,8-diazabicyclo[3.2.1]octan-3-yl)methyl)-[1,1'-biphenyl]-4-yl)propan-2-ol; or a pharmaceutically acceptable salt or solvate thereof.

18. A pharmaceutical composition comprising a compound of claim 1 or a pharmaceutically acceptable salt or solvate thereof, and a pharmaceutically acceptable carrier.

19. A method of treating a disease, disorder, or condition in an individual in need thereof comprising administering to the individual a therapeutically effective amount of a compound of claim 1, or a pharmaceutically acceptable salt or solvate thereof, wherein the disease, disorder, or condition is selected from psoriasis, psoriatic arthritis, uveitis, ulcerative colitis, asthma, allergic rhinitis, chronic obstructive pulmonary disease (COPD), atopic dermatitis, vitiligo, vesiculobullous dermatosis, rheumatoid arthritis, ankylosing spondylitis, reactive arthritis, arthritis associated with inflammatory bowel disease, juvenile rheumatoid arthritis, Crohn's disease, inflammatory bowel disease, lupus, lupus nephritis, multiple sclerosis, axial spodyloarthritides, hidraenitis suppurativa, Sjögren's syndrome, regional enteritis, Tolosa-Hunt syndrome, undifferentiated connective tissue disease, obesity, obesity-induced insulin resistance, atherosclerosis, and type II diabetes.

\* \* \* \* \*